(12) United States Patent
Chtourou et al.

(10) Patent No.: US 8,802,620 B2
(45) Date of Patent: Aug. 12, 2014

(54) DEMANNOSYLATED RECOMBINANT FACTOR VIII FOR THE TREATMENT OF PATIENTS WITH HAEMOPHILIA A

(75) Inventors: Abdessatar Sami Chtourou, Elancourt (FR); Sébastien Lacroix-Desmazes, Issy-les-Moulineaux (FR); Srinivas Kaveri, Malakoff (FR); Suryasarathi Dasgupta, Boston, MA (US); Jagaadeesh Bayry, Issy-les-Moulineaux (FR)

(73) Assignees: Institut National de la Sante et de la Recherche Medicale (INSERM), Paris (FR); LFB Biotechnologies, Les Ulis (FR)

( * ) Notice: Subject to any disclaimer, the term of this patent is extended or adjusted under 35 U.S.C. 154(b) by 899 days.

(21) Appl. No.: 12/596,323

(22) PCT Filed: Apr. 21, 2008

(86) PCT No.: PCT/IB2008/001417
§ 371 (c)(1),
(2), (4) Date: Apr. 22, 2010

(87) PCT Pub. No.: WO2008/129422
PCT Pub. Date: Oct. 30, 2008

(65) Prior Publication Data
US 2010/0197578 A1 Aug. 5, 2010

(30) Foreign Application Priority Data

Apr. 20, 2007 (EP) ..................................... 07290495

(51) Int. Cl.
| | | |
|---|---|---|
| *A61K 38/00* | (2006.01) | |
| *A61P 7/00* | (2006.01) | |
| *A61K 38/36* | (2006.01) | |
| *A61P 7/02* | (2006.01) | |
| *C07K 14/745* | (2006.01) | |
| *A61K 38/37* | (2006.01) | |

(52) U.S. Cl.
USPC .......... 514/1.1; 514/13.5; 514/13.7; 514/14.1

(58) Field of Classification Search
None
See application file for complete search history.

(56) References Cited

U.S. PATENT DOCUMENTS 6,060,447 A * 5/2000 Chapman et al. ............ 514/13.7
2006/0160994 A1* 7/2006 Lenting et al. ................ 530/383

OTHER PUBLICATIONS

Velan et al, N-glycosylation of human acetylcholinesterase: effects on activity, stability and biosynthesis, Biochem. J. (1993) 296, 649-656.*
Dorner et al, The relationship of N-linked glycosylation and heavy chain-binding protein association with the secretion of glycoproteins, J Cell Biol. Dec. 1987;105(6 Pt 1):2665-74.*
Parker et al, Comparative immunogenicity of recombinant B domain-deleted porcine factor VIII and Hyate:C in hemophilia A mice presensitized to human factor VIII, Journal of Thrombosis and Haemostasis, 2004, 2: 605-611.*
Current Protocols in Molecular Biology, John Wiley & Sons, NY 1989, Excerpts from Section II—6.3—6.4, pp. 190-194.
Banchereau, J. et al., "Dendritic cells and the control of immunity"; Nature; Mar. 19, 1998; vol. 392; pp. 245-252.
Barrow, R. et al., "Antigenicity of putative phospholipid membrane-binding residues in factor VIII"; Blood; Jan. 1, 2001; vol. 97, No. 1; pp. 169-174.
Bergman, Y. et al., "Two regulatory elements for immunoglobulin κ light chain gene expression"; Proc. Natl. Acad. Sci. USA; Nov. 1984; vol. 81; pp. 7041-7045.
Boshart, M. et al., "A Very Strong Enhancer Is Located Upstream of an Immediate Early Gene of Human Cytomegalovirus"; Cell; Jun. 1985; vol. 41; pp. 521-530.
Bovenschen, N. et al., "The B domain of coagulation factor VIII interacts with the asialoglycoprotein receptor"; Journal of Thrombosis and Haemostasis; Feb. 28, 2005; vol. 3; pp. 1257-1265.
Dasgupta, S. et al., "A role for exposed mannosylations in presentation of human therapeutic self-proteins to CD4+ T lymphocytes"; PNAS; May 22, 2007; vol. 104, No. 21; pp. 8965-8970.
deBiasi, R. et al., "Incidence of Factor VIII Inhibitor Development in Hemophilia A Patients Treated with Less Pure Plasma Derived Concentrates"; Thrombosis and Haemostasis; 1994; pp. 544-547.
DeNoto, F. et al., "Human growth hormone DNA sequence and mRNA structure: possible alternative splicing"; Nucleic Acids Research; 1981; vol. 9, No. 15; pp. 3719-3730.
Ehrenforth, S. et al., "Incidence of development of factor VIII and factor IX inhibitors in haemophiliacs"; The Lancet; Mar. 7, 1992; vol. 339; pp. 594-598.
Geijtenbeek, T. et al., "Identification of DC-SIGN, a Novel Dendritic Cell-Specific ICAM-3 Receptor that Supports Primary Immune Responses"; Cell; Mar. 3, 2000; vol. 100; pp. 575-585.
Geijtenbeek, T. et al., "Self-And Nonself-Recognition by C-Type Lectins on Dendritic Cells"; Annu. Rev. Immunol.; 2004; vol. 22; pp. 33-54; Figures 1 and 2, 2 pages; Contents, pp. v-vii.
Gringeri, A. et al., "Cost of care and quality of life for patients with hemophilia complicated by inhibitors: the COCIS Study Group"; Blood; Oct. 1, 2003; vol. 102, No. 7; pp. 2358-2363.
Jacquemin, M. et al., "A human antibody directed to the factor VIII C1 domain inhibits factor VIII cofactor activity and binding to von Willebrand factor"; Blood; Jan. 1, 2000; vol. 95, No. 1; pp. 156-163.
Jacquemin, M. et al., "Mechanism and Kinetics of Factor VIII Inactivation: Study With an IgG4 Monoclonal Antibody Derived From a Hemophilia A Pateint With Inhibitor"; Blood; Jul. 15, 1998; vol. 92, No. 2; pp. 496-506.

(Continued)

*Primary Examiner* — Marcela M Cordero Garcia
*Assistant Examiner* — Sergio Coffa
(74) *Attorney, Agent, or Firm* — Whitham Curtis Christofferson & Cook, PC

(57) ABSTRACT

There is provided in accordance with the practice of this invention a demannosylated Factor VIII, the immunogenicity of which is substantially decreased or abolished in Human. The modified factor VIII is disclosed together with the modified amino acid sequence, changed by at least one substitution. The modified factor VIII is useful for hemophiliacs, either to avoid or prevent the action of inhibitory anti-FVIII antibodies.

16 Claims, 16 Drawing Sheets

(56) References Cited

OTHER PUBLICATIONS

Jacquemin, M. et al., "CD4+ T-cell clones specific for wild-type factor VIII: a molecular mechanism responsible for a higher incidence of inhibitor formation in mild/moderate hemophilia A"; Blood; Feb. 15, 2003; vol. 101, Number; pp. 1351-1358.

Kaufman, R. et al., "Construction of a Modular Dihydrofolate Reductase cDNA Gene: Analysis of Signals Utilized for Efficient Expression"; Molecular and Cellular Biology; Nov. 1982; vol. 2, No. 11; pp. 1304-1319.

Kaufman, R. et al., "Genetic engineering of factor VIII"; Nature; Nov. 9, 1989; vol. 342; pp. 207-208.

Keler, T. et al., "Mannose receptor-targeted vaccines"; Expert Opin. Biol. Ther.; 2004; pp. 1953-1962.

Lenting, P. et al., "Correction of the bleeding time in vol Willebrand factor (VWF)-deficient mice using murine VWF"; Blood; Mar. 1, 2007; vol. 109, No. 5; pp. 2267-2268.

Lenting, P. et al., "The Life Cycle of Coagulation Factor VIII in View of Its Structure and Function"; Blood; Dec. 1, 1998; vol. 92, No. 11; pp. 3983-3996.

Linehan, S. et al., "Endogenous ligands of carbohydrate recognition domains of the mannose receptor in murine macrophages, endothelial cells and secretory cells; potential relevance to inflammation and immunity"; Eur. J. Immunol. 2001; vol. 31; pp. 1857-1866.

Loh, D. et al., "Molecular Basis of a Mouse Strain-Specific Anti-Hapten Response"; Cell; May 1983; vol. 33; pp. 85-93.

Lusher, J. et al., "The safety and efficacy of B-domain deleted recombinant factor VIII concentrate in patients with severe haemophilia A"; Haemophilipa; 2003; vol. 9; pp. 38-49.

Maniatis, T. et al., "Molecular Cloning: A Laboratory Manual"; Southern Transfer; 1982; pp. 387-389.

Miao, H. et al., "Bioengineering of coagulation factor VIII for improved secretion"; Blood; May 1, 2004; vol. 103, No. 9; pp. 3412-3419.

Palmiter, R. et al., "Metallothionein-Human GH Fusion Genes Stimulate Growth of Mice"; Science; Nov. 18, 1983; vol. 222; pp. 809-814.

Peerlinck, K. et al., "Antifactor VIII Antibody Inhibiting Allogeneic but not Autologous Factor VIII in Patients With Mild Hemophilia A"; Blood; Apr. 1, 1999; vol. 93, No. 7; pp. 2267-2273.

Pittman, D. et al., "Role of the B Domain for Factor VIII and Factor V Expression and Function"; Blood; Dec. 15, 1994; vol. 84, No. 12; pp. 4214-4225.

Saenko, E. et al., "The future of recombinant coagulation factors"; Journal of Thrombosis and Haemostasis; 2003; vol. 1; pp. 922-930.

Saint-Remy, J. et al., "Anti-Idiotypic Antibodies: From Regulation to Therapy of Factor VIII Inhibitors"; Vox Sang; 1999; vol. 77 (suppl.); pp. 21-24.

Sallusto, F. et al., "Dendritic Cells Use Macropinocytosis and the Mannose Receptor to Concentrate Macromolecules in the Major Histocompatibility Complex Class II Compartment: Downregulation by Cytokines and Bacterial Products"; J. Exp. Med.; Aug. 1995; vol. 182; pp. 389-400.

Subramani, S. et al., "Expression of the Mouse Dihydrofolate Reductase Complementary Deoxyribonucleic Acid in Simian Virus 40 Vectors"; Molecular and Cellular Biology; Sep. 1981; vol. 1, No. 9; pp. 854-864.

Toole, J. et al., "Molecular cloning of a cDNA encoding human antihaemophilic factor"; Nature; Nov. 22, 1984; vol. 312; pp. 342-347.

Trombetta, E. et al., "Cell Biology of Antigen Processing In Vitro and In Vivo"; Annu. Rev. Immunol.; 2005; vol. 23; pp. 975-1028.

"Identification of cDNA Clones of Interest"; Construction and Analysis of cDNA Libraries; Molecular Cloning; 1989; vol. 2; pp. 8.46-8.49.

* cited by examiner

Figure 1
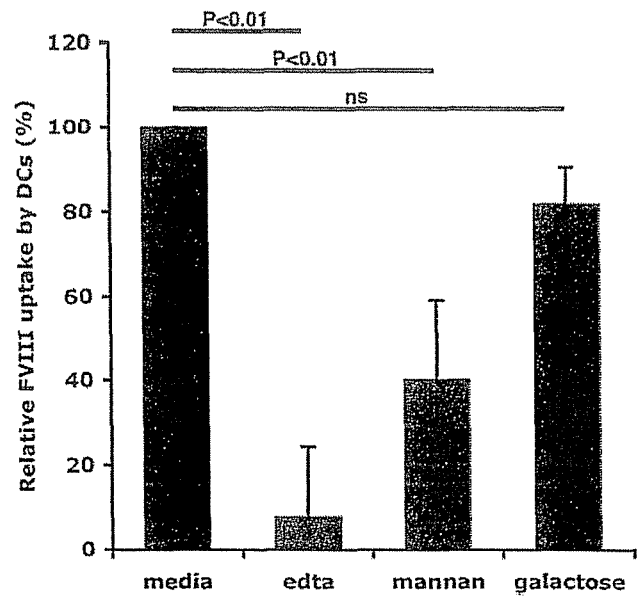
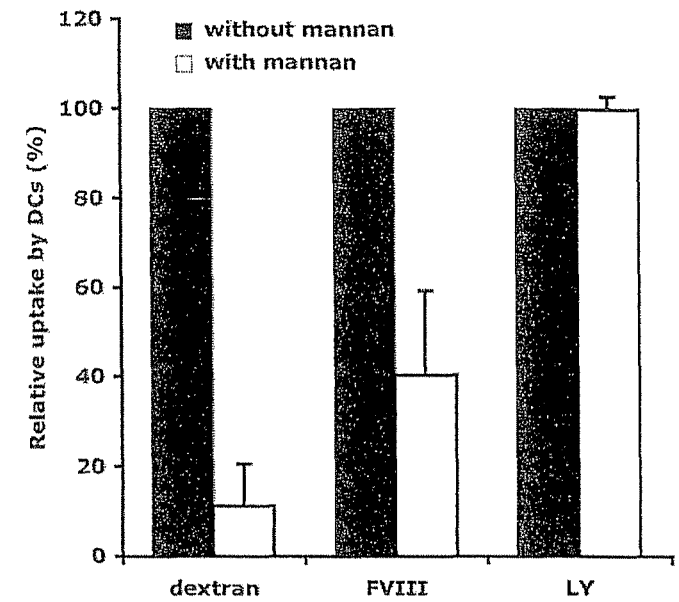

Figure 2
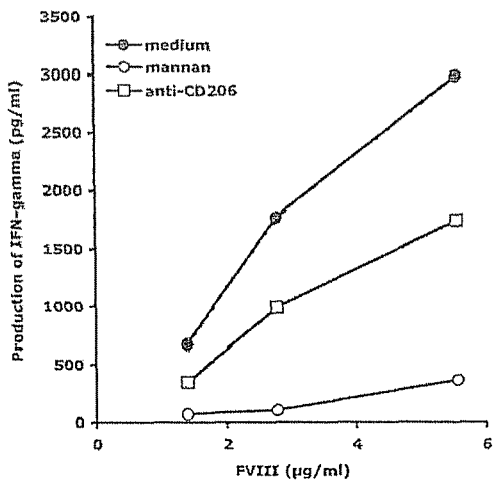
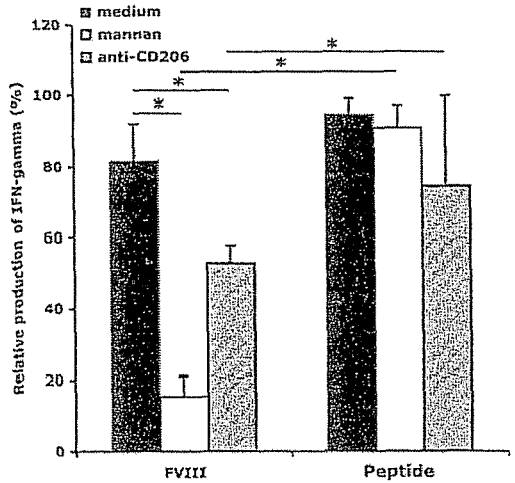
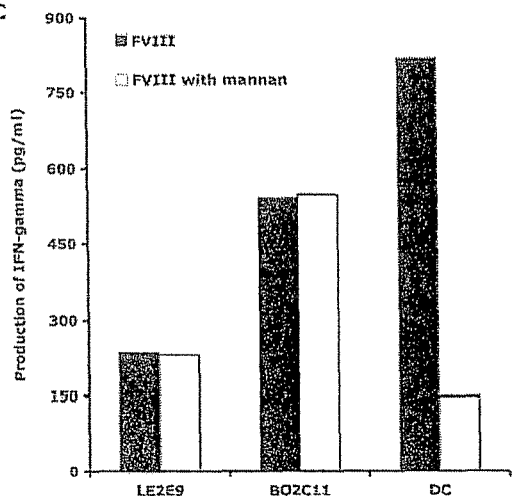

Figure 3
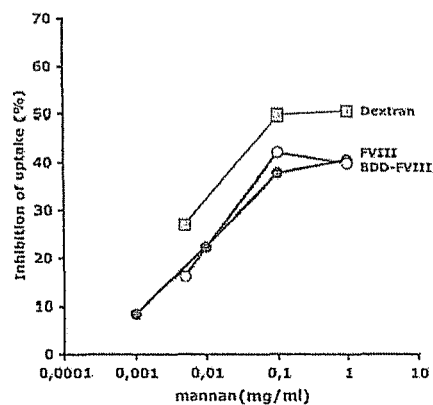
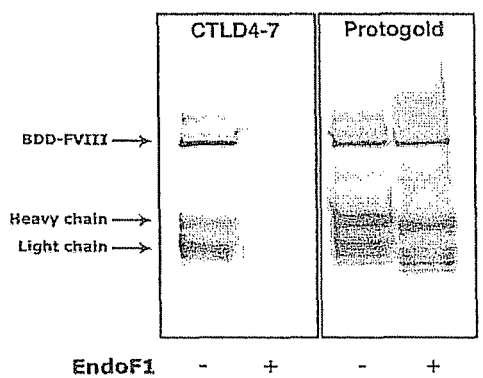
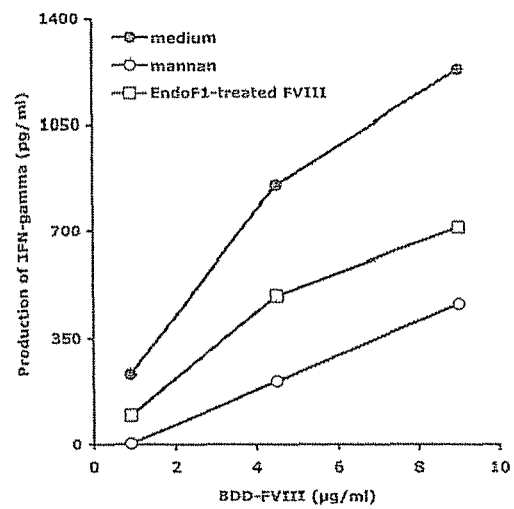

FVIII

Heavy Chain

B domain

Light Chain

Figure 6

Native Full length hFVIII (SEQ ID NO: 1):

```
   1 MQIELSTCFF LCLLRFCFSA TRRYYLGAVE LSWDYMQSDL GELPVDARFP PRVPKSFPFN
  61 TSVVYKKTLF VEFTDHLFNI AKPRPPWMGL LGPTIQAEVY DTVVITLKNM ASHPVSLHAV
 121 GVSYWKASEG AEYDDQTSQR EKEDDKVFPG GSHTYVWQVL KENGPMASDP LCLTYSYLSH
 181 VDLVKDLNSG LIGALLVCRE GSLAKEKTQT LHKFILLFAV FDEGKSWHSE TKNSLMQDRD
 241 AASARAWPKM HTVNGYVNRS LPGLIGCHRK SVYWHVIGMG TTPEVHSIFL EGHTFLVRNH
 301 RQASLEISPI TFLTAQTLLM DLGQFLLFCH ISSHQHDGME AYVKVDSCPE EPQLRMKNNE
 361 EAEDYDDDLT DSEMDVVRFD DDNSPSFIQI RSVAKKHPKT WVHYIAAEEE DWDYAPLVLA
 421 PDDRSYKSQY LNNGPQRIGR KYKKVRFMAY TDETFKTREA IQHESGILGP LLYGEVGDTL
 481 LIIFKNQASR PYNIYPHGIT DVRPLYSRRL PKGVKHLKDF PILPGEIFKY KWTVTVEDGP
 541 TKSDPRCLTR YYSSFVNMER DLASGLIGPL LICYKESVDQ RGNQIMSDKR NVILFSVFDE
 601 NRSWYLTENI QRFLPNPAGV QLEDPEFQAS NIMHSINGYV FDSLQLSVCL HEVAYWYILS
 661 IGAQTDFLSV FFSGYTFKHK MVYEDTLTLF PFSGETVFMS MENPGLWILG CHNSDFRNRG
 721 MTALLKVSSC DKNTGDYYED SYEDISAYLL SKNNAIEPRS FSQNSRHPST RQKQFNATTI
 781 PENDIEKTDP WFAHRTPMPK IQNVSSSDLL MLLRQSPTPH GLSLSDLQEA KYETFSDDPS
 841 PGAIDSNNSL SEMTHFRPQL HHSGDMVFTP ESGLQLRLNE KLGTTAATEL KKLDFKVSST
 901 SNNLISTIPS DNLAAGTDNT SSLGPPSMPV HYDSQLDTTL FGKKSSPLTE SGGPLSLSEE
 961 NNDSKLLESG LMNSQESSWG KNVSSTESGR LFKGKRAHGP ALLTKDNALF KVSISLLKTN
1021 KTSNNSATNR KTHIDGPSLL IENSPSVWQN ILESDTEFKK VTPLIHDRML MDKNATALRL
1081 NHMSNKTTSS KNMEMVQQKK EGPIPPDAQN PDMSFFKMLF LPESARWIQR THGKNSLNSG
1141 QGPSPKQLVS LGPEKSVEGQ NFLSEKNKVV VGKGEFTKDV GLKEMVFPSS RNLFLTNLDN
1201 LHENNTHNQE KKIQEEIEKK ETLIQENVVL PQIHTVTGTK NFMKNLFLLS TRQNVEGSYD
1261 GAYAPVLQDF RSLNDSTNRT KKHTAHFSKK GEEENLEGLG NQTKQIVEKY ACTTRISPNT
1321 SQQNFVTQRS KRALKQFRLP LEETELEKRI IVDDTSTQWS KNMKHLTPST LTQIDYNEKE
1381 KGAITQSPLS DCLTRSHSIP QANRSPLPIA KVSSFPSIRP IYLTRVLFQD NSSHLPAASY
1441 RKKDSGVQES SHFLQGAKKN NLSLAILTLE MTGDQREVGS LGTSATNSVT YKKVENTVLP
1501 KPDLPKTSGK VELLPKVHIY QKDLFPTETS NGSPGHLDLV EGSLLQGTEG AIKWNEANRP
1561 GKVPFLRVAT ESSAKTPSKL LDPLAWDNHY GTQIPKEEWK SQEKSPEKTA FKKKDTILSL
1621 NACESNHAIA AINEGQNKPE IEVTWAKQGR TERLCSQNPP VLKRHQREIT RTTLQSDQEE
1681 IDYDDTISVE MKKEDFDIYD EDENQSPRSF QKKTRHYFIA AVERLWDYGM SSSPHVLRNR
1741 AQSGSVPQFK KVVFQEFTDG SFTQPLYRGE LNEHLGLLGP YIRAEVEDNI MVTFRNQASR
1801 PYSFYSSLIS YEEDQRQGAE PRKNFVKPNE TKTYFWKVQH HMAPTKDEFD CKAWAYFSDV
1861 DLEKDVHSGL IGPLLVCHTN TLNPAHGRQV TVQEFALFFT IFDETKSWYF TENMERNCRA
1921 PCNIQMEDPT FKENYRFHAI NGYIMDTLPG LVMAQDQRIR WYLLSMGSNE NIHSIHFSGH
1981 VFTVRKKEEY KMALYNLYPG VFETVEMLPS KAGIWRVECL IGEHLHAGMS TLFLVYSNKC
2041 QTPLGMASGH IRDFQITASG QYGQWAPKLA RLHYSGSINA WSTKEPFSWI KVDLLAPMII
2101 HGIKTQGARQ KFSSLYISQF IIMYSLDGKK WQTYRGNSTG TLMVFFGNVD SSGIKHNIFN
2161 PPIIARYIRL HPTHYSIRST LRMELMGCDL NSCSMPLGME SKAISDAQIT ASSYFTNMFA
2221 TWSPSKARLH LQGRSNAWRP QVNNPKEWLQ VDFQKTMKVT GVTTQGVKSL LTSMYVKEFL
2281 ISSSQDGHQW TLFFQNGKVK VFQGNQDSFT PVVNSLDPPL LTRYLRIHPQ SWVHQIALRM
2341 EVLGCEAQDL Y
```

Figure 7

BDD-FVIII (SEQD ID NO. 3):

```
  A   T   R   R   Y   Y   L   G   A   V   E   L   S   W   D   Y   M   Q    18
 GCC ACC AGA AGA TAC TAC CTG GGT GCA GTG GAA CTG TCA TGG GAC TAT ATG CAA    54

S   D   L   G   E   L   P   V   D   A   R   F   P   P   R   V   P   K    36
 AGT GAT CTC GGT GAG CTG CCT GTG GAC GCA AGA TTT CCT CCT AGA GTG CCA AAA   108

S   F   P   F   N   T   S   V   V   Y   K   K   T   L   F   V   E   F    54
 TCT TTT CCA TTC AAC ACC TCA GTC GTG TAC AAA AAG ACT CTG TTT GTA GAA TTC   162

T   V   H   L   F   N   I   A   K   P   R   P   P   W   M   G   L   L    72
 ACG GTT CAC CTT TTC AAC ATC GCT AAG CCA AGG CCA CCC TGG ATG GGT CTG CTA   216

G   P   T   I   Q   A   E   V   Y   D   T   V   V   I   T   L   K   N    90
 GGT CCT ACC ATC CAG GCT GAG GTT TAT GAT ACA GTG GTC ATT ACA CTT AAG AAC   270

M   A   S   H   P   V   S   L   H   A   V   G   V   S   Y   W   K   A   108
 ATG GCT TCC CAT CCT GTC AGT CTT CAT GCT GTT GGT GTA TCC TAC TGG AAA GCT   324

S   E   G   A   E   Y   D   D   Q   T   S   Q   R   E   K   E   D   D   126
 TCT GAG GGA GCT GAA TAT GAT GAT CAG ACC AGT CAA AGG GAG AAA GAA GAT GAT   378

K   V   F   P   G   G   S   H   T   Y   V   W   Q   V   L   K   E   N   144
 AAA GTC TTC CCT GGT GGA AGC CAT ACA TAT GTC TGG CAG GTC CTG AAA GAG AAT   432

G   P   M   A   S   D   P   L   C   L   T   Y   S   Y   L   S   H   V   162
 GGT CCA ATG GCC TCT GAC CCA CTG TGC CTT ACC TAC TCA TAT CTT TCT CAT GTG   486

D   L   V   K   D   L   N   S   G   L   I   G   A   L   L   V   C   R   180
 GAC CTG GTA AAA GAC TTG AAT TCA GGC CTC ATT GGA GCC CTA CTA GTA TGT AGA   540

E   G   S   L   A   K   E   K   T   Q   T   L   H   K   F   I   L   L   198
 GAA GGG AGT CTG GCC AAG GAA AAG ACA CAG ACC TTG CAC AAA TTT ATA CTA CTT   594

F   A   V   F   D   E   G   K   S   W   H   S   E   T   K   N   S   L   216
 TTT GCT GTA TTT GAT GAA GGG AAA AGT TGG CAC TCA GAA ACA AAG AAC TCC TTG   648

M   Q   D   R   D   A   A   S   A   R   A   W   P   K   M   H   T   V   234
 ATG CAG GAT AGG GAT GCT GCA TCT GCT CGG GCC TGG CCT AAA ATG CAC ACA GTC   702

N   G   Y   V   N   R   S   L   P   G   L   I   G   C   H   R   K   S   252
 AAT GGT TAT GTA AAC AGG TCT CTG CCA GGT CTG ATT GGA TGC CAC AGG AAA TCA   756

V   Y   W   H   V   I   G   M   G   T   T   P   E   V   H   S   I   F   270
 GTC TAT TGG CAT GTG ATT GGA ATG GGC ACC ACT CCT GAA GTG CAC TCA ATA TTC   810

L   E   G   H   T   F   L   V   R   N   H   R   Q   A   S   L   E   I   288
 CTC GAA GGT CAC ACA TTT CTT GTG AGG AAC CAT CGC CAG GCG TCC TTG GAA ATC   864

S   P   I   T   F   L   T   A   Q   T   L   L   M   D   L   G   Q   F   306
 TCG CCA ATA ACT TTC CTT ACT GCT CAA ACA CTC TTG ATG GAC CTT GGA CAG TTT   918

L   L   F   C   H   I   S   S   H   Q   H   D   G   M   E   A   Y   V   324
 CTA CTG TTT TGT CAT ATC TCT TCC CAC CAA CAT GAT GGC ATG GAA GCT TAT GTC   972

K   V   D   S   C   P   E   E   P   Q   L   R   M   K   N   N   E   E   342
 AAA GTA GAC AGC TGT CCA GAG GAA CCC CAA CTA CGA ATG AAA AAT AAT GAA GAA  1026

A   E   D   Y   D   D   D   L   T   D   S   E   M   D   V   V   R   F   360
 GCG GAA GAC TAT GAT GAT GAT CTT ACT GAT TCT GAA ATG GAT GTG GTC AGG TTT  1080
```

Figure 7 (Continued)

```
  D   D   D   N   S   P   S   F   I   Q   I   R   S   V   A   K   K   H    378
 GAT GAT GAC AAC TCT CCT TCC TTT ATC CAA ATT CGC TCA GTT GCC AAG AAG CAT   1134

P   K   T   W   V   H   Y   I   A   A   E   E   E   D   W   D   Y   A    396
 CCT AAA ACT TGG GTA CAT TAC ATT GCT GCT GAA GAG GAG GAC TGG GAC TAT GCT   1188

P   L   V   L   A   P   D   D   R   S   Y   K   S   Q   Y   L   N   N    414
 CCC TTA GTC CTC GCC CCC GAT GAC AGA AGT TAT AAA AGT CAA TAT TTG AAC AAT   1242

G   P   Q   R   I   G   R   K   Y   K   K   V   R   F   M   A   Y   T    432
 GGC CCT CAG CGG ATT GGT AGG AAG TAC AAA AAA GTC CGA TTT ATG GCA TAC ACA   1296

D   E   T   F   K   T   R   E   A   I   Q   H   E   S   G   I   L   G    450
 GAT GAA ACC TTT AAG ACT CGT GAA GCT ATT CAG CAT GAA TCA GGA ATC TTG GGA   1350

P   L   L   Y   G   E   V   G   D   T   L   L   I   I   F   K   N   Q    468
 CCT TTA CTT TAT GGG GAA GTT GGA GAC ACA CTG TTG ATT ATA TTT AAG AAT CAA   1404

A   S   R   P   Y   N   I   Y   P   H   G   I   T   D   V   R   P   L    486
 GCA AGC AGA CCA TAT AAC ATC TAC CCT CAC GGA ATC ACT GAT GTC CGT CCT TTG   1458

Y   S   R   R   L   P   K   G   V   K   H   L   K   D   F   P   I   L    504
 TAT TCA AGG AGA TTA CCA AAA GGT GTA AAA CAT TTG AAG GAT TTT CCA ATT CTG   1512

P   G   E   I   F   K   Y   K   W   T   V   T   V   E   D   G   P   T    522
 CCA GGA GAA ATA TTC AAA TAT AAA TGG ACA GTG ACT GTA GAA GAT GGG CCA ACT   1566

K   S   D   P   R   C   L   T   R   Y   Y   S   S   F   V   N   M   E    540
 AAA TCA GAT CCT CGG TGC CTG ACC CGC TAT TAC TCT AGT TTC GTT AAT ATG GAG   1620

R   D   L   A   S   G   L   I   G   P   L   L   I   C   Y   K   E   S    558
 AGA GAT CTA GCT TCA GGA CTC ATT GGC CCT CTC CTC ATC TGC TAC AAA GAA TCT   1674

V   D   Q   R   G   N   Q   I   M   S   D   K   R   N   V   I   L   F    576
 GTA GAT CAA AGA GGA AAC CAG ATA ATG TCA GAC AAG AGG AAT GTC ATC CTG TTT   1728

S   V   F   D   E   N   R   S   W   Y   L   T   E   N   I   Q   R   F    594
 TCT GTA TTT GAT GAG AAC CGA AGC TGG TAC CTC ACA GAG AAT ATA CAA CGC TTT   1782

L   P   N   P   A   G   V   Q   L   E   D   P   E   F   Q   A   S   N    612
 CTC CCC AAT CCA GCT GGA GTG CAG CTT GAG GAT CCA GAG TTC CAA GCC TCC AAC   1836

I   M   H   S   I   N   G   Y   V   F   D   S   L   Q   L   S   V   C    630
 ATC ATG CAC AGC ATC AAT GGC TAT GTT TTT GAT AGT TTG CAG TTG TCA GTT TGT   1890

L   H   E   V   A   Y   W   Y   I   L   S   I   G   A   Q   T   D   F    648
 TTG CAT GAG GTG GCA TAC TGG TAC ATT CTA AGC ATT GGA GCA CAG ACT GAC TTC   1944

L   S   V   F   F   S   G   Y   T   F   K   H   K   M   V   Y   E   D    666
 CTT TCT GTC TTC TTC TCT GGA TAT ACC TTC AAA CAC AAA ATG GTC TAT GAA GAC   1998

T   L   T   L   F   P   F   S   G   E   T   V   F   M   S   M   E   N    684
 ACA CTC ACC CTA TTC CCA TTC TCA GGA GAA ACT GTC TTC ATG TCG ATG GAA AAC   2052

P   G   L   W   I   L   G   C   H   N   S   D   F   R   N   R   G   M    702
 CCA GGT CTA TGG ATT CTG GGG TGC CAC AAC TCA GAC TTT CGG AAC AGA GGC ATG   2106

T   A   L   L   K   V   S   S   C   D   K   N   T   G   D   Y   Y   E    720
 ACC GCC TTA CTG AAG GTT TCT AGT TGT GAC AAG AAC ACT GGT GAT TAT TAC GAG   2160

D   S   Y   E   D   I   S   A   Y   L   L   S   K   N   N   A   I   E    738
 GAC AGT TAT GAA GAT ATT TCA GCA TAC TTG CTG AGT AAA AAC AAT GCC ATT GAA   2214
```

Figure 7 (Continued)

```
  P   R   E   I   T   R   T   T   L   Q   S   D   Q   E   E   I   D   Y    756
CCA AGA GAA ATA ACT CGT ACT ACT CTT CAG TCA GAT CAA GAG GAA ATT GAC TAT   2268

D   D   T   I   S   V   E   M   K   K   E   D   F   D   I   Y   D   E    774
GAT GAT ACC ATA TCA GTT GAA ATG AAG AAG GAA GAT TTT GAC ATT TAT GAT GAG   2322

D   E   N   Q   S   P   R   S   F   Q   K   K   T   R   H   Y   F   I    792
GAT GAA AAT CAG AGC CCC CGC AGC TTT CAA AAG AAA ACA CGA CAC TAT TTT ATT   2376

A   A   V   E   R   L   W   D   Y   G   M   S   S   P   H   V   L    810
GCT GCA GTG GAG AGG CTC TGG GAT TAT GGG ATG AGT AGC TCC CCA CAT GTT CTA   2430

R   N   R   A   Q   S   G   S   V   P   Q   F   K   K   V   V   F   Q    828
AGA AAC AGG GCT CAG AGT GGC AGT GTC CCT CAG TTC AAG AAA GTT GTT TTC CAG   2484

E   F   T   D   G   S   F   T   Q   P   L   Y   R   G   E   L   N   E    846
GAA TTT ACT GAT GGC TCC TTT ACT CAG CCC TTA TAC CGT GGA GAA CTA AAT GAA   2538

H   L   G   L   L   G   P   Y   I   R   A   E   V   E   D   N   I   M    864
CAT TTG GGA CTC CTG GGG CCA TAT ATA AGA GCA GAA GTT GAA GAT AAT ATC ATG   2592

V   T   F   R   N   Q   A   S   R   P   Y   S   F   Y   S   S   L   I    882
GTA ACT TTC AGA AAT CAG GCC TCT CGT CCC TAT TCC TTC TAT TCT AGC CTT ATT   2646

S   Y   E   E   D   Q   R   Q   G   A   E   P   R   K   N   F   V   K    900
TCT TAT GAG GAA GAT CAG AGG CAA GGA GCA GAA CCT AGA AAA AAC TTT GTC AAG   2700

P   N   E   T   K   T   Y   F   W   K   V   Q   H   M   A   P   T    918
CCT AAT GAA ACC AAA ACT TAC TTT TGG AAA GTG CAA CAT CAT ATG GCA CCC ACT   2754

K   D   E   F   D   C   K   A   W   A   Y   F   S   D   V   D   L   E    936
AAA GAT GAG TTT GAC TGC AAA GCC TGG GCT TAT TTC TCT GAT GTT GAC CTG GAA   2808

K   D   V   H   S   G   L   I   G   P   L   L   V   C   H   T   N   T    954
AAA GAT GTG CAC TCA GGC CTG ATT GGA CCC CTT CTG GTC TGC CAC ACT AAC ACA   2862

L   N   P   A   H   G   R   Q   V   T   V   Q   E   F   A   L   F   F    972
CTG AAC CCT GCT CAT GGG AGA CAA GTG ACA GTA CAG GAA TTT GCT CTG TTT TTC   2916

T   I   F   D   E   T   K   S   W   Y   F   T   E   N   M   E   R   N    990
ACC ATC TTT GAT GAG ACC AAA AGC TGG TAC TTC ACT GAA AAT ATG GAA AGA AAC   2970

C   R   A   P   C   N   I   Q   M   E   D   P   T   F   K   E   N   Y   1008
TGC AGG GCT CCC TGC AAT ATC CAG ATG GAA GAT CCC ACT TTT AAA GAG AAT TAT   3024

R   F   H   A   I   N   G   Y   I   M   D   T   L   P   G   L   V   M   1026
CGC TTC CAT GCA ATC AAT GGC TAC ATA ATG GAT ACA CTA CCT GGC TTA GTA ATG   3078

A   Q   D   Q   R   I   R   W   Y   L   L   S   M   G   S   N   E   N   1044
GCT CAG GAT CAA AGG ATT CGA TGG TAT CTG CTC AGC ATG GGC AGC AAT GAA AAC   3132

I   H   S   I   H   F   S   G   H   V   F   T   V   R   K   K   E   E   1062
ATC CAT TCT ATT CAT TTC AGT GGA CAT GTG TTC ACT GTA CGA AAA AAA GAG GAG   3186

Y   K   M   A   L   Y   N   L   Y   P   G   V   F   E   T   V   E   M   1080
TAT AAA ATG GCA CTG TAC AAT CTC TAT CCA GGT GTT TTT GAG ACA GTG GAA ATG   3240

L   P   S   K   A   G   I   W   R   V   E   C   L   I   G   E   H   L   1098
TTA CCA TCC AAA GCT GGA ATT TGG CGG GTG GAA TGC CTT ATT GGC GAG CAT CTA   3294

H   A   G   M   S   T   L   F   L   V   Y   S   N   K   C   Q   T   P   1116
CAT GCT GGG ATG AGC ACA CTT TTT CTG GTG TAC AGC AAT AAG TGT CAG ACT CCC   3348
```

Figure 7 (Continued)

```
  L   G   M   A   S   G   H   I   R   D   F   Q   I   T   A   S   G   Q   1134
CTG GGA ATG GCT TCT GGA CAC ATT AGA GAT TTT CAG ATT ACA GCT TCA GGA CAA 3402

Y   G   Q   W   A   P   K   L   A   R   L   H   Y   S   G   S   I   N   1152
TAT GGA CAG TGG GCC CCA AAG CTG GCC AGA CTT CAT TAT TCC GGA TCA ATC AAT 3456

A   W   S   T   K   E   P   F   S   W   I   K   V   D   L   L   A   P   1170
GCC TGG AGC ACC AAG GAG CCC TTT TCT TGG ATC AAG GTG GAT CTG TTG GCA CCA 3510

M   I   I   H   G   I   K   T   Q   G   A   R   Q   K   F   S   S   L   1188
ATG ATT ATT CAC GGC ATC AAG ACC CAG GGT GCC CGT CAG AAG TTC TCC AGC CTC 3564

Y   I   S   Q   F   I   I   M   Y   S   L   D   G   K   K   W   Q   T   1206
TAC ATC TCT CAG TTT ATC ATC ATG TAT AGT CTT GAT GGG AAG AAG TGG CAG ACT 3618

Y   R   G   N   S   T   G   T   L   M   V   F   F   G   N   V   D   S   1224
TAT CGA GGA AAT TCC ACT GGA ACC TTA ATG GTC TTC TTT GGC AAT GTG GAT TCA 3672

S   G   I   K   H   N   I   F   N   P   P   I   I   A   R   Y   I   R   1242
TCT GGG ATA AAA CAC AAT ATT TTT AAC CCT CCA ATT ATT GCT CGA TAC ATC CGT 3726

L   H   P   T   H   Y   S   I   R   S   T   L   R   M   E   L   M   G   1260
TTG CAC CCA ACT CAT TAT AGC ATT CGC AGC ACT CTT CGC ATG GAG TTG ATG GGC 3780

C   D   L   N   S   C   S   M   P   L   G   M   E   S   K   A   I   S   1278
TGT GAT TTA AAT AGT TGC AGC ATG CCA TTG GGA ATG GAG AGT AAA GCA ATA TCA 3834

D   A   Q   I   T   A   S   S   Y   F   T   N   M   F   A   T   W   S   1296
GAT GCA CAG ATT ACT GCT TCA TCC TAC TTT ACC AAT ATG TTT GCC ACC TGG TCT 3888

P   S   K   A   R   L   H   L   Q   G   R   S   N   A   W   R   P   Q   1314
CCT TCA AAA GCT CGA CTT CAC CTC CAA GGG AGG AGT AAT GCC TGG AGA CCT CAG 3942

V   N   N   P   K   E   W   L   Q   V   D   F   Q   K   T   M   K   V   1332
GTG AAT AAT CCA AAA GAG TGG CTG CAA GTG GAC TTC CAG AAG ACA ATG AAA GTC 3996

T   G   V   T   T   Q   G   V   K   S   L   L   T   S   M   Y   V   K   1350
ACA GGA GTA ACT ACT CAG GGA GTA AAA TCT CTG CTT ACC AGC ATG TAT GTG AAG 4050

E   F   L   I   S   S   S   Q   D   G   H   Q   W   T   L   F   F   Q   1368
GAG TTC CTC ATC TCC AGC AGT CAA GAT GGC CAT CAG TGG ACT CTC TTT TTT CAG 4104

N   G   K   V   K   V   F   Q   G   N   Q   D   S   F   T   P   V   V   1386
AAT GGC AAA GTA AAG GTT TTT CAG GGA AAT CAA GAC TCC TTC ACA CCT GTG GTG 4158

N   S   L   D   P   P   L   L   T   R   Y   L   R   I   H   P   Q   S   1404
AAC TCT CTA GAC CCA CCG TTA CTG ACT CGC TAC CTT CGA ATT CAC CCC CAG AGT 4212

W   V   H   Q   I   A   L   R   M   E   V   L   G   C   E   A   Q   D   1422
TGG GTG CAC CAG ATT GCC CTG AGG ATG GAG GTT CTG GGC TGC GAG GCA CAG GAC 4266

L   Y   *                                                               1425
CTC TAC TGA                                                               4275
```

Figure 8

HC FVIII (A1a1A2a2) Asn239Ala:

```
  A   T   R   R   Y   Y   L   G   A   V   E   L   S   W   D   Y   M   Q    18
GCC ACC AGA AGA TAC TAC CTG GGT GCA GTG GAA CTG TCA TGG GAC TAT ATG CAA    54

S   D   L   G   E   L   P   V   D   A   R   F   P   P   R   V   P   K    36
AGT GAT CTC GGT GAG CTG CCT GTG GAC GCA AGA TTT CCT CCT AGA GTG CCA AAA   108

S   F   P   F   N   T   S   V   V   Y   K   K   T   L   F   V   E   F    54
TCT TTT CCA TTC AAC ACC TCA GTC GTG TAC AAA AAG ACT CTG TTT GTA GAA TTC   162

T   V   H   L   F   N   I   A   K   P   R   P   P   W   M   G   L   L    72
ACG GTT CAC CTT TTC AAC ATC GCT AAG CCA AGG CCA CCC TGG ATG GGT CTG CTA   216

G   P   T   I   Q   A   E   V   Y   D   T   V   V   I   T   L   K   N    90
GGT CCT ACC ATC CAG GCT GAG GTT TAT GAT ACA GTG GTC ATT ACA CTT AAG AAC   270

M   A   S   H   P   V   S   L   H   A   V   G   V   S   Y   W   K   A   108
ATG GCT TCC CAT CCT GTC AGT CTT CAT GCT GTT GGT GTA TCC TAC TGG AAA GCT   324

S   E   G   A   E   Y   D   D   Q   T   S   Q   R   E   K   E   D   D   126
TCT GAG GGA GCT GAA TAT GAT GAT CAG ACC AGT CAA AGG GAG AAA GAA GAT GAT   378

K   V   F   P   G   G   S   H   T   Y   V   W   Q   V   L   K   E   N   144
AAA GTC TTC CCT GGT GGA AGC CAT ACA TAT GTC TGG CAG GTC CTG AAA GAG AAT   432

G   P   M   A   S   D   P   L   C   L   T   Y   S   Y   L   S   H   V   162
GGT CCA ATG GCC TCT GAC CCA CTG TGC CTT ACC TAC TCA TAT CTT TCT CAT GTG   486

D   L   V   K   D   L   N   S   G   L   I   G   A   L   L   V   C   R   180
GAC CTG GTA AAA GAC TTG AAT TCA GGC CTC ATT GGA GCC CTA CTA GTA TGT AGA   540

E   G   S   L   A   K   E   K   T   Q   T   L   H   K   F   I   L   L   198
GAA GGG AGT CTG GCC AAG GAA AAG ACA CAG ACC TTG CAC AAA TTT ATA CTA CTT   594

F   A   V   F   D   E   G   K   S   W   H   S   E   T   K   N   S   L   216
TTT GCT GTA TTT GAT GAA GGG AAA AGT TGG CAC TCA GAA ACA AAG AAC TCC TTG   648

M   Q   D   R   D   A   A   S   A   R   A   W   P   K   M   H   T   V   234
ATG CAG GAT AGG GAT GCT GCA TCT GCT CGG GCC TGG CCT AAA ATG CAC ACA GTC   702

N   G   Y   V   A   R   S   L   P   G   L   I   G   C   H   R   K   S   252
AAT GGT TAT GTA GCC AGG TCT CTG CCA GGT CTG ATT GGA TGC CAC AGG AAA TCA   756

V   Y   W   H   V   I   G   M   G   T   T   P   E   V   H   S   I   F   270
GTC TAT TGG CAT GTG ATT GGA ATG GGC ACC ACT CCT GAA GTG CAC TCA ATA TTC   810

L   E   G   H   T   F   L   V   R   N   H   R   Q   A   S   L   E   I   288
CTC GAA GGT CAC ACA TTT CTT GTG AGG AAC CAT CGC CAG GCG TCC TTG GAA ATC   864

S   P   I   T   F   L   T   A   Q   T   L   L   M   D   L   G   Q   F   306
TCG CCA ATA ACT TTC CTT ACT GCT CAA ACA CTC TTG ATG GAC CTT GGA CAG TTT   918

L   L   F   C   H   I   S   S   H   Q   H   D   G   M   E   A   Y   V   324
CTA CTG TTT TGT CAT ATC TCT TCC CAC CAA CAT GAT GGC ATG GAA GCT TAT GTC   972

K   V   D   S   C   P   E   E   P   Q   L   R   M   K   N   N   E   E   342
AAA GTA GAC AGC TGT CCA GAG GAA CCC CAA CTA CGA ATG AAA AAT AAT GAA GAA  1026

A   E   D   Y   D   D   D   L   T   D   S   E   M   D   V   V   R   F   360
GCG GAA GAC TAT GAT GAT GAT CTT ACT GAT TCT GAA ATG GAT GTG GTC AGG TTT  1080
```

Figure 8 (Continued)

```
      D   D   D   N   S   P   S   F   I   Q   I   R   S   V   A   K   K   H    378
     GAT GAT GAC AAC TCT CCT TCC TTT ATC CAA ATT CGC TCA GTT GCC AAG AAG CAT   1134

P   K   T   W   V   H   Y   I   A   A   E   E   E   D   W   D   Y   A    396
     CCT AAA ACT TGG GTA CAT TAC ATT GCT GCT GAA GAG GAG GAC TGG GAC TAT GCT   1188

P   L   V   L   A   P   D   D   R   S   Y   K   S   Q   Y   L   N   N    414
     CCC TTA GTC CTC GCC CCC GAT GAC AGA AGT TAT AAA AGT CAA TAT TTG AAC AAT   1242

G   P   Q   R   I   G   R   K   Y   K   K   V   R   F   M   A   Y   T    432
     GGC CCT CAG CGG ATT GGT AGG AAG TAC AAA AAA GTC CGA TTT ATG GCA TAC ACA   1296

D   E   T   F   K   T   R   E   A   I   Q   H   E   S   G   I   L   G    450
     GAT GAA ACC TTT AAG ACT CGT GAA GCT ATT CAG CAT GAA TCA GGA ATC TTG GGA   1350

P   L   L   Y   G   E   V   G   D   T   L   L   I   I   F   K   N   Q    468
     CCT TTA CTT TAT GGG GAA GTT GGA GAC ACA CTG TTG ATT ATA TTT AAG AAT CAA   1404

A   S   R   P   Y   N   I   Y   P   H   G   I   T   D   V   R   P   L    486
     GCA AGC AGA CCA TAT AAC ATC TAC CCT CAC GGA ATC ACT GAT GTC CGT CCT TTG   1458

Y   S   R   R   L   P   K   G   V   K   H   L   K   D   F   P   I   L    504
     TAT TCA AGG AGA TTA CCA AAA GGT GTA AAA CAT TTG AAG GAT TTT CCA ATT CTG   1512

P   G   E   I   F   K   Y   K   W   T   V   T   V   E   D   G   P   T    522
     CCA GGA GAA ATA TTC AAA TAT AAA TGG ACA GTG ACT GTA GAA GAT GGG CCA ACT   1566

K   S   D   P   R   C   L   T   R   Y   Y   S   S   F   V   N   M   E    540
     AAA TCA GAT CCT CGG TGC CTG ACC CGC TAT TAC TCT AGT TTC GTT AAT ATG GAG   1620

R   D   L   A   S   G   L   I   G   P   L   L   I   C   Y   K   E   S    558
     AGA GAT CTA GCT TCA GGA CTC ATT GGC CCT CTC CTC ATC TGC TAC AAA GAA TCT   1674

V   D   Q   R   G   N   Q   I   M   S   D   K   R   N   V   I   L   F    576
     GTA GAT CAA AGA GGA AAC CAG ATA ATG TCA GAC AAG AGG AAT GTC ATC CTG TTT   1728

S   V   F   D   E   N   R   S   W   Y   L   T   E   N   I   Q   R   F    594
     TCT GTA TTT GAT GAG AAC CGA AGC TGG TAC CTC ACA GAG AAT ATA CAA CGC TTT   1782

L   P   N   P   A   G   V   Q   L   E   D   P   E   F   Q   A   S   N    612
     CTC CCC AAT CCA GCT GGA GTG CAG CTT GAG GAT CCA GAG TTC CAA GCC TCC AAC   1836

I   M   H   S   I   N   G   Y   V   F   D   S   L   Q   L   S   V   C    630
     ATC ATG CAC AGC ATC AAT GGC TAT GTT TTT GAT AGT TTG CAG TTG TCA GTT TGT   1890

L   H   E   V   A   Y   W   Y   I   L   S   I   G   A   Q   T   D   F    648
     TTG CAT GAG GTG GCA TAC TGG TAC ATT CTA AGC ATT GGA GCA CAG ACT GAC TTC   1944

L   S   V   F   F   S   G   Y   T   F   K   H   K   M   V   Y   E   D    666
     CTT TCT GTC TTC TTC TCT GGA TAT ACC TTC AAA CAC AAA ATG GTC TAT GAA GAC   1998

T   L   T   L   F   P   F   S   G   E   T   V   F   M   S   M   E   N    684
     ACA CTC ACC CTA TTC CCA TTC TCA GGA GAA ACT GTC TTC ATG TCG ATG GAA AAC   2052

P   G   L   W   I   L   G   C   H   N   S   D   F   R   N   R   G   M    702
     CCA GGT CTA TGG ATT CTG GGG TGC CAC AAC TCA GAC TTT CGG AAC AGA GGC ATG   2106

T   A   L   L   K   V   S   S   C   D   K   N   T   G   D   Y   Y   E    720
     ACC GCC TTA CTG AAG GTT TCT AGT TGT GAC AAG AAC ACT GGT GAT TAT TAC GAG   2160

D   S   Y   E   D   I   S   A   Y   L   L   S   K   N   N   A   I   E    738
     GAC AGT TAT GAA GAT ATT TCA GCA TAC TTG CTG AGT AAA AAC AAT GCC ATT GAA   2214

P   R
     CCA AGA
```

Figure 9

LC FVIII (A3C1C2) Asn2118Ala:

```
      S   F   Q   K   K   T   R   H   Y   F   I   A   A   V   E   R   L   W       18
    AGC TTT CAA AAG AAA ACA CGA CAC TAT TTT ATT GCT GCA GTG GAG AGG CTC TGG        54

D   Y   G   M   S   S   S   P   H   V   L   R   N   R   A   Q   S   G       36
    GAT TAT GGG ATG AGT AGC TCC CCA CAT GTT CTA AGA AAC AGG GCT CAG AGT GGC       108

S   V   P   Q   F   K   K   V   V   F   Q   E   F   T   D   G   S   F       54
    AGT GTC CCT CAG TTC AAG AAA GTT GTT TTC CAG GAA TTT ACT GAT GGC TCC TTT       162

T   Q   P   L   Y   R   G   E   L   N   E   H   L   G   L   L   G   P       72
    ACT CAG CCC TTA TAC CGT GGA GAA CTA AAT GAA CAT TTG GGA CTC CTG GGG CCA       216

Y   I   R   A   E   V   E   D   N   I   M   V   T   F   R   N   Q   A       90
    TAT ATA AGA GCA GAA GTT GAA GAT AAT ATC ATG GTA ACT TTC AGA AAT CAG GCC       270

S   R   P   Y   S   F   Y   S   S   L   I   S   Y   E   E   D   Q   R      108
    TCT CGT CCC TAT TCC TTC TAT TCT AGC CTT ATT TCT TAT GAG GAA GAT CAG AGG       324

Q   G   A   E   P   R   K   N   F   V   K   P   N   E   T   K   T   Y      126
    CAA GGA GCA GAA CCT AGA AAA AAC TTT GTC AAG CCT AAT GAA ACC AAA ACT TAC       378

F   W   K   V   Q   H   H   M   A   P   T   K   D   E   F   D   C   K      144
    TTT TGG AAA GTG CAA CAT CAT ATG GCA CCC ACT AAA GAT GAG TTT GAC TGC AAA       432

A   W   A   Y   F   S   D   V   D   L   E   K   D   V   H   S   G   L      162
    GCC TGG GCT TAT TTC TCT GAT GTT GAC CTG GAA AAA GAT GTG CAC TCA GGC CTG       486

I   G   P   L   L   V   C   H   T   N   T   L   N   P   A   H   G   R      180
    ATT GGA CCC CTT CTG GTC TGC CAC ACT AAC ACA CTG AAC CCT GCT CAT GGG AGA       540

Q   V   T   V   Q   E   F   A   L   F   F   T   I   F   D   E   T   K      198
    CAA GTG ACA GTA CAG GAA TTT GCT CTG TTT TTC ACC ATC TTT GAT GAG ACC AAA       594

S   W   Y   F   T   E   N   M   E   R   N   C   R   A   P   C   N   I      216
    AGC TGG TAC TTC ACT GAA AAT ATG GAA AGA AAC TGC AGG GCT CCC TGC AAT ATC       648

Q   M   E   D   P   T   F   K   E   N   Y   R   F   H   A   I   N   G      234
    CAG ATG GAA GAT CCC ACT TTT AAA GAG AAT TAT CGC TTC CAT GCA ATC AAT GGC       702

Y   I   M   D   T   L   P   G   L   V   M   A   Q   D   Q   R   I   R      252
    TAC ATA ATG GAT ACA CTA CCT GGC TTA GTA ATG GCT CAG GAT CAA AGG ATT CGA       756

W   Y   L   L   S   M   G   S   N   E   N   I   H   S   I   H   F   S      270
    TGG TAT CTG CTC AGC ATG GGC AGC AAT GAA AAC ATC CAT TCT ATT CAT TTC AGT       810

G   H   V   F   T   V   R   K   K   E   E   Y   K   M   A   L   Y   N      288
    GGA CAT GTG TTC ACT GTA CGA AAA AAG GAG GAG TAT AAA ATG GCA CTG TAC AAT       864

L   Y   P   G   V   F   E   T   V   E   M   L   P   S   K   A   G   I      306
    CTC TAT CCA GGT GTT TTT GAG ACA GTG GAA ATG TTA CCA TCC AAA GCT GGA ATT       918

W   R   V   E   C   L   I   G   E   H   L   H   A   G   M   S   T   L      324
    TGG CGG GTG GAA TGC CTT ATT GGC GAG CAT CTA CAT GCT GGG ATG AGC ACA CTT       972

F   L   V   Y   S   N   K   C   Q   T   P   L   G   M   A   S   G   H      342
    TTT CTG GTG TAC AGC AAT AAG TGT CAG ACT CCC CTG GGA ATG GCT TCT GGA CAC      1026

I   R   D   F   Q   I   T   A   S   G   Q   Y   G   Q   W   A   P   K      360
    ATT AGA GAT TTT CAG ATT ACA GCT TCA GGA CAA TAT GGA CAG TGG GCC CCA AAG      1080
```

Figure 9 (Continued)

```
  L   A   R   L   H   Y   S   G   S   I   N   A   W   S   T   K   E   P    378
CTG GCC AGA CTT CAT TAT TCC GGA TCA ATC AAT GCC TGG AGC ACC AAG GAG CCC    1134

F   S   W   I   K   V   D   L   L   A   P   M   I   I   H   G   I   K    396
TTT TCT TGG ATC AAG GTG GAT CTG TTG GCA CCA ATG ATT ATT CAC GGC ATC AAG    1188

T   Q   G   A   R   Q   K   F   S   S   L   Y   I   S   Q   F   I   I    414
ACC CAG GGT GCC CGT CAG AAG TTC TCC AGC CTC TAC ATC TCT CAG TTT ATC ATC    1242

M   Y   S   L   D   G   K   K   W   Q   T   Y   R   G   A   S   T   G    432
ATG TAT AGT CTT GAT GGG AAG AAG TGG CAG ACT TAT CGA GGA GCC TCC ACT GGA    1296

T   L   M   V   F   F   G   N   V   D   S   S   G   I   K   H   N   I    450
ACC TTA ATG GTC TTC TTT GGC AAT GTG GAT TCA TCT GGG ATA AAA CAC AAT ATT    1350

F   N   P   P   I   I   A   R   Y   I   R   L   H   P   T   H   Y   S    468
TTT AAC CCT CCA ATT ATT GCT CGA TAC ATC CGT TTG CAC CCA ACT CAT TAT AGC    1404

I   R   S   T   L   R   M   E   L   M   G   C   D   L   N   S   C   S    486
ATT CGC AGC ACT CTT CGC ATG GAG TTG ATG GGC TGT GAT TTA AAT AGT TGC AGC    1458

M   P   L   G   M   E   S   K   A   I   S   D   A   Q   I   T   A   S    504
ATG CCA TTG GGA ATG GAG AGT AAA GCA ATA TCA GAT GCA CAG ATT ACT GCT TCA    1512

S   Y   F   T   N   M   F   A   T   W   S   P   S   K   A   R   L   H    522
TCC TAC TTT ACC AAT ATG TTT GCC ACC TGG TCT CCT TCA AAA GCT CGA CTT CAC    1566

L   Q   G   R   S   N   A   W   R   P   Q   V   N   N   P   K   E   W    540
CTC CAA GGG AGG AGT AAT GCC TGG AGA CCT CAG GTG AAT AAT CCA AAA GAG TGG    1620

L   Q   V   D   F   Q   K   T   M   K   V   T   G   V   T   T   Q   G    558
CTG CAA GTG GAC TTC CAG AAG ACA ATG AAA GTC ACA GGA GTA ACT ACT CAG GGA    1674

V   K   S   L   L   T   S   M   Y   V   K   E   F   L   I   S   S   S    576
GTA AAA TCT CTG CTT ACC AGC ATG TAT GTG AAG GAG TTC CTC ATC TCC AGC AGT    1728

Q   D   G   H   Q   W   T   L   F   F   Q   N   G   K   V   K   V   F    594
CAA GAT GGC CAT CAG TGG ACT CTC TTT TTT CAG AAT GGC AAA GTA AAG GTT TTT    1782

Q   G   N   Q   D   S   F   T   P   V   V   N   S   L   D   P   P   L    612
CAG GGA AAT CAA GAC TCC TTC ACA CCT GTG GTG AAC TCT CTA GAC CCA CCG TTA    1836

L   T   R   Y   L   R   I   H   P   Q   S   W   V   H   Q   I   A   L    630
CTG ACT CGC TAC CTT CGA ATT CAC CCC CAG AGT TGG GTG CAC CAG ATT GCC CTG    1890

R   M   E   V   L   G   C   E   A   Q   D   L   Y   *                    644
AGG ATG GAG GTT CTG GGC TGC GAG GCA CAG GAC CTC TAC TGA                    1932
```

DEMANNOSYLATED RECOMBINANT FACTOR VIII FOR THE TREATMENT OF PATIENTS WITH HAEMOPHILIA A

TECHNICAL FIELD

The present invention relates to a substantially non-immunogenic or less immunogenic modified Factor VIII. The invention further relates to nucleic acid constructs including DNA encoding the modified FVIII, as well as to methods for expressing and producing the modified FVIII in a host cell or in an organism. The invention also relates to methods of administrating the modified FVIII to a subject to treat a bleeding disorder.

BACKGROUND ART

Human factor VIII:C (FVIII) is the coagulation factor deficient in the X-chromosome-linked bleeding disorder hemophilia A, a major source of hemorrhagic morbidity and mortality in affected males. Traditionally, hemophiliacs were treated with transfusions of whole blood. More recently, treatment has been with preparations of FVIII concentrates derived from human plasma. However, the use of plasma-derived product exposes hemophiliac patients to the possible risk of virus-transmissible diseases such as hepatitis and AIDS. Costly purification schemes to reduce this risk increase treatment costs. With increase in costs and limited availability of plasma-derived FVIII, patients are treated episodically on a demand basis rather than prophylactically. Recombinantly produced FVIII has substantial advantages over plasma-derived FVIII in terms of purity and safety, as well as increased availability and accordingly, much research effort has been directed towards the development of recombinantly produced FVIII. Due to the labile nature of FVIII, especially following its activation, large and repeated doses of protein whether plasma or recombinantly-derived, must be administered to achieve a therapeutic benefit. However, the amount of FVIII protein the patient is exposed to has been correlated with the development of antibodies which inhibit its activity. In light of this known immunogenicity, one of the goals in developing new recombinant forms of FVIII for use as a therapeutic agent is the development of products that reduce or eliminate such an immune response. FVIII functions in the intrinsic pathway of blood coagulation as a cofactor to accelerate the activation of factor X by factor IXa, a reaction that occurs on a negatively charged phospholipid surface in the presence of calcium ions.

The FVIII molecule is divided into 6 structural domains: a triplicated A domain (A1, A2, A3), a carbohydrate-rich and dispensable central domain (B-domain), and a duplicated C domain (C1, C2) (see FIG. 5). FVIII is secreted into plasma as a heterodimer of a heavy chain (domains A1-A2-B) and a light chain (domains A3-C1-C2) associated through a noncovalent divalent metal ion linkage between the A1- and A3-domains. In plasma, FVIII is stabilized by binding to von Willebrand factor. More specifically, the FVIII light chain is bound by noncovalent interactions to a primary binding site in the amino terminus of von Willebrand factor. Upon proteolytic activation by thrombin, FVIII is activated to a heterotrimer of 2 heavy chain fragments (A1, a 50 kDa fragment, and A2, a 43 kDa fragment) and the light chain (A3-C1-C2, a 73 kDa chain). The active form of FVIII (FVIIIa) thus consists of an A1-subunit associated through the divalent metal ion linkage to a thrombin-cleaved A3-C1-C2 light chain and a free A2 subunit associated with the A1 domain through an ion association. This FVIIIa heterotrimer is unstable and subject to rapid inactivation through dissociation of the A2 subunit under physiological conditions. The FVIII molecule contains 25 consensus sequences (Asn-Xxx-Thr/Ser) that allow N-linked glycosylation, of which 20 have been shown to be glycosylated (1).

FVIII protein may be functionally defined as a factor capable of supplementing the coagulation defect in plasma derived from patients affected by haemophilia A. In order to allow the treatment of haemophilia A, FVIII has been purified from human or porcine plasma and more recently produced by recombinant DNA technologies. U.S. Pat. No. 4,965,199 discloses, for example, methods developed for the recombinant production of therapeutic quantities of FVIII in mammalian host cells. Human FVIII expression in CHO (Chinese hamster ovary) cells and BHKC (baby hamster kidney cells) has also been reported and, more recently, the efficacy of B-domain deleted FVIII has been demonstrated in clinical trials (U.S. Pat. No. 4,868,112, ref 2).

Commercially available therapeutic FVIII products include plasma derived FVIII (pdFVIII) and recombinant FVIII (rFVIII) products, such as the full-length rFVIII (Kogenate® Bayer, Advate® Baxter, Helixate® CSL-Behring) and a B-domain deleted rFVIII (Refacto® Wyeth).

However, despite the availability of therapeutic grade FVIII, the need for FVIII analogues with enhanced properties remains high. Indeed, treatment of hemophilia A patients with therapeutic FVIII (pdFVIII or rFVIII) results, in 15 to 30% of the cases, in the emergence of anti-FVIII antibodies (inhibitors) which neutralize the pro-coagulant activity of the therapeutically administered FVIII (3,4). The occurrence of inhibitors is considered to reflect an allogeneic immune response to the repeated administration of an exogenous FVIII protein. Some haemophiliacs are extremely sensitive to exogenous recombinant factor VIII and develop anti-factor VIII antibodies limiting the effectiveness of their treatment. Therefore, the development of FVIII inhibitors represents both a major medical hurdle and a critical societal concern since patients producing FVIII inhibitors become resistant to conventional replacement therapy. FVIII inhibitor occurrence not only results in a 3 folds increase of the treatment costs (5), but it also dramatically affects the quality of life of the patients, increasing morbidity and mortality. In this regard, it is highly desired to provide FVIII with reduced or absent potential to induce an immune response in the human subject. In addition, it is highly desired to provide FVIII with an increased circulation time within the human subject that would be of particular benefit in the chronic and recurring disease setting such as is the case hemophilia A.

The first step of the FVIII-directed specific immune response was shown to consist in the endocytosis of FVIII by Antigen Presenting Cells (APCs). Dendritic cells (DCs) have been suggested to be the most potent APC for priming of naïve T cells and initiation of the corresponding antigen-specific immune response (6,7). Antigen endocytosis by DCs is generally performed by macropinocytosis or by receptor-mediated endocytosis. Indeed, the DC surface presents a myriad of endocytic receptors most of which are dependent on the presence of bivalent ions, mainly calcium. Many endocytic receptors, by virtue of their exposed carbohydrate recognition domains (CRDs), are specific for sugar residues present on the antigens (8), and are referred to as C type lectin receptors (CLRs). Mannose residues on an antigen can thus be recognized by a series of mannose sensitive CLRs on DC surface, that include the mannose receptor (MR, CD206), dendritic cell specific ICAM3 grabbing nonintegrin (DC-SIGN, CD209), dectin, DEC-205 (CD205). The polycarbohydrate mannan has been shown to be a ligand for these mannose sensitive CLRs especially for MR and DC-SIGN (9-11). DC-SIGN molecule on DCs fixes the ICAM-3 on T-cells. This specific interaction seems to play a major role in the initiation of the immunological synapse between DCs and T-cells. The activation of lymphocytes might therefore be inhibited with a blocking antibody anti-DC-SIGN.

Several treatments were shown to reduce the consequences of FVIII immune response. For example treatment consisting in the use of desmopressin (a synthetic hormone which stimulate the production of FVIII), coagulation promoter agents (for example prothrombin-complex concentrate or activated prothrombin-complex concentrate), recombinant factor VIIa or perfusion of FVIII in order to induce a tolerance.

A recent method, consisting in the use of anti-idiotypic antibodies, which interact with the variable region of other antibodies, was developed to neutralize the inhibitor antibodies (12). Thus, a IgG4kappa monoclonal human antibody directed against an anti-FVIII C1 domain was isolated, which blocks the cofactor activity of FVIII and its linkage to von Willebrand factor (vWF) (13). Similarly, a human monoclonal antibody anti-FVIII C2 domain, BO2C11 (IgG4kappa) was isolated (14), which inhibits the linkage of FVIII to vWF and phospholipids. This antibody therefore inhibits completely the procoagulant activity of native and activated FVIII. An other example of monoclonal antibody is the BOIIB2, directed against FVIII A2 domain, which blocks 99% of the FVIII activity. However, the FVIII-induced immune response is a polyclonal response, and a treatment consisting in the use of anti-idiotypic antibodies directed against anti-FVIII antibodies could only partially neutralize the FVIII immune response.

The applicant has recently demonstrated that mannose-ending glycosylations on FVIII mediate the internalization of FVIII by immature human dendritic cells (DCs). These results demonstrate that blocking of the interaction between mannosylated sugars located on FVIII and the DCs mannose receptors reduces the internalization of FVIII and the further presentation to FVIII-specific T cells. Reduction of FVIII immunogenicity can thus be achieved by reducing its ability to interact with mannose-sensitive receptors.

The applicant has moreover surprisingly found that the ability of a modified FVIII wherein one or more amino acid selected from asparagin 239 (Asn239) and asparagin 2118 (Asn2118) has/have been substituted or deleted, to activate T cells when presented by DCs is substantially reduced or abolished, leading to provide the opportunity to provide non-immunogenic or less-immunogenic therapeutic FVIII to patients.

SUMMARY OF THE INVENTION

The present invention provides a FVIII protein comprising a modified FVIII polypeptide, and characterised in that the ability of said modified FVIII polypeptide to interact or to be endocyted by endocytosis capable cells is decreased or abolished with respect to the non-modified corresponding FVIII polypeptide.

In a specific embodiment, the present invention provides a modified FVIII polypeptide whose ability to interact with surface receptors from endocytosis capable cells is decreased or abolished, in particular a modified FVIII polypeptide the ability of which is decreased or abolished when surface receptors are mannose sensitive receptors, and more particularly when surface receptors are selected in a group consisting of mannose receptor (MR, CD206), dendritic cell specific ICAM3 grabbing non-integrin (DC-SIGN, CD209), dectin, and DEC-205 (CD205). In a specific embodiment, endocytosis capable cells are Antigen Presenting Cells (APCs), and, particularly, Dendritic Cells, Macrophages, endothelial cells or B Lymphocyte cells.

In an other specific embodiment, the present invention provides a modified FVIII polypeptide, the immunogenicity of which is substantially reduced or abolished in human.

In an other aspect, the modified FVIII polypeptide of the invention is substantially deglycosylated, more particularly the modified FVIII of the invention is a substantially glycan-structure terminated with mannose residue deglycosylated FVIII polypeptide.

More particularly, the modified FVIII polypeptide of the invention comprises the substitution or the deletion of at least one amino acid of a glycosylation consensus site having the consensus sequence Asn-Xxx-Thr/Ser, wherein Xxx represents any amino acid. More particularly, the modified FVIII polypeptide of the invention comprises the substitution or the deletion of at least one amino acid selected in the group consisting of Asparagin 239, Asparagin 2118, Serine 241 and Threonin 2120, with reference to the full-length human FVIII polypeptide sequence set forth in SEQ ID No: 2. In a specific embodiment, Asparagin 239 is substituted with an amino acid selected from the group consisting of Alanine, Glycine, Serine, Glutamine, Threonin, Aspartic acid or Glutamic acid. In a further specific embodiment, Asparagin 2118 is substituted with an amino acid selected from the group consisting of Alanine, Serine, Glutamine, Threonin, Aspartic acid or Glutamic acid. In an other embodiment, Asparagin 239 is substituted with Alanine and/or Asparagin 2118 is substituted with Alanine. In a further embodiment, Asparagin 239 is substituted with Glutamine and/or Asparagin 2118 is substituted with Glutamine. In an other embodiment Asparagin 239 is substituted with Alanine and Asparagin 2118 is substituted with Glutamine. In an other embodiment Asparagin 239 is substituted with Glutamine and Asparagin 2118 is substituted with Alanine In an other specific embodiment, the modified FVIII polypeptide of the invention comprises at least one of (i) the amino acid sequence set forth in SEQ ID No: 6 and/or (ii) the amino acid sequence set forth in SEQ ID No: 8. In a further specific embodiment the modified FVIII polypeptide of the invention comprises at least one of (i) the amino acid sequence set forth in SEQ ID No: 12 and/or (ii) the amino acid sequence set forth in SEQ ID No: 14. In an other specific embodiment the modified FVIII polypeptide of the invention comprises (i) the amino acid sequence set forth in SEQ ID No: 6 and (ii) the amino acid sequence set forth in SEQ ID No: 14. In a further specific embodiment the modified FVIII polypeptide of the invention comprises (i) the amino acid sequence set forth in SEQ ID No: 12 and (ii) the amino acid sequence set forth in SEQ ID No: 8.

In an other aspect, the modified FVIII polypeptide of the invention is a procoagulant-active FVIII protein.

In an other aspect, the modified FVIII polypeptide of the invention further comprises the deletion of whole or part of the B domain set forth in SEQ ID No: 10. In an other preferred embodiment, the modified FVIII polypeptide of the invention is only partially deleted for the B domain, and, more preferably, the modified FVIII polypeptide of the invention still contains at least the first 226 amino acids of the B-domain (with reference to SEQ ID No: 10).

It is an other object of the invention to provide an isolated nucleic acid molecule or a modified isolated nucleic acid sequence encoding a FVIII protein comprising the modified FVIII polypeptide of the invention. In a specific embodiment, the nucleic acid sequence encoding a FVIII protein comprises at least one of (i) the nucleic acid sequence set forth in SEQ ID No: 5 and/or (ii) the nucleic acid sequence set forth in SEQ ID No: 7. In a further specific embodiment, the nucleic acid sequence encoding a FVIII protein comprises an isolated nucleic acid molecule capable of hybridizing under high stringency conditions with at least one of (i) the nucleic acid sequence set forth in SEQ ID No: 5 and/or (ii) the nucleic acid sequence set forth in SEQ ID No: 7.

In an other specific embodiment, the nucleic acid sequence encoding a FVIII protein comprises at least one of (i) the nucleic acid sequence set forth in SEQ ID No: 11 and/or (ii) the nucleic acid sequence set forth in SEQ ID No: 13. In a further specific embodiment, the nucleic acid sequence encoding a FVIII protein comprises an isolated nucleic acid molecule capable of hybridizing under high stringency conditions with at least one of (i) the nucleic acid sequence set forth in SEQ ID No: 11 and/or (ii) the nucleic acid sequence set forth in SEQ ID No: 13.

In an other specific embodiment, the nucleic acid sequence encoding a FVIII protein comprises at least one of (i) the nucleic acid sequence set forth in SEQ ID No: 5 and (ii) the nucleic acid sequence set forth in SEQ ID No: 13. In a further specific embodiment, the nucleic acid sequence encoding a FVIII protein comprises an isolated nucleic acid molecule capable of hybridizing under high stringency conditions with at least one of (i) the nucleic acid sequence set forth in SEQ ID No: 5 and (ii) the nucleic acid sequence set forth in SEQ ID No: 13.

In an other specific embodiment, the nucleic acid sequence encoding a FVIII protein comprises at least one of (i) the nucleic acid sequence set forth in SEQ ID No: 11 and (ii) the nucleic acid sequence set forth in SEQ ID No: 7. In a further specific embodiment, the nucleic acid sequence encoding a FVIII protein comprises an isolated nucleic acid molecule capable of hybridizing under high stringency conditions with at least one of (i) the nucleic acid sequence set forth in SEQ ID No: 11 and (ii) the nucleic acid sequence set forth in SEQ ID No: 7.

The present invention further provides an expression vector comprising an isolated nucleic acid molecule of the invention or an isolated nucleic acid molecule encoding a modified FVIII polypeptide of the invention.

It is an other object of the present invention to provide a host cell transfected with an expression vector comprising an isolated nucleic acid molecule of the invention allowing the expression of a FVIII protein or a modified FVIII polypeptide of the invention.

The present invention further provides a non-human transgenic organism expressing the FVIII protein of the invention, and particularly an organism selected from a microorganism, a non-human animal or a plant, and more particularly a mammal.

An other object of the present invention is to provide a composition comprising a FVIII protein as disclosed in the invention, and particularly a pharmaceutical composition or a lyophilised composition, further comprising a pharmaceutically acceptable carrier.

An other object of the present invention is to provide a method for the production of a FVIII protein according to the invention and comprising the steps of growing, in culture, a host cell transformed or transfected with a nucleic acid molecule of the invention or with a nucleic acid molecule encoding a FVIII protein of the invention, and isolating from the host cell and/or from the culture medium, the FVIII protein resulting from the expression of the nucleic acid molecule.

The present invention also provides the use of a FVIII protein according to the invention for the treatment of a bleeding disease, particularly a disease characterized by a FVIII deficiency, more particularly haemophilia A and acquired haemophilia A.

In a specific embodiment, the invention provides the use of a FVIII protein of the invention for the manufacture of a medicament for treating haemophilia A or acquired haemophilia A, as well as a method of treating Hemophilia A in a patient, comprising administering a clotting effective amount of the FVIII protein according to the invention to a patient in need thereof.

BRIEF DESCRIPTION OF THE DRAWINGS

FIG. 1: Mannose-sensitive entry of FVIII into Dendritic Cells (DCs).

Figure 4:
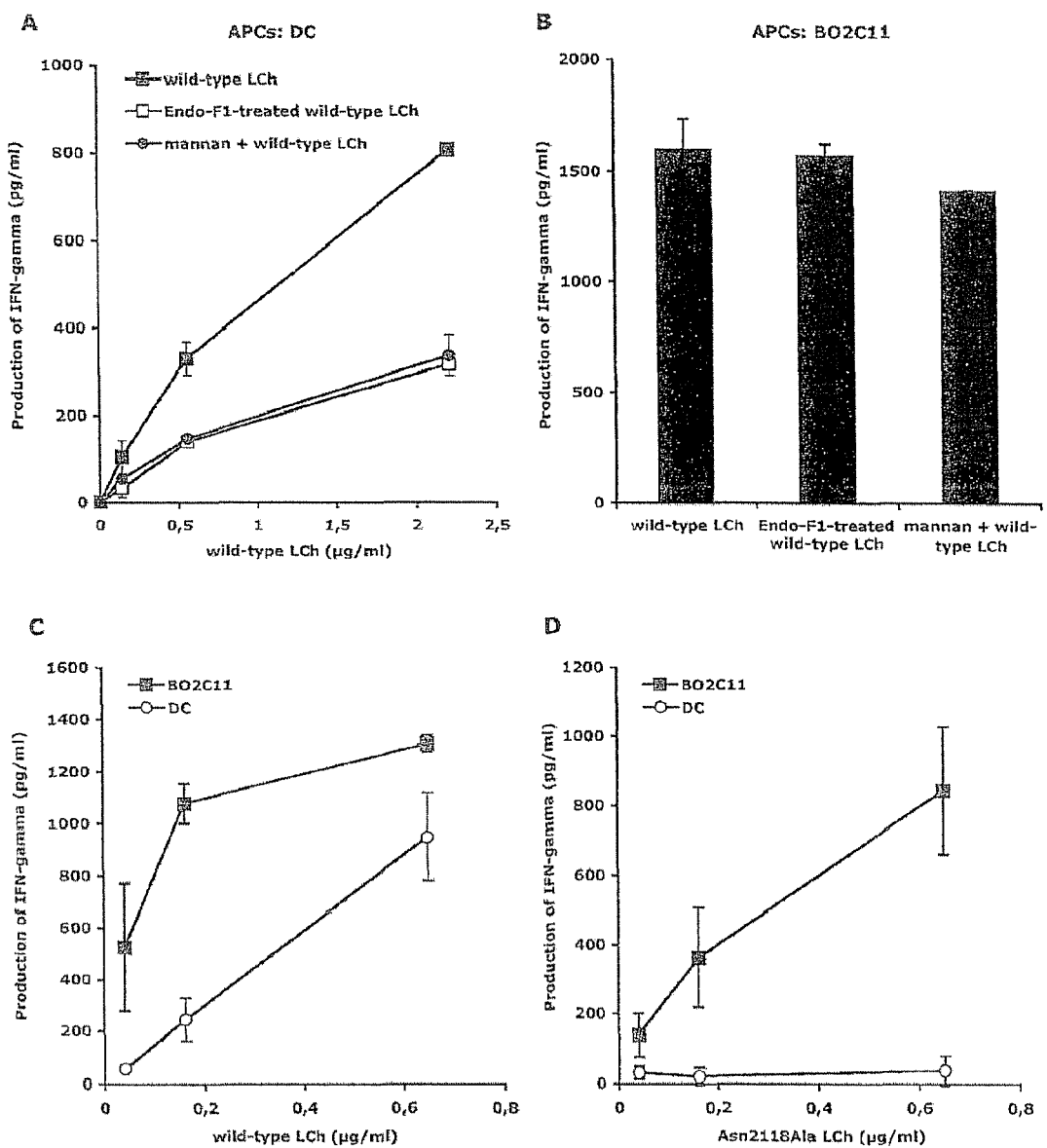

(A) DCs were pre-incubated with either 5 mM EDTA, 1 mg/ml mannan or 1 mg/ml D-Galactose for 30 min at 37° C., prior to the addition of FVIII (40 µg/ml) for 2 hours. The reported values depict the relative antigen uptake defined as $[(^{37°\ C.}MFI_{inh} - ^{4°\ C.}MFI_{medium})/(^{37°\ C.}MFI_{medium} - ^{4°\ C.}MFI_{medium})] \times 100$, where "$MFI_{inh}$" stands for the MFI detected in the presence of the inhibitor. Results are from 12 donors and statistical significance was calculated on the raw data using unpaired Student's test.

(B) Inhibition of endocytosis in DCs by mannan. Pre-incubation of DCs with mannan (1 mg/ml) was followed by the addition of dextran-FITC (50 µg/ml) or Lucifer yellow (200 µg/ml) for 2 hours.

FIG. 2: Mannose-sensitive uptake of FVIII by DCs results in the presentation of FVIII-derived peptides to FVIII-specific CD4+ T cells.

(A) DCs generated from DRB1*1501/DRB5*01 healthy donors were incubated (10000 cells/well) in medium alone or in presence of mannan (1 mg/ml) or anti-CD206 IgG (10 µg/ml) followed by incubation with the FVIII-specific T cell clone D9E9 (5000 cells/well) in the presence of varying doses of FVIII (5.56, 2.78 or 1.39 µg/ml) and 20 U/ml rhIL-2 for 20 hours at 37° C. Activation of T cells was assessed by the release of IFN-gamma in the culture supernatant. Results are from one representative experiment out of 3 to 8 independent experiments. IFN-gamma yields varied with different batches of D9E9 and different sources of donor DCs used in separate experiments.

(B) DCs generated from MHC II-matched donors were pre-incubated with mannan (1 mg/ml) or anti-CD206 IgG (10 µg/ml) followed by the addition of FVIII (5.56 µg/ml) or peptide $I^{2144}$-$T^{2161}$ (of SEQ ID NO: 9) (2 µg/ml) and D9E9. For each treatment, the IFN-gamma production was depicted relative to the maximum value obtained in each individual experiment (*: P<0.0001, as assessed using the Mann-Whitney test). Results are from 3 independent experiments.

(C) The human FVIII-specific HLA-matched B cell lines LE2E9 and BO2C11, or DCs were incubated in the presence of FVIII (10 µg/ml) and D9E9.

FIG. 3: Expected mannose residues located outside the B domain play a significant role in FVIII endocytosis by DCs leading to T cell activation.

(A) DCs were pre-incubated with mannan (1, 5, 10, 100 and 1000 µg/ml) prior to the addition of FVIII (40 µg/ml 143 nM, full circles) and BDD-FVIII (24.31 µg/ml, 143 nM, empty circles), or dextran-FITC (50 µg/ml). Uptake of the antigens was analyzed by flow cytometry. Percentage inhibition was calculated for each condition with respect to the condition without mannan. Representative of two individual experiments.

(B) Native or EndoF1-treated BDD-FVIII (3.7 µg/ml) was separated by 7.5% SDS-PAGE and transferred onto a nitrocellulose membrane. Transferred proteins were revealed using Protogold® or following incubation with 10 µg/ml CTLD4-7-Fc using an alkaline phosphatase-conjugated anti-human IgG. The light chain (LC) and Heavy chain (HC) were identified upon blotting with LC- and HC-specific monoclonal anti-FVIII IgGs (not shown).

(C) Reduced activation of T cells upon EndoF1-treatment of BDD-FVIII. Results depict one representative of 3 independent experiments. Yields of IFN-gamma varied with different batches of D9E9 and with the different sources of human DCs used in the different experiments. In order to statistically compare the three sets of experiments, the production of IFN-gamma was normalized with respect to the maximum value obtained in each individual experiment. Differences in normalized levels of T cell activation were statistically significant between "medium" and "EndoF1-treated", as assessed during ANOVA and the Fisher's PSLD test (P<0.0001, data not shown).

FIG. 4: Activation of a FVIII-specific T cell clone (D9E9) by a wild-type or a mutant FVIII light chain.

(A) and (B) Confirmation of a mannose-sensitive DC entry of the wild-type light chain of FVIII leading to T cell activation. The purified plasma-derived light chain of FVIII (Wild-type LCh) was treated with Endo-F1. The native wild-type Lch, the wild-type light chain in the presence of mannan (1 mg/ml) and the EndoF1-treated wild-type light chain were then added to DCs (panel A) or to a FVIII-specific B cell clone (BO2C11, panel B), and co-cultured with D9E9 cells for 20 hours. Activation of D9E9 was assessed by measuring IFN-gamma in the culture supernatant by an ELISA.

(C) and (D) Loss of activation of D9E9 upon site directed mutagenesis of the FVIII light chain. The BO2C11 B cell clone and monocyte-derived DCs were incubated with D9E9 in the presence of wild-type Lch (panel C) or in the presence of mutated Asn2118Ala LCh (panel D). Substitution of Asn2118 by an Ala residue removes a site for N-mannosylation. Activation of D9E9 was assessed after 20 hours by measuring IFN-gamma in the culture supernatant.

Figure 5:

FIG. 5: Schematic representation of full-length FVIII structure.

The full-length heterodimeric human FVIII (of SEQ ID No: 2) consists of 2332 amino acids and encompasses a "Heavy chain" corresponding to residues 1 to 1648 and containing domains A1-a1-A2-a2-B, and a "Light chain" corresponding to residues 1649 to 2332 and containing domains a3-A3-C1-C2 (numbering of the amino acid residues refers to the amino acid sequence set forth in SEQ ID No: 2). The FVIII molecule contains 25 consensus sequences (Asn-Xxx-Thr/Ser) that allow N-linked glycosylation, of which 20 have been shown to be glycosylated (1)

FIG. 6: Amino acid sequence of Native full-length human FVIII (as set forth in SEQ ID No: 1)

The underlined amino acid sequence corresponds to the signal peptide containing the first 19 full-length heterodimeric human FVIII (of SEQ ID NO: 2) starts with the Alanine residue located at position 20. The amino acid residues represented in bold correspond to the consensus glycosylation sites, which are preferentially modified in an embodiment of the present invention.

B domain correspond to the amino acid sequence ranging from position 760 to position 1667 of the amino acid sequence set forth in SEQ ID No: 1 and disclosed in FIG. 6. The native light chain used as a control in example 6, and which is referred to as "the purified plasma-derived light chain of FVIII" corresponds to the amino acid sequence ranging from position 1668 to position 2351 of the amino acid sequence set forth in SEQ ID No: 1 and disclosed in FIG. 6.

The heavy chain of native human FVIII corresponds to the amino acid sequence ranging from position 19 to position 759 of the amino acid sequence set forth in SEQ ID No: 1 and disclosed in FIG. 6.

FIG. 7: BDD (for B Domain Deleted)—human FVIII.

B-domain of factor VIII was shown to be dispensable for procoagulant activity. FIG. 7 discloses both the amino acid sequence and the nucleic acid sequence corresponding to the B-domain-deleted human FVIII obtained when B-domain is removed from the full-length human FVIII set forth in SEQ ID No: 2. The amino acid sequence and nucleic acid sequence are joined together such that each amino acid (on top) faces the corresponding nucleic acid codon (on bottom). The amino acid sequence and the nucleic acid sequence corresponding to BDD-human FVIII are numbered independently one from the other (numbering is disclosed on the right side of the sequences). The amino acid sequence of the BDD-human FVIII disclosed in FIG. 7 correspond to the sequence set forth in SEQ ID No: 4. The nucleic acid sequence of the BDD-human FVIII disclosed in FIG. 7 correspond to the sequence set forth in SEQ ID No: 3. The amino acid residues (or the corresponding nucleic acid residues) represented in bold correspond to the consensus glycosylation sites which are preferentially modified in an embodiment of the present invention. The character "*" is placed above the stop codon.

FIG. 8: Human FVIII heavy chain modified by the substitution of Asn with Ala at position 239 (with reference to the full-length human FVIII sequence set forth in SEQ ID No: 2)

FIG. 8 discloses both the amino acid sequence and the nucleic acid sequence corresponding to the modified heavy chain of the human FVIII implemented in a particular embodiment of the present invention. The amino acid sequence and nucleic acid sequence are joined together such that each amino acid (on top) faces the corresponding nucleic acid codon (on bottom). The amino acid sequence and the nucleic acid sequence corresponding to the modified heavy chain of the human FVIII are numbered independently one from the other (numbering is disclosed on the right side of the sequences). The amino acid sequence of the modified heavy chain of the human FVIII disclosed in FIG. 8 correspond to the sequence set forth in SEQ ID No: 6. The nucleic acid sequence of the modified heavy chain of the human FVIII disclosed in FIG. 8 correspond to the sequence set forth in SEQ ID No: 5. The amino acid residue (Alanine) (or the corresponding nucleic acid codon) represented in bold correspond to the glycosylation site (Asn 239) which was modified in an embodiment of the present invention.

FIG. 9: Human FVIII light chain modified by the substitution of Asn with Ala at position 2118 (with reference to the full-length human FVIII sequence set forth in SEQ ID No: 2)

FIG. 9 discloses both the amino acid sequence and the nucleic acid sequence corresponding to the modified light chain of the human FVIII implemented in a particular embodiment of the present invention. The amino acid sequence and nucleic acid sequence are joined together such that each amino acid (on top) faces the corresponding nucleic acid codon (on bottom). The amino acid sequence and the nucleic acid sequence corresponding to the modified light chain of the human FVIII are numbered independently one from the other (numbering is disclosed on the right side of the sequences). The amino acid sequence of the modified light chain of the human FVIII disclosed in FIG. 8 correspond to the sequence set forth in SEQ ID No: 8. The nucleic acid sequence of the modified light chain of the human FVIII disclosed in FIG. 8 correspond to the sequence set forth in SEQ ID No: 7. The amino acid residue (Alanine) (or the corresponding nucleic acid codon) represented in bold correspond to the glycosylation site (Asn 2218) which was modified in an embodiment of the present invention.

Figure 10:
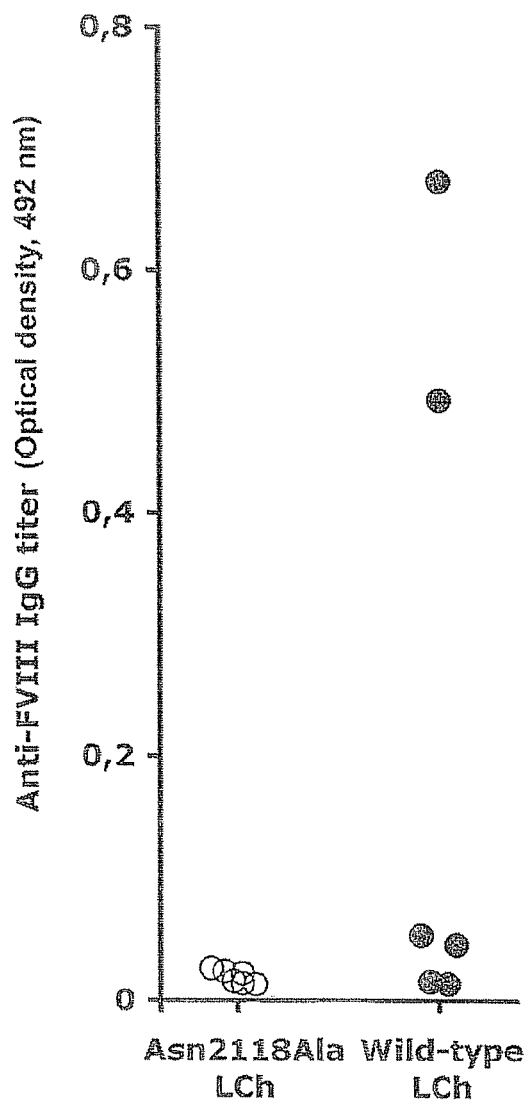

FIG. 10: production of anti-FVIII IgG in a mouse by a wild-type or a mutant FVIII light chain.

The purified plasma-derivated light chain of human FVIII (wtLCh) and the mutated LCh of FVIII (Asn2118Ala LCh) were injected (0.2 μg protein in 200 μL PBS) intravenously to FVIII-deficient mice four times at weekly intervals. One week after the fourth injection, mice were bled and levels of anti-FVIII IgG were investigated using a FVIII-specific ELISA. Mice sera diluted 1 into 90 were incubated in ELISA plate coated with human FVIII. (Recombinate, Baxter) Bound IgG were revealed using anti-murine IgG coupled to peroxidase, and its substrate (OPD). Intensity of binding was measured by optical density at 492 nm with a spectrometer (Tecan Genyos).

Figure 11:
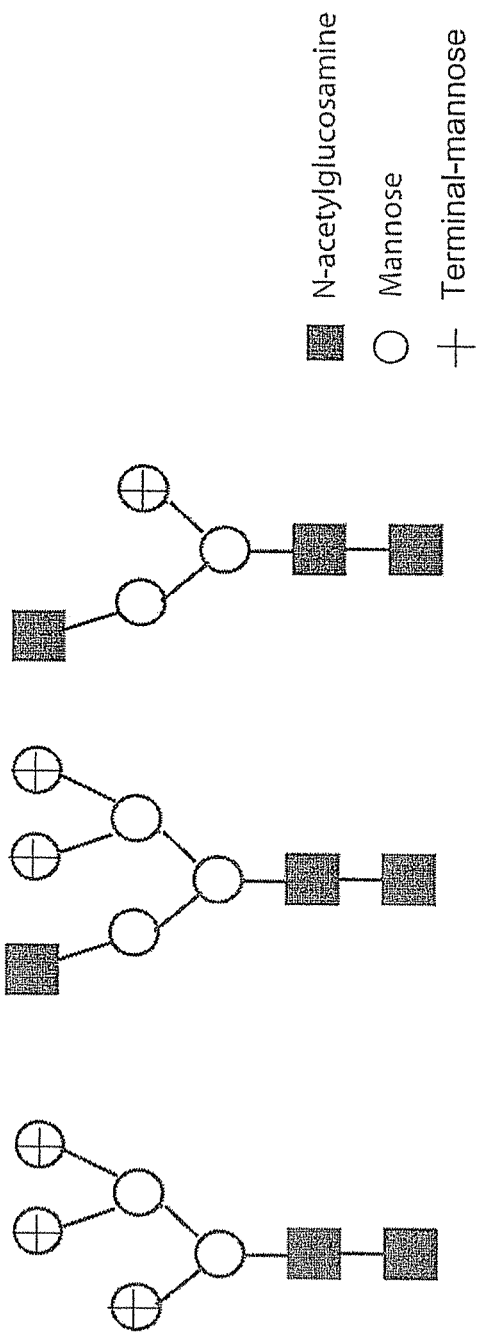

FIG. 11: schematic representation of three kind of glycan-structures terminated with mannose residue(s)

DETAILED DESCRIPTION OF THE INVENTION

As used herein, "FVIII protein" refers to an amino acid molecule comprising at least a FVIII polypeptide but which is not limited to this polypeptide. Therefore, the FVIII polypeptide of the invention represents at least about 50%, preferentially 60%, 70%, 75%, 80%, 85%, 90%, 95%, 96%, 97%, 98%, 99% or 100% of the amino acid content of the FVIII protein of the invention. When the proportion of the FVIII polypeptide in the FVIII protein differs from 100%, the FVIII protein might contain any another amino acid sequence, such that the FVIII protein should be considered as a chimeric protein. The additional amino acid sequences comprised in the FVIII protein may be linked either covalently or non-covalently to the FVIII polypeptide, and could correspond or originate from any natural or synthetic polypeptide. These additional amino acid sequences could act as enzymes or active proteins, signal sequences for cellular trafficking, translocation, exportation, secretion, or they could play the role of recognition sequences for other enzymes and/or processing proteins.

As used herein "FVIII polypeptide" refers to a polypeptide that has coagulation activity and similar thrombin activation profile compared with full-length human Factor VIII of SEQ ID No:2, and has at least about 60%, 70%, 75%, 80%, 85%, 90%, 95%, 96%, 97%, 98%, 99% or 100% identity to the 1-740 and 1689-2332 regions of the polypeptide sequence represented by SEQ ID NO:2. In particular, it is understood that various mutations and conservative amino acid changes are tolerable, as well as certain non-conservative amino acid changes, so long as the variant Factor VIII has coagulation activity. Fragments and certain glycosylations are also permitted, and preferred, indeed any change at all to the Factor VIII polypeptide is permitted so long as the polypeptide retains its specific activity.

As used herein "FVIII polypeptide" also refers to a polypeptide that has coagulation activity and similar thrombin activation profile compared with full-length human Factor VIII of SEQ ID No:2, and has at least about 60%, 70%, 75%, 80%, 85%, 90%, 95%, 96%, 97%, 95%, 99% or 100% identity to full-length human Factor VIII of SEQ ID No:2. In particular, it is understood that various mutations and conservative amino acid changes are tolerable, as well as certain non-conservative amino acid changes, so long as the variant Factor VIII has coagulation activity. Fragments and certain glycosylations are also permitted, and preferred, indeed any change at all to the Factor VIII polypeptide is permitted so long as the polypeptide retains its specific activity.

As used herein, the "modified FVIII polypeptide", may contain any number of amino acids or alterations of amino acids in the native, in the full-length or in the BDD-FVIII non-critical region, including substitutions and/or insertions and/or deletions in any other region of the polypeptide molecule, so long as the polypeptide variant includes a sequence that is at least about 60%, 70%, 75%, 80%, 85%, 90%, 95%, 96%, 97%, 98% or 99% identical to at least about 1-740 and/or 1689-2332 polypeptide sequence of SEQ ID No:2, and the presence of the variations does not hinder the variant FVIII activity.

As used herein, "modified FVIII polypeptide" encompasses amino acid sequences having 60%, 70%, 75%, 80%, 85%, 90%, 95%, 96%, 97%, 95%, 99% 100% sequence homology to the indicated reference sequence, i.e. to human full length Factor VIII of SEQ ID NO: 2.

As used herein, the term "modified" refers to molecules with some differences in their amino acid sequences as compared to a reference (e.g. full-length Factor VIII sequence) polypeptide. The amino acid alterations may be substitutions, insertions, deletions or any desired combinations of such changes in a native or full-length amino acid sequence. The substitutions may be single, where only one amino acid in the molecule has been substituted, or they may be multiple, where two or more amino acids have been substituted in the same molecule.

To improve or alter the characteristics of FVIII polypeptide of the present invention, amino acid engineering may be employed. Recombinant DNA technology known to those skilled in the art can be used to create novel mutant polypeptides including single or multiple amino acid substitutions, deletions, additions, or fusion proteins. Such modified polypeptides can show, e.g., increased/decreased activity or increased/decreased stability. In addition, they may be purified in higher yields and show better solubility than the corresponding natural polypeptide, at least under certain purification and storage conditions.

As used herein, the term "polypeptide" includes not only full length protein molecules but also fragments thereof which, by themselves or with other fragments, generate FVIII procoagulant activity in a clotting assay. It will be appreciated that synthetic polypeptides of the novel protein products of the present invention are also within the scope of the invention and can be manufactured according to standard synthetic methods. It will also be appreciated that in the amino acid numbering system used herein, amino acid residue 1 is the first residue of the native, mature FVIII protein. It will further be appreciated that the term "domain" refers to the approximate regions of FVIII, known to those skilled in the art.

The amino acid symbols used in the present application include the following: Either single or three letter abbreviations for the amino acids are used throughout the application, and may be used interchangeably, and have the following meaning: A or Ala=alanine; R or Arg=arginine; N or Asn=asparagine; D or Asp=aspartic acid; C or Cys=cysteine; Q Gln=glutamine; E or Glu=glutamic acid; G or Gly=glycine; H or His=histidine; I or Ile=isoleucine; L or Leu=leucine; K or Lys=lysine; M or Met=methionine; F or Phe=phenylalanine; P or Pro=proline; S or Ser=serine; T or Thr=threonine; W or Trp=tryptophan; Y or Tyr=tyrosine; and V or Val=valine.

Moreover, as used herein "the modification of modified FVIII polypeptide" is not to be limited to the exact recited number or position as that which is indicated, so long as the function and result achieved is the same. A few amino acid positions may be inserted, added or deleted from the N- or C-terminal ends or from another part of human full length Factor VIII so long as the functional activity, such as thrombin cleavage or procoagulant functions are maintained. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

As used herein, "fragment" refers to a part of a polypeptide, which retains usable and functional characteristics. For example, as used within the context of the present invention, the Factor VIII polypeptide fragment has the function of coagulating blood.

As used herein, a protein having factor VIII procoagulant activity is a protein which causes the activation of Factor X in in vitro, ex vivo or in vivo model systems. As non-limiting examples, this definition includes full length recombinant human factor VIII and the B domain deleted factor VIII. As used herein the term "procoagulant-active" and "active" FVIII, may be used interchangeably to refer to one or more polypeptide(s) or proteins demonstrating procoagulant activity in a clotting assay. The term FVIII may be used herein to encompass FVIIIa and one skilled in the art will appreciate from the context in which the terms are used which term (pre-thrombin activated FVIII or thrombin activated FVIII (FVIIIa)) is intended. As used herein, "glycan-structure terminated with mannose residue deglycosylated FVIII polypeptide" refers to a FVIII polypeptide or a modified FVIII polypeptide that lacks one or more glycan structure(s) terminated with mannose residue(s).

As used herein, "glycan-structure(s) terminated with mannose residue(s)" refers to a glycan-structure at a site of glycosylation terminated with one or more mannose residue(s) away from the polypeptide backbone, such mannose residue is called terminal-mannose residue. The term "glycan-structure(s) terminated with mannose residue(s)" includes mono and multi-antennary glycan-structure(s) with one or more mannose residue(s) away from the polypeptide backbone, more particularly the term "glycan-structure(s) terminated with mannose residue(s)" includes oligomannose-type glycan-structure(s) (FIG. 11).

As used herein, "terminal-mannose residue" refers to a mannose residue away from the polypeptide backbone which terminates an antenna of a glycan-structure at a site of glycosylation (FIG. 11).

As used herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. "High stringency conditions" for the annealing process may involve, for example, high temperature and/or low salt content, which disfavor hydrogen-bonding contacts among mismatched base pairs. "Low stringency conditions" would involve lower temperature, and/or higher salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6*SSC at about 45[deg.] C., followed by a wash of 2*SSC at 50[deg.] C. are known to those skilled in the art or can be found in Current Protocols in Molecular Biology, John Wiley & Sons, N.Y. (1989), 6.31-6.3.6. For example, the salt concentration in the wash step can be selected from a low stringency of about 2*SSC at 50[deg.] C. to a high stringency of about 0.2*SSC at 50[deg.] C. In addition, the temperature in the wash step can be increased from low stringency at room temperature, about 22[deg.] C., to ° high stringency conditions, at about 75[deg.] C. Other stringency parameters are described in Maniatis, T., et al., Molecular Cloning: A Laboratory Manual, Cold Spring Harbor Laboratory Press, Cold Spring N.Y., (1982), at pp. 387-389; see also Sambrook J. et al., Molecular Cloning: A Laboratory Manual, Second Edition, Volume 2, Cold Spring Harbor Laboratory Press, Cold Spring, N.Y. at pp. 8.46-8.47 (1989).

As used herein, "carriers" include pharmaceutically acceptable carriers, excipients, or stabilizers which are nontoxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN(R), polyethylene glycol (PEG), and PLURONICS(R).

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state. In a preferred embodiment of the invention, the "effective amount" is defined as an amount of compound capable of effecting coagulation of blood.

As used herein, "host cell" includes an individual cell or cell culture, which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or ex vivo with a vector comprising a polynucleotide encoding an angiogenic factor.

As used herein, "purified" or "isolated" refers to biological molecules that are removed from their natural environment and are isolated or separated and are free from other components with which they are naturally associated.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. Preferably, the polynucleotide is DNA.

In selecting a preferred host cell for transfection by the vectors of the invention, which comprise DNA sequences encoding both FVIII derivatives and for example, dihydrofolate reductase (DHFR) protein, it is appropriate to select the host according to the type of DHFR protein employed. If wild type DHFR protein is employed, it is preferable to select a host cell, which is deficient in DHFR, thus permitting the use of the DHFR coding sequence as a marker for successful transfection in selective medium, which lacks hypoxanthine, glycine, and thymidine. On the other hand, if DHFR protein with low binding affinity for methotrexate (MTX) is used as the regulatory sequence, it is not necessary to use DHFR resistant cells. Mutant DHFR is resistant to MTX, therefore, MTX containing media can be used as a means of selection provided that the host cells themselves are MTX sensitive. Alternatively, a wild type DHFR gene may be employed as an amplification marker in a host cell, which is not deficient in DHFR provided that a second drug selectable marker is employed, such as hygromycin resistance. Examples which are set forth describe the use of CHO cells (CHO-DBX11 cells) resistant to MTX as host cells and on vectors which employ the CMV and SV40 promoter as regulatory sequences to drive the on of FVIII derivatives and DHFR, respectively. Other selectable markers include genes that confer resistance to drugs such as neomycin, hygromycin, and methotrexate.

As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

In another aspect, the invention provides an isolated nucleic acid molecule comprising a polynucleotide which hybridizes under stringent hybridization conditions to a portion of a nucleic acid molecule of the invention described above. Hybridizing polynucleotides are useful as probes and primers as discussed above. Portions of a polynucleotide which hybridize to the FVIII polypeptide encoding sequence, which may be precisely specified by 5' and 3' base positions or by size in nucleotide bases as described above or precisely excluded in the same manner. Similarly, portions of a polynucleotide, which hybridize to the FVIII polypeptide, which may be used as probes and primers as well. Preferred hybridizing polynucleotides of the present invention are those that, when labeled and used in a hybridization assay known in the art (e.g. Southern and Northern blot analysis), display the greatest signal strength regardless of other heterologous sequences present in equimolar amounts.

As used herein, modified nucleic acid sequences include those produced by nucleotide substitutions, deletions, or additions. The substitutions, deletions, or additions may involve one or more nucleotides. Alterations in the amino acid sequence may produce conservative or non-conservative amino acid substitutions, deletions or additions. Especially preferred among these are silent substitutions, additions and deletions, which do not alter the properties and activities of the polypeptides of the present invention or portions thereof. Also preferred in this regard are conservative substitutions.

The invention allows for the use of sequences in expression vectors, as well as to transfect host cells and cell lines, be these prokaryotic or eukaryotic cells. The invention also allows for purification of the polypeptides expressed from the expression vector. The expression vector may contain various molecular tags for easy purification. Subsequently obtained expression construct may be transformed into any host cell of choice. Cell lysates from the host cell is isolated by established methods well known in the field.

In a specific embodiment, nucleic acids comprising sequences encoding the FVIII protein or the modified Factor VIII polypeptide are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. In a preferred aspect, nucleic acid sequences may encode a Factor VIII polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding-nucleic acids. Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering them so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (which can be used to target cell types specifically expressing the receptors) and so on.

Alternatively, the nucleic acid can be introduced intracellularly and incorporated within host cell DNA for expression, by homologous recombination. In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient. In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In one embodiment, the present invention relates to treatment for blood clotting diseases. In this way, the inventive therapeutic compound may be administered to human patients who are either suffering from, or prone to suffer from the disease by providing compounds that stimulate blood coagulation. In particular, the disease may be hemophilia, in particular, hemophilia A. The formulation of therapeutic compounds is generally known in the art and reference can conveniently be made to Remington's Pharmaceutical Sciences, 17th ed., Mack Publishing Co., Easton, Pa., USA.

Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (e.g. using slow release molecules by the intraperitoneal route or by using cells e.g. monocytes or dendrite cells sensitised in vitro and adoptively transferred to the recipient). Depending on the route of administration, the FVIII protein or the modified FVIII polypeptide may be required to be coated in a material to protect it from the action of enzymes, acids and other natural conditions which may inactivate said ingredients.

The pharmaceutical forms suitable for injectable use include sterile aqueous solutions (where water-soluble) or dispersions and sterile powders for the extemporaneous preparation of sterile injectable solutions or dispersion. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient In a particular embodiment, mammalian cell culture is a method of expressing exogenous DNA to produce the functional human FVIII derivatives disclosed in this invention. In particular, common mammalian cells used for production of recombinant proteins, such as Chinese hamster ovary (CHO) cell lines, Baby hamster kidney (BHK) cell line, COS cell lines, HKB11 (Hybrid of Kidney and B cells; ATCC # CRL-12568), COS-1 (ATCC CRL 1650), and Madin Darby canine kidney (MDCK) cell line are of interest. Expression vectors for such cells ordinarily include (if necessary) (an) origin(s) of replication, a promoter located in front of the gene to be expressed, along with any necessary ribosome binding sites, RNA splice sites, polyadenylation site, and transcriptional terminator sequences.

For use in mammalian cells, the regulatory functions on the expression vectors may be provided by viral material. For example, commonly used promoters are derived from elongation factor-1 (EF-1), Simian Virus 40 (SV40) (15), Cytomegalovirus (CMV) (16) and major late promoter from adenovirus 2 (17). Furthermore, it is also possible, and often desirable, to utilize promoter or regulatory sequences normally associated with the desired gene sequence, provided such regulatory sequences are compatible with the host cell systems.

Cellular promoters include the mouse kappa gene promoter (18), the mouse $V_H$ promoter (19) and the mouse metallothionein-I promoter (20). Expression vectors may also contain a set of RNA splicing sites located downstream from the promoter and upstream from the insertion site for the FVIII sequence itself. Preferred RNA splicing sites may be obtained from adenovirus and/or immunoglobulin genes. Expression vectors may also contain a set of RNA splicing sites located in the cDNA FVIII sequence. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region or the human growth hormone gene terminator (21). The expression vectors may also include a noncoding viral leader sequence, such as the adenovirus 2 tripartite leader, located between the promoter and the RNA splice sites; and enhancer sequences, such as the SV40 enhancer.

Modified FVIII produced according to the present invention may be purified by affinity chromatography on an anti-FVIII antibody column. Additional purification may be achieved by conventional chemical purification means, such as high performance liquid chromatography (HPLC). Other methods of purification, including barium citrate precipitation, are known in the art, and may be applied to the purification of the novel modified FVIII. Substantially pure modified FVIII may be used in pharmaceutical uses. Once purified, partially or to homogeneity as desired, the modified FVIII may then be used therapeutically.

As used herein, $I^{2144}$-$T^{2161}$ peptide is a synthetic peptide of SEQ ID NO: 9. This peptide is not mannosylated, thus, mannan has no effect on its receptor-mediated endocytosis by Antigen Presenting Cells (APC), like Dendritic Cells (DCs).

As used herein, D9E9 cells are human FVIII-specific CD4+ T cell clones developed by Marc Jacquemin (Ref Jacquemin Blood 2003). These cells produce IFN-gamma when they are incubated with Antigen Presenting Cells that have previously endocytosed FVIII or the FVIII-derived peptide I2144-T2161.

As used herein, LE2E9 cells are human FVIII-specific B cell clone developed by Marc Jacquemin (Ref Peerlinck Blood 1999). These cells produce a human FVIII-specific IgG4 that recognize the C1 domain of FVIII.

As used herein, BO2C11 cells are human FVIII-specific B cell clone developed by Marc Jacquemin (Ref Jacquemin Blood 1998). These cells produce a human FVIII-specific IgG4 that recognize the C2 domain of FVIII.

As used herein, the CTLD4-7Fc molecule if a chimeric construct including domains 4 to 7 of the murine macrophage mannose receptor (CD206). The CTLD4-7Fc molecule was produced by Luisa Martinez-Pomares (Linehan 2001 Eur J Immunol).

As used herein, Dendritic Cell (DC) are professional antigen presenting cells that are characterized by a variety of specific surface markers (CD1a, CD11c, HLA-DR, CDSO, CD86, CD83, CD40, ...) and functions (endocytosis of antigen, presentation of antigen to T lymphocytes).

As used herein, anti-CD206 PAM-1 antibody is an antibody specifically directed against the human macrophage mannose receptor (CD206). It was produced by P. Allavena (Laboratory of Cellular Immunology, Instituto Mario Negri, Milan, Italy).

The following sequence corresponds to the amino acid sequence of SEQ ID No: 1, i.e. to the amino acid sequence of native full length human factor VIII comprising the 19 amino acid signal peptide:

```
MQIELSTCFFLCLLRFCFSATRRYYLGAVELSWDYMQSDLGELPVDARFP

PRVPKSFPFNTSVVYKKTLFVEFTDHLFNIAKPRPPWMGLLGFTIQAEVY

DTVVITLKNMASHPVSLHAVGVSYWKASEGAEYDDQTSQREREDDKVFPG

GSHTYVWQVLKENGPMASDPLCLTYSYLSHVDLVKDLNSGLIGALLVCRE

GSLAKEKTQTLHKFILLFAVFDEGKSWHSETKNSLMQDRDAASARAWPKM

HTVNGYVNRSLPGLIGCHRKSVYWHVIGMGTTPEVHSIFLEGHTFLVRNH

RQASLEISPITFLTAQTLLMDLGQFLLFCHISSHQHDGMEAYVKVDSCPE

EPQLRMKNNEEAEDYDDDLTDSEMDVVRFDDDNSPSFIQIRSVAKKHPKT
```

```
WVHYIAAEEEDWDYAPLVLAPDDRSYKSQYLNNGPQRIGRKYRKVRFMAY

TDETFKTREAIQHESGILGPLLYGEVGDTLLIIFKNQASRPYNIYPHGIT

DVRPLYSRRLPKGVKHLKDFPILPGEIFKYKWTVTVEDGPTKSDPRCLTR

YYSSFVNMERDLASCLIGPLLICYKESVDQRGNQIMSDKRNVILFSVFDE

NRSWYLTENIQRFLPNPAGVQLEDPEFQASNIMHSINGYVFDSLQLSVCL

HEVAYWYILSIGAQTDFLSVFFSGYTFKHKMVYEDTLTLFPFSGETVFMS

MENPGLWILGCHNSDFRNRGMTALLKVSSCDKNTGDYYEDSYEDISAYLL

SKNNAIEPRSFSQNSRHPSTRQKQFNATTIPENDIEKTDPWFAHRTPMPK

IQNVSSSDLLMLLRQSPTPHGLSLSDLQEAKYETFSDDPSPGAIDSNNSL

SENTHFRPQLHHSGDMVFTPESGLQLRLNEKLGTTAATELKKLDFKVSST

SNNLISTIPSDNLAAGTDNTSSLGPPSMPVHYDSQLDTTLFGKKSSPLTE

SGGPLSLSEENNDSKLLESGLMNSQESSWGKNVSSTESGRLFKGKRAHGP

ALLTKDNALFKVSISLLKTNKTSNNSATNRKTHIDGPSLLIENSPSVWQN

ILESDTEFKKVTPLIHDRMLMDKNATALRLNHMSNKTTSSKNMEMVQQKK

EGPIPPDAQNPDMSFFKMLFLPESARWIQRTHGKNSLNSGQGPSPKQLVS

LGPEKSVEGQNFLSEKNKVVVGKGEFTKDVGLKEMVFPSSRNLFLTNLDN

LHENNTHNQEKKIQEEIEKKETLIQENVVLPQIHTVTGTKNFMKNLFLLS

TRQNVEGSYDGAYAPVLQDFRSLNDSTNRTKKHTAHFSKKGEEENLEGLG

NQTKQIVEKYACTTRISPNTSQQNFVTQRSKRALKQFRLPLEETELEKRI

IVDDTSTQWSKNMKHLTPSTLTQIDYNEKEKGAITQSPLSDCLTRSHSIP

QANRSPLPIAKVSSFPSIRPIYLTRVLFQDNSSHLPAASYRKKDSGVQES

SHFLQGAKKNNLSLAILTLEMTGDQREVGSLGTSATNSVTYKRVENTVLP

KPDLPKTSGKVELLPKVHIYQKDLFPTETSNGSPGHLDLVEGSLLQCTEG

AIKWNEANRPGKVPFLRVATESSAKTPSKLLDPLAWDNHYGTQIPKEEWK

SQEKSPEKTAFKKKDTILSLNACESNHAIAAINEGQNKPEIEVTWAKQGR

TERLCSQNPPVLKRHQREITRTTLQSDQEEIDYDDTISVEMKKEDFDIYD

EDENQSPRSFQKKTRHYFIAAVERLWDYGMSSSPHVLRNRAQSGSVPQFK

KVVFQEFTDGSFTQPLYRGELNEHLGLLGPYIRAEVEDNIMVTFRNQASR

PYSFYSSLISYEEDQRQGAEPRKNFVKPNETKTYFWKVQHHMAPTKDEFD

CKAWAYFSDVDLEKDVHSGLIGPLLVCHTNTLNPAHGRQVTVQEFALFFT

IFDETKSWYFTENMERNCRAPCNIQMEDPTFKENYRFHAINGYIMDTLPG

LVMAQDQRIRWYLLSMGSNENIHSIHFSGHVFTVRKKEEYKMALYNLYPG

VFETVEMLPSKAGIWRVECLIGEHLHAGMSTLFLVYSNKCQTPLGMASGH

IRDFQITASGQYGQWAPKLARLHYSGSINAWSTKEPFSWIKVDLLAPMII

HGIKTQGARQKFSSLYISQFIIMYSLDGKKWQTYRGNSTGTLMVFFGNVD

SSGIKHNIFNPPIIARYIRLHPTHYSIRSTLRMELMGCDLNSCSMPLGME

SKAISDAQITASSYFTNMFATWSPSKARLHLQGRSNAWRPQVNNPKEWLQ

VDFQKTMKVTGVTTQGVKSLLTSMYVKEFLISSSQDGHQWTLFFQNGKVK

VFQGNQDSFTPVVNSLDPPLLTRYLRIHPQSWVHQIALRMEVLGCEAQDL

Y
```

The following sequence corresponds to the amino acid sequence of SEQ ID No: 2, i.e. to the amino acid sequence of full length human factor VIII which does not comprises the 19 amino acid signal peptide:

```
ATRRYYLGAVELSWDYMQSDLGELPVDARFPPRVFKSFPFNTSVVYKKTL

FVEPTDHLFNIAKPRPPWMGLLGPTIQAEVYDTVVITLKNMASHPVSLHA

VGVSYWKASEGAEYDDQTSQREKEDDKVFPCGSHTYVWQVLKENGPMASD

PLCLTYSYLSHVDLVKDLNSGLIGALLVCREGSLAKEKTQTLHKFILLFA

VFDEGKSWHSETKNSLMQDRDAASARAWPKMHTVNGYVNRSLPGLIGCHR

KSVYWHVIGMGTTPEVHSIFLEGHTFLVRNHRQASLEISPITFLTAQTLL

MDLGQFLLFCHISSHQHDGMEAYVKVDSCPEEPQLRMKNNEEAEDYDDDL

TDSEMDVVRFDDDNSPSFIQIRSVAKKHPKTWVHYIAAEEEDWDYAPLVL

APDDRSYKSQYLNNGPQRIGRKYKKVRFMAYTDETFKTREAIQHESGILG

PLLYGEVGDTLLIIFKNQASRPYNIYPHGITDVRPLYSRRLPKGVKHLKD

FPTLPGEIFKYKWTVTVEDGPTKSDPRCLTRYYSSFVNMERDLASGLIGP

LLICYKESVDQRGNQIMSDKRNVILFSVFDENRSWYLTENIQRFLPNPAG

VQLEDPEFQASNIMHSINGYVFDSLQLSVCLHEVAYWYILSIGAQTDFLS

VFFSGYTFKHKMVYEDTLTLFPFSGETVFMSMENPGLWILGCHNSDFRNR

GMTALLKVSSCDKNTGDYYEDSYEDISAYLLSKNNAIEPRSFSQNSRHPS

TRQKQFNATTIPENDIEKTDPWFAHRTPMPKIQNVSSSDLLMLLRQSPTP

HGLSLSDLQEAKYETFSDDPSPGAIDSNNSLSEMTHFRPQLHHSGDMVFT

PESGLQLRLNEKLGTTAATELKKLDFKVSSTSNNLISTIPSDNLAAGTDN

TSSLGPPSMPVHYDSQLDTTLFGKKSSPLTESGGPLSLSEENNDSKLLES

GLMNSQESSWGKNVSSTESGRLFKGKRAHGPALLTKDNALFKVSISLLKT

NKTSNNSATNRKTHIDGPSLLIENSPSVWQNILESDTEFKKVTPLIHDRM

LMDKNATALRLNHMSNKTTSSKNMEMVQQKKEGPIPPDAQNPDMSFFKML

FLPESARWIQRTNGKNSLNSGQGPSPKQLVSLGPEKSVEGQNFLSEKNKV

VVGKGEFTKDVGLKEMVFPSSRNLFLTNLDNLHENNTHNQEKKIQEEIEK

KETLIQENVVLPQIHTVTGTKNFMKNLFLLSTRQNVEGSYDGAYAPVLQD

FRSLNDSTNRTKKHTAHFSKKGEEENLEGLGNQTKQIVEKYACTTRISPN

TSQQNFVTQRSKRALKQFRLPLEETELEKRIIVDDTSTQWSKNMKHLTPS

TLTQIDYNEKEKGAITQSPLSDCLTRSNSIPQANRSPLPIAKVSSFPSIR

PIYLTRVLFQDNSSHLPAASYRKKDSGVQESSHFLQGAKKNNLSLAILTL

EMTGDQREVGSLGTSATNSVTYKKVENTVLPKPDLPKTSGKVELLPKVHI

YQKDLFPTETSNGSPGHLDLVEGSLLQGTEGAIKWNEANRPGKVPFLRVA

TESSAKTPSRLLDPLAWDNHYGTQIPKEEWESQEKSPEKTAFKKKDTILS

LNACESNHAIAAINEGQNKPEIEVTWAKQGRTERLCSQNPPVLKRHQREI

TRTTLQSDQEEIDYDDTISVEMKKEDFDIYDEDENQSPRSFQKKTRHYFI

AAVERLWDYGMSSSPHVLRNRAQSGSVPQFKKVVFQEFTDGSFTQPLYRG

ELNEHLGLLGPYIRAEVEDNIMVTFRNQASRPYSFYSSLISYEEDQRQGA

EPRKNFVKPNETKTYFWKVQHHMAPTKDEFDCKAWAYFSDVDLEKDVHSG

LIGPLLVCHTNTLNPAHGRQVTVQEFALFFTIFDETKSWYFTENMERNCR
```

-continued

APCNIQMEDPTFKENYRFHAINGYIMDTLPGLVMAQDQRIRWYLLSMGSN

ENIHSIHFSGHVFTVRKKEEYKMALYNLYPGVFETVEMLPSKAGIWRVEC

LIGEHLHAGMSTLFLVYSNKCQTPLGMASGHIRDFQITASGQYGQWAPKL

ARLHYSGSINAWSTKEPFSWIKVDLLAPMIIHGIKTQGARQKFSSLYISQ

FIIMYSLDGKKWQTYRGNSTGTLMVFFGNVDSSGIKHNIFNPPIIARYIR

LHPTHYSIRSTLRMELMGCDLNSCSMPLGMESKAISDAQITASSYFTNMF

ATWSPSKARLHLQGRSNAWRPQVNNPKEWLQVDFQKTMKVTGVTTQGVKS

LLTSMYVKEFLISSSQDGHQWTLFFQNGKVKVFQGNQDSFTPVVNSLDPP

LLTRYLRIHPQSWVHQIALRMEVLGCEAQDLY

The following sequence corresponds to the nucleic acid sequence of SEQ ID No: 3, i.e. to the nucleic acid sequence encoding human BDD-Factor VIII:

GCCACCAGAAGATACTACCTGGGTGCAGTGGAACTGTCATGGGACTATAT

GCAAAGTGATCTCGGTGAGCTGCCTGTGGACGCAAGATTTCCTCCTAGAG

TGCCAAAATCTTTTCCATTCAACACCTCAGTCGTGTACAAAAAGACTCTG

TTTGTAGAATTCACGGTTCACCTTTTCAACATCGCTAAGCCAAGGCCACC

CTGGATGGGTCTGCTAGGTCCTACCATCCAGGCTGAGGTTTATGATACAG

TGGTCATTACACTTAAGAACATGGCTTCCCATCCTGTCAGTCTTCATGCT

GTTGGTGTATCCTACTGGAAAGCTTCTGAGGGAGCTGAATATGATGATCA

GACCAGTCAAAGGGAGAAAGAAGATGATAAAGTCTTCCCTGGTGGAAGCC

ATACATATGTCTGGCAGGTCCTGAAAGAGAATGGTCCAATGGCCTCTGAC

CCACTGTGCCTTACCTACTCATATCTTTCTCATGTGGACCTGGTAAAAGA

CTTGAATTCAGGCCTCATTGGAGCCCTACTAGTATGTAGAGAAGGGAGTC

TGGCCAAGGAAAAGACACAGACCTTGCACAAATTTATACTACTTTTTGCT

GTATTTGATGAAGGGAAAAGTTGGCACTCAGAAACAAAGAACTCCTTGAT

GCAGGATAGGGATGCTGCATCTGCTCGGGCCTGGCCTAAAATGCACACAG

TCAATGGTTATGTAAACAGGTCTCTGCCAGGTCTGATTGGATGCCACAGG

AAATCAGTCTATTGGCATGTGATTGGAATGGGCACCACTCCTGAAGTGCA

CTCAATATTCCTCGAAGGTCACACATTTCTTGTGAGGAACCATCGCCAGG

CGTCCTTGGAAATCTCGCCAATAACTTTCCTTACTGCTCAAACACTCTTG

ATGGACCTTGGACAGTTTCTACTGTTTTGTCATATCTCTTCCCACCAACA

TGATGGCATGGAAGCTTATGTCAAAGTAGACAGCTGTCCAGAGGAACCCC

AACTACGAATGAAAAATAATGAAGAAGCGGAAGACTATGATGATGATCTT

ACTGATTCTGAAATGGATGTGGTCAGGTTTGATGATGACAACTCTCCTTC

CTTTATCCAAATTCGCTCAGTTGCCAAGAAGCATCCTAAAACTTGGGTAC

ATTACATTGCTGCTGAAGAGGAGGACTGGGACTATGCTCCCTTAGTCCTC

GCCCCCGATGACAGAAGTTATAAAAGTCAATATTTGAACAATGGCCCTCA

GCGGATTGGTAGGAAGTACAAAAAAGTCCGATTTATGGCATACACAGATG

AAACCTTTAAGACTCGTGAAGCTATTCAGCATGAATCAGGAATCTTGGGA

CCTTTACTTTATGGGGAAGTTGGAGACACACTGTTGATTATATTTAAGAA

TCAAGCAAGCAGACCATATAACATCTACCCTCACGGAATCACTGATGTCC

GTCCTTTGTATTCAAGGAGATTACCAAAAGGTGTAAAACATTTGAAGGAT

TTTCCAATTCTGCCAGGAGAAATATTCAAATATAAATGGACAGTGACTGT

AGAAGATGGGCCAACTAAATCAGATCCTCGGTGCCTCACCCGCTATTACT

CTAGTTTCGTTAATATGGAGAGAGATCTAGCTTCAGGACTCATTGGCCCT

CTCCTCATCTGCTACAAAGAATCTGTAGATCAAAGAGGGAAACCACATAAT

GTCAGACAAGAGGAATGTCATCCTGTTTTCTGTATTTGATGAGAACCGAA

GCTGGTACCTCACAGAGAATATACAACGCTTTCTCCCCAATCCAGCTGGA

GTGCAGCTTGAGGATCCAGAGTTCCAAGCCTCCAACATCATGCACAGCAT

CAATGGCTATGTTTTGATAGTTTGCAGTTGTCAGTTTGTTTGCATGAGG

TGGCATACTGGTACATTCTAAGCATTGGAGCACAGACTGACTTCCTTTCT

GTCTTCTTCTCTGGATATACCTTCAAACACAAAATGGTCTATGAAGACAC

ACTCACCCTATTCCCATTCTCAGGAGAAACTGTCTTCATGTCGATGGAAA

ACCCAGGTCTATGGATTCTGGGGTGCCACAACTCAGACTTTCGGAACAGA

GGCATGACCGCCTTACTGAAGGTTTCTAGTTGTGACAAGAACACTGGTGA

TTATTACGAGGACAGTTATGAAGATATTTCAGCATACTTGCTGAGTAAAA

ACAATGCCATTGAACCAAGAGAAATAACTCGTACTACTCTTCAGTCAGAT

CAAGAGGAAATTGACTATGATGATACCATATCAGTTGAAATGAAGAAGGA

AGATTTTGACATTTATGATGAGGATGAAAATCAGAGCCCCCGCAGCTTTC

AAAAGAAAACACGACACTATTTTATTGCTGCAGTGGAGAGGCTCTGGGAT

TATGGGATGAGTAGCTCCCCACATGTTCTAAGAAACAGGGCTCAGAGTGG

CAGTGTCCCTCAGTTCAAGAAAGTTGTTTTCCAGGAATTTACTGATGGCT

CCTTTACTCAGCCCTTATACCGTGGAGAACTAAATGAACATTTGGGACTC

CTGGGGCCATATATAAGAGCAGAAGTTGAAGATAATATCATGGTAACTTT

CAGAAATCAGGCCTCTCGTCCCTATTCCTTCTATTCTAGCCTTATTTCTT

ATGAGGAAGATCAGAGGCAAGGAGCAGAACCTAGAAAAAACTTTGTCAAG

CCTAATGAAACCAAAACTTACTTTTGGAAAGTGCAACATCATATGGCACC

CACTAAAGATGAGTTTGACTGCAAAGCCTGGGCTTATTTCTCTGATGTTG

ACCTGGAAAAGATGTGCACTCAGGCCTGATTGGACCCCTTCTGGTCTGC

CACACTAACACACTGAACCCTGCTCATGGGAGACAAGTGACAGTACAGGA

ATTTGCTCTGTTTTTCACCATCTTTGATGAGACCAAAAGCTGGTACTTCA

CTGAAAATATGGAAAGAAACTGCAGGGCTCCCTGCAATATCCAGATGGAA

GATCCCACTTTTAAAGAGAATTATCGCTTCCATGCAATCAATGGCTACAT

AATGGATACACTACCTGGCTTAGTAATGGCTCAGGATCAAAGGATTCGAT

GGTATCTGCTCAGCATGGGCAGCAATGAAAACATCCATTCTATTCATTTC

AGTGGACATGTGTTCACTGTACGAAAAAAAGAGGAGTATAAAATGGCACT

GTACAATCTCTATCCAGGTGTTTTTGAGACAGTGGAAATGTTACCATCCA

AAGCTGGAATTTGGCGGGTGGAATGCCTTATTGGCGAGCATCTACATGCT

GGGATGAGCACTTTTTCTGGTGTACAGCAATAAGTGTCAGACTCCCCT

GGGAATGGCTTCTGGACACATTAGAGATTTTCAGATTACAGCTTCAGGAC

AATATGGACAGTGGGCCCCAAAGCTGGCCAGACTTCATTATTCCGGATCA

-continued

```
ATCAATGCCTGGAGCACCAAGGAGCCCTTTTCTTGGATCAAGGTGGATCT
GTTGGCACCAATGATTATTCACGGCATCAAGACCCAGGGTGCCCGTCAGA
AGTTCTCCAGCCTCTACATCTCTCAGTTTATCATCATGTATAGTCTTGAT
GGGAAGAAGTGGCAGACTTATCGAGGAAATTCCACTGGAACCTTAATGGT
CTTCTTTGGCAATGTGGATTCATCTGGGATAAAACACAATATTTTTAACC
CTCCAATTATTGCTCGATACATCCGTTTGCACCCAACTCATTATAGCATT
CGCAGCACTCTTCGCATGGAGTTGATGGGCTGTGATTTAAATAGTTGCAG
CATGCCATTGGGAATGGAGAGTAAAGCAATATCAGATGCACAGATTACTG
CTTCATCCTACTTTACCAATATGTTTGCCACCTGGTCTCCTTCAAAAGCT
CGACTTCACCTCCAAGGGAGGAGTAATGCCTGGAGACCTCAGGTGAATAA
TCCAAAAGAGTGGCTGCAAGTGGACTTCCAGAAGACAATGAAAGTCACAG
GAGTAACTACTCAGGGAGTAAAATCTCTGCTTACCAGCATGTATGTGAAG
GAGTTCCTCATCTCCAGCAGTCAAGATGGCCATCAGTGGACTCTCTTTTT
TCAGAATGGCAAAGTAAAGGTTTTTCAGGGAAATCAAGACTCCTTCACAC
CTGTGGTGAACTCTCTAGACCCACCGTTACTGACTCGCTACCTTCGAATT
CACCCCCAGAGTTGGGTGCACCAGATTGCCCTGAGGATGGAGGTTCTGGG
CTGCGAGGCACAGGACCTCTACTGA
```

The following sequence corresponds to the amino acid sequence of SEQ ID No: 4, i.e. to the amino acid sequence of human BDD-Factor VIII:

```
ATRRYYLGAVELSWDYMQSDLGELPVDARFPPRVPKSFPFNTSVVYKKTL
FVEFTVHLFNIAKPRPPWMGLLGPTIQAEVYDTVVITLKNMASHPVSLHA
VGVSYWKASEGAEYDDQTSQREKEDDKVFPGGSHTYVWQVLKENGPMASD
PLCLTYSYLSHVDLVKDLNSGLIGALLVCREGSLAKEKTQTLHKFILLFA
VFDEGKSWHSETKNSLMQDRDAASARAWPKMHTVNGYVNRSLPGLIGCHR
KSVYWHVIGMGTTPEVHSIFLEGHTFLVRNHRQASLEISPITFLTAQTLL
MDLGQFLLFCHISSHQHDGMEAYVKVDSCPEEPQLRMKNNEEAEDYDDDL
TDSEMDVVRFDDDNSPSFIQIRSVAKKHPKTWVNYIAAEEEDWDYAPLVL
APDDRSYKSQYLNNGPQRIGRKYKKVRFMAYTDETFKTREAIQHESGILG
PLLYGEVGDTLLIIFKNQASRPYNIYPHGITDVRPLYSRRLPKGVKHLKD
FPILPGEIFKYKWTVTVEDGPTKSDPRCLTRYYSSFVNMERDLASGLIGP
LLICYKESVDQRGNQIMSDKRNVILFSVFDENRSWYLTENIQRFLPNPAG
VQLEDPEFQASNIMHSINGYVFDSLQLSVCLHEVAYWYILSIGAQTDFLS
VFFSGYTFKHKMVYEDTLTLFPFSGETVFMSMENPGLWILGCHNSDFRNR
GMTALLKVSSCDKNTGDYYEDSYEDISAYLLSKNNAIEPREITRTTLQSD
QEEIDYDDTISVEMKKEDFDIYDEDENQSPRSFQKKTRHYFIAAVERLWD
YGMSSSPHVLRNRAQSGSVPQFKKVVFQEFTDGSFTQPLRYGELNEHLGL
LGPYIRAEVEDNIMVTFRNQASRPYSFYSSLISYEEDQRQGAEPRKNFVK
PNETKTYFWKVQHHMAPTKDEFDCKAWAYFSDVDLEKDVHSGLIGPLLVC
HTNTLNPAHGRQVTVQEFALFFTIFDETKSWYFTENMERNCRAPCNIQME
DPTFKENYRFHAINGYIMDTLPGLVMAQDQRIRWYLLSMGSNENIHSIHF
SGHVFTVRKKEEYKMALYNLYPGVFETVEMLPSKAGIWRVECLIGEHLHA
GMSTLFLVYSNKCQTPLGMASGHIRDFQITASGQYGQWAPKLARLHYSGS
INAWSTKEPFSWIKVDLLAPMIIHGIKTQGARQKFSSLYISQFIIMYSLD
GKKWQTYRGNSTGTLMVFFGNVDSSGIKHNIFNPPIIARYIRLHPTHYSI
RSTLRMELMGCDLNSCSMPLGMESKAISDAQITASSYFTNMFATWSPSKA
RLHLQGRSNAWRPQVNNPKEWLQVDFQKTMKVTGVTTQGVKSLLTSMYVK
EFLISSSQDGHQWTLFPQNGKVKVFQGNQDSFTPVVNSLDPPLLTRYLRI
HPQSWVHQIALRMEVLGCEAQDLY
```

The following sequence corresponds to the nucleic acid sequence of SEQ ID No: 5, i.e. to the nucleic acid sequence encoding the heavy chain comprising the mutation Asn239Ala of human Factor VIII:

```
GCCACCAGAAGATACTACCTGGGTGCAGTGGAACTGTCATGGGACTATAT
GCAAAGTGATCTCGGTGAGCTGCCTGTGGACGCAAGATTTCCTCCTAGAG
TGCCAAAATCTTTTCCATTCAACACCTCAGTCGTGTACAAAAAGACTCTG
TTTGTAGAATTCACGGTTCACCTTTTCAACATCGCTAAGCCAAGGCCACC
CTGGATGGGTCTGCTAGGTCCTACCATCCAGGCTGAGGTTTATGATACAG
TGGTCATTACACTTAAGAACATGGCTTCCCATCCTGTCAGTCTTCATGCT
GTTGGTGTATCCTACTGGAAAGCTTCTGAGGGAGCTGAATATGATGATCA
GACCAGTCAAAGGGAGAAAGAAGATGATAAAGTCTTCCCTGGTGGAAGCC
ATACATATGTCTGGCAGGTCCTGAAAGAGAATGGTCCAATGGCCTCTGAC
CCACTGTGCCTTACCTACTCATATCTTTCTCATGTGGACCTGGTAAAAGA
CTTGAATTCAGGCCTCATTGGAGCCCTACTAGTATGTAGAGAAGGGAGTC
TGGCCAAGGAAAAGACACAGACCTTGCACAAATTTATACTACTTTTTGCT
GTATTTGATGAAGGGAAAAGTTGGCACTCAGAAACAAAGAACTCCTTGAT
GCAGGATAGGGATGCTGCATCTGCTCGGGCCTGGCCTAAAATGCACACAG
TCAATGGTTATGTAGCCACCTCTCTGCCAGGTCTGATTGGATGCCACAGG
AAATCAGTCTATTGGCATGTGATTGGAATGGGCACCACTCCTGAAGTGCA
CTCAATATTCCTCGAAGGTCACACATTTCTTGTGAGGAACCATCGCCAGG
CGTCCTTGGAAATCTCGCCAATAACTTTCCTTACTGCTCAAACACTCTTG
ATGGACCTTGGACAGTTTCTACTGTTTTGTCATATCTCTTCCCACCAACA
TGATGGCATGGAAGCTTATGTCAAAGTAGACAGCTGTCCAGAGGAACCCC
AACTACGAATGAAAAATAATGAAGAAGCGGAAGACTATGATGATGATCTT
ACTGATTCTGAAATGGATGTGGTCAGGTTTGATGATGACAACTCTCCTTC
CTTTATCCAAATTCGCTCAGTTGCCAAGAAGCATCCTAAAACTTGGGTAC
ATTACATTGCTGCTGAAGAGGAGGACTGGGACTATGCTCCCTTAGTCCTC
GCCCCCGATGACAGAAGTTATAAAAGTCAATATTTGAACAATGGCCCTCA
GCGGATTGGTAGGAAGTACAAAAAAGTCCGATTTATGGCATACACAGATG
AAACCTTTAAGACTCGTGAAGCTATTCAGCATGAATCAGGAATCTTGGGA
CCTTTACTTTATGGGGAAGTTGGAGACACACTGTTGATTATATTTAAGAA
```

-continued

```
TCAAGCAAGCAGACCATATAACATCTACCCTCACGGAATCACTGATGTCC

GTCCTTTGTATTCAAGGAGATTACCAAAAGGTGTAAAACATTTGAAGGAT

TTTCCAATTCTGCCAGGAGAAATATTCAAATATAAATGGACAGTGACTGT

AGAAGATGGGCCAACTAAATCAGATCCTCGGTGCCTGACCCGCTATTACT

CTAGTTTCGTTAATATGGAGAGAGATCTAGCTTCAGGACTCATTGGCCCT

CTCCTCATCTGCTACAAAGAATCTGTAGATCAAAGAGGAAACCAGATAAT

GTCAGACAAGAGGAATGTCATCCTGTTTTCTGTATTTGATGAGAACCGAA

GCTGGTACCTCACAGAGAATATACAACGCTTTCTCCCCAATCCAGCTGGA

GTGCAGCTTGAGGATCCAGAGTTCCAAGCCTCCAACATCATGCACAGCAT

CAATGGCTATGTTTTTGATAGTTTGCAGTTGTCAGTTTGTTTGCATGAGG

TGGCATACTGGTACATTCTAAGCATTGGAGCACAGACTGACTTCCTTTCT

GTCTTCTTCTCTGGATATACCTTCAAACACAAAATGGTCTATGAAGACAC

ACTCACCCTATTCCCATTCTCAGGAGAAACTGTCTTCATGTCGATGGAAA

ACCCAGGTCTATGGATTCTGGGGTGCCACAACTCAGACTTTCGGAACAGA

GGCATGACCGCCTTACTGAAGGTTTCTAGTTGTGACAAGAACACTGGTGA

TTATTACGAGGACAGTTATGAAGATATTTCAGCATACTTGCTGAGTAAAA

ACAATGCCATTGAACCAAGA
```

The following sequence corresponds to the amino acid sequence of SEQ ID No: 6, i.e. to the amino acid sequence of the heavy chain comprising the mutation Asn239Ala of human Factor VIII:

```
ATRRYYLGAVELSWDYMQSDLGELPVDARFPPRVPKSFPFNTSVVYKKTL

FVEFTVHLFNIAKPRPPWMGLLGPTIQAEVYDTVVITLKNMASHPVSLHA

VGVSYWKASEGAEYDDQTSQREKEDDKVFFGGSHTYVWQVLKENGPMASD

PLCLTYSYLSHVDLVKDLNSGLIGALLVCREGSLAKEKTQTLHKFILLFA

VFDEGKSWHSETKNSLMQDRDAASARAWPKMHTVNGYVARSLPGLIGCHR

KSVYWHVIGMGTTPEVHSIFLEGHTFLVRNHRQASLEISPITFLTAQTLL

MDLGQFLLFCHISSHQHDGMEAYVKVDSCPEEPQLRMKNNEEAEDYDDDL

TDSEMDVVRFDDDNSPSFIQIRSVAKKHPRTWVHYIAAEEEDWDYAPLVL

APDDRSYKSQYLNNGPQRIGRKYKKVRFMAYTDETFKTREAIQHESGILG

PLLYGEVGDTLLIIFKNQASRPYNIYPHGITDVRPLYSRRLPKGVKHLKD

FPILPGEIFKYKWTVTVEDGPTKSDPRCLTRYYSSFVNMERDLASGLIGP

LLICYKESVDQRGNQIMSDKRNVILFSVFDENRSWYLTENIQRFLPNPAG

VQLEDPEFQASNIMHSINGYVFDSLQLSVCLHEVAYWYILSIGAQTDFLS

VFFSGYTFKHKMVYEDTLTLFPPFSGETVFMSMENPGLWILGCHNSDFRNR

GMTALLKVSSCDKNTGDYYEDSYEDISAYLLSKNNAIEPR
```

The following sequence corresponds to the nucleic acid sequence of SEQ ID No: 7, i.e, to the nucleic acid sequence encoding the light chain comprising the mutation Asn2118Ala of human Factor VIII:

```
AGCTTTCAAAAGAAAACACGACACTATTTTATTGCTGCAGTGGAGAGGCT

CTGCGATTATGGGATGAGTAGCTCCCCACATGTTCTAAGAAACAGGGCTC

AGAGTGGCAGTGTCCCTCAGTTCAAGAAAGTTGTTTTCCAGGAATTTACT

GATGGCTCCTTTACTCAGCCCTTATACCGTGGAGAACTAAATGAACATTT

GGGACTCCTGGGGCCATATATAAGAGCAGAAGTTGAAGATAATATCATGG

TAACTTTCAGAAATCAGGCCTCTCGTCCCTATTCCTTCTATTCTAGCCTT

ATTTCTTATGAGGAAGATCAGAGGCAAGGAGCAGAACCTAGAAAAAACTT

TGTCAAGCCTAATGAAACCAAAACTTACTTTTGGAAAGTGCAACATCATA

TGGCACCCACTAAAGATGAGTTTGACTGCAAAGCCTGGGCTTATTTCTCT

GATGTTGACCTGGAAAAGATGTGCACTCAGGCCTGATTGGACCCCTTCT

GGTCTGCCACACTAACACACTGAACCCTGCTCATGGGAGACAAGTGACAG

TACAGGAATTTGCTCTGTTTTCACCATCTTTGATGAGACCAAAAGCTGG

TACTTCACTGAAAATATGGAAAGAAACTGCAGGGCTCCCTGCAATATCCA

GATGGAAGATCCCACTTTTAAAGAGAATTATCGCTTCCATGCAATCAATG

GCTACATAATGGATACACTACCTGGCTTAGTAATGGCTCAGGATCAAAGG

ATTCGATGGTATCTGCTCAGCATGGGCAGCAATGAAAACATCCATTCTAT

TCATTTCAGTGGACATGTGTTCACTGTACGAAAAAAAGAGGAGTATAAAA

TGGCACTGTACAATCTCTATCCAGGTGTTTTTGAGACAGTGGAAATGTTA

CCATCCAAAGCTGGAATTTGGCGGGTGGAATGCCTTATTGGCGAGCATCT

ACATGCTGGGATGAGCACACTTTTTCTGGTGTACAGCAATAAGTGTCAGA

CTCCCCTGGGAATGGCTTCTGGACACATTAGAGATTTTCAGATTACAGCT

TCAGGACAATATGGACAGTGGGCCCCAAAGCTGGCCAGACTTCATTATTC

CGGATCAATCAATGCCTGGAGCACCAAGGAGCCCTTTTCTTGGATCAAGG

TGGATCTGTTGGCACCAATGATTATTCACGGCATCAAGACCCAGGGTGCC

CGTCAGAAGTTCTCCAGCCTCTACATCTCTCAGTTTATCATCATGTATAG

TCTTGATGGGAAGAAGTGGCAGACTTATCGAGGAGCCTCCACTGGAACCT

TAATGGTCTTCTTTGGCAATGTGGATTCATCTGGGATAAAACACAATATT

TTTAACCCTCCAATTATTGCTCGATACATCCGTTTGCACCCAACTCATTA

TAGCATTCGCAGCACTCTTCGCATGGAGTTGATGGGCTGTGATTTAAATA

GTTGCAGCATGCCATTGGGAATGGAGAGTAAAGCAATATCAGATGCACAG

ATTACTGCTTCATCCTACTTTACCAATATGTTTGCCACCTGGTCTCCTTC

AAAAGCTCGACTTCACCTCCAAGGGAGGAGTAATGCCTGGAGACCTCAGG

TGAATAATCCAAAAGAGTGGCTGCAAGTGGACTTCCAGAAGACAATGAAA

GTCACAGGAGTAACTACTCAGGGAGTAAAATCTCTGCTTACCAGCATGTA

TGTGAAGGAGTTCCTCATCTCCAGCAGTCAAGATGGCCATCAGTGGACTC

TCTTTTTTCAGAATGGCAAAGTAAAGGTTTTTCAGGGAAATCAAGACTCC

TTCACACCTGTGGTGAACTCTCTAGACCCACCGTTACTGACTCGCTACCT

TCGAATTCACCCCCAGAGTTGGGTGCACCAGATTGCCCTGAGGATGGAGG

TTCTGGGCTGCGAGGCACAGGACCTCTACTGA
```

The following sequence corresponds to the amino acid sequence of SEQ ID No: 8, i.e. to the amino acid sequence of the light chain comprising the mutation Asn2118Ala of human Factor VIII:

SFQKKTRHYFIAAVERLWDYGMSSSPHVLRNRAQSGSVPQFKKVVFQEFT
DGSFTQPLYRGELNEHLGLLGPYIRAEVEDNIMVTFRNQASRPYSFYSSL
ISYEEDQRQGAEPRKNFVKPNETKTYFWKVQHHMAPTKDEFDCKAWAYFS
DVDLEKDVHSGLIGPLLVCHTNTLNPAHGRQVTVQEFALFFTIFDETKSW
YFTENMERNCRAPCNIQMEDPTFKENYRFHAINGYIMDTLPGLVMAQDQR
IRWYLLSMGSNENIHSIHFSGHVFTVRKKEEYKMALYNLYPGVFETVEML
PSKAGIWRVECLIGEHLHAGMSTLFLVYSNKCQTPLGMASGHIRDFQITA
SGQYGQWAPKLARLHYSGSINAWSTKEPFSWIKVDLLAPMIIHGIKTQGA
RQKFSSLYISQFIIMYSLDGKKWQTYRGASTGTLMVFFGNVDSSGIKHNI
FNPPIIARYIRLHPTHYSIRSTLRMELMGCDLNSCSMPLGMESKAISDAQ
ITASSYFTNMFATWSPSKARLHLQGRSNAWRPQVNNPKEWLQVDFQKTMK
VTGVTTQGVKSLLTSMYVKEFLISSSQDGHQWTLFFQNGKVKVFQGNQDS
FTPVVNSLDPPLLTRYLRIHPQSWVHQIALRMEVLGCEAQDLY

The following sequence corresponds to the amino acid sequence of SEQ ID No: 9, i.e. to the amino acid sequence of the I$^{2144}$-T$^{2161}$ polypeptide:
IIARYIRLHPTHYSIRST The following sequence corresponds to the amino acid sequence of SEQ ID No: 10, i.e. to the amino acid sequence of B domain of full-length human Factor VIII:

SFSQNSRHPSTRQKQFNATTIPENDIEKTDPWFAHRTPMPKIQNVSSSDL
LMLLRQSPTPHGLSLSDLQEAKYETFSDDPSPGAIDSNNSLSEMTHFRPQ
LHHSGDMVFTPESGLQLRLNEKLGTTAATELKKLDFKVSSTSNNLISTIP
SDNLAAGTDNTSSLGPPSMPVHYDSQLDTTLFGKKSSPLTESGGPLSLSE
ENNDSKLLESGLMNSQESSWGKNVSSTESGRLFKGKRAHGPALLTKDNAL
FKVSISLLKTNKTSNNSATNRKTHIDGPSLLIENSPSVWQNILESDTEFK
KVTPLIHDRMLMDKNATALRLNHMSNKTTSSKNMEMVQQKKEGPIPPDAQ
NPDNSFFKMLFLPESARWIQRTHGKNSLNSGQGPSPKQLVSLGPEKSVEG
QNFLSEKNKVVVGKGEFTKDVGLKEMVFPSSRNLFLTNLDNLHENNTHNQ
EKKIQEEIEKKETLIQENVVLPQIHTVTGTKNFMKNLFLLSTRQNVEGSY
DGAYAPVLQDFRSLNDSTNRTKKHTAHFSKKGEEENLEGLGNQTKQIVEK
YACTTRISPNTSQQNFVTQRSKR

The following sequence corresponds to the nucleic acid sequence of SEQ ID No: 11, i.e, to the nucleic acid sequence encoding the heavy chain comprising the mutation Asn239Gln of human Factor VIII:

GCCACCAGAAGATACTACCTGGGTGCAGTGGAACTGTCATGGGACTATAT
GCAAAGTGATCTCGGTGAGCTGCCTGTGGACGCAAGATTTCCTCCTAGAG
TGCCAAAATCTTTTCCATTCAACACCTCAGTCGTGTACAAAAAGACTCTG
TTTGTAGAATTCACGGTTCACCTTTTCAACATCGCTAAGCCAAGGCCACC
CTGGATGGGTCTGCTAGGTCCTACCATCCAGGCTGAGGTATATGATACAG
TGGTCATTACACTTAAGAACATGGCTTCCCATCCTGTCAGTCTTCATGCT
GTTGGTGTATCCTACTGGAAAGCTTCTGAGGGAGCTGAATATGATGATCA
GACCAGTCAAAGGGAGAAAGAAGATGATAAAGTCTTCCCTGGTGGAAGCC
ATACATATGTCTGGCAGGTCCTGAAAGAGAATGGTCCAATGGCCTCTGAC
CCACTGTGCCTTACCTACTCATATCTTTCTCATGTGGACCTGGTAAAAGA
CTTGAATTCAGGCCTCATTGGAGCCCTACTAGTATGTAGAGAAGGGAGTC
TGGCCAAGGAAAAGACACAGACCTTGCACAAATTTATACTACTTTTTGCT
GTATTTGATGAAGGGAAAAGTTGGCACTCAGAAACAAAGAACTCCTTGAT
GCAGGATAGGGATGCTGCATCTGCTCGGGCCTGGCCTAAAATGCACACAG
TCAATGGTTATGTACAGAGGTCTCTGCCAGGTCTGATTGGATGCCACAGG
AAATCAGTCTATTGGCATGTGATTGGAATGGGCACCACTCCTGAAGTGCA
CTCAATATTCCTCGAAGGTCACACATTTCTTGTGAGGAACCATCGCCAGG
CGTCCTTGGAAATCTCGCCAATAACTTTCCTTACTGCTCAAACACTCTTG
ATGGACCTTGGACAGTTTCTACTGTTTTGTCATATCTCTTCCCACCAACA
TGATGGCATGGAAGCTTATGTCAAAGTAGACAGCTGTCCAGAGGAACCCC
AACTACGAATGAAAAATAATGAAGAAGCGGAAGACTATGATGATGATCTT
ACTGATTCTGAAATGGATGTGGTCAGGTTTGATGATGACAACTCTCCTTC
CTTTATCCAAATTCGCTCAGTTGCCAAGAAGCATCCTAAAACTTGGGTAC
ATTACATTGCTGCTGAAGAGGAGGACTGGGACTATGCTCCCTTAGTCCTC
GCCCCCGATGACAGAAGTTATAAAAGTCAATATTTGAACAATGGCCCTCA
GCGGATTGGTAGGAAGTACAAAAAAGTCCGATTTATGGCATACACAGATG
AAACCTTTAAGACTCGTGAAGCTATTCAGCATGAATCAGGAATCTTGGGA
CCTTTACTTTATGGGGAAGTTGGAGACACACTGTTGATTATATTTAAGAA
TCAAGCAAGCAGACCATATAACATCTACCCTCACGGAATCACTGATGTCC
GTCCTTTGTATTCAAGGAGATTACCAAAAGGTGTAAAACATTTGAAGGAT
TTTCCAATTCTGCCAGGAGAAATATTCAAATATAAATGGACAGTGACTGT
AGAAGATGGGCCAACTAAATCAGATCCTCGGTCCCTGACCCGCTATTACT
CTAGTTTCGTTAATATGGAGAGAGATCTAGCTTCAGGACTCATTGGCCCT
CTCCTCATCTGCTACAAAGAATCTGTAGATCAAAGAGGAAACCAGATAAT
GTCAGACAAGAGGAATGTCATCCTGTTTTCTGTATTTGATGAGAACCGAA
GCTGGTACCTCACAGAGAATATACAACGCTTTCTCCCCAATCCAGCTGGA
GTGCAGCTTGAGGATCCAGAGTTCCAAGCCTCCAACATCATGCACAGCAT
CAATGGCTATGTTTTTGATAGTTTGCAGTTGTCAGTTTGTTTGCATGAGG
TGGCATACTGGTACATTCTAAGCATTGGAGCACAGACTGACTTCCTTTCT
GTCTTCTTCTCTGGATATACCTTCAAACACAAAATGGTCTATGAAGACAC
ACTCACCCTATTCCCATTCTCAGGAGAAACTGTCTTCATGTCGATGGAAA
ACCCAGGTCTATGGATTCTGGGGTGCCACAACTCAGACTTTCGGAACAGA
GGCATGACCGCCTTACTGAAGGTTTCTAGTTGTGACAAGAACACTGGTGA

TTATTACGAGGACAGTTATGAAGATATTTCAGCATACTTGCTGAGTAAAA

ACAATGCCATTGAACCAAGA

The following sequence correspond to the amino acid sequence of SEQ ID NO: 12, i.e. to the amino acid sequence of the heavy chain comprising the mutation Asn239Gln of human Factor VIII:

ATRRYYLGAVELSWDYMQSDLGELPVDARFPPRVPKSFPFNTSVVYKKTL

FVEFTVHLFNIAKPRPPWMGLLGPTIQAEVYDTVVITLKNMASHPVSLHA

VGVSYWKASEGAEYDDQTSQREKEDDKVFPGGSHTYVWQVLKENGPMASD

PLCLTYSYLSHVDLVKDLNSGLIGALLVCREGSLAYEKTQTLHKFILLFA

VFDEGKSWHSETKNSLMQDRDAASARAWPKMHTVNGYVQRSLPGLIGCHR

KSVYWHVIGMGTTPEVHSIFLEGHTFLVRNHRQASLEISFITFLTAQTLL

MDLGQFLLFCHISSHQHDGMEAYVKVDSCPEEPQLRMKNNEEAEDYDDDL

TDSEMDVVRFDDDNSPSFIQIRSVAKKHPKTWVHYIAAEEEDWDYAPLVL

APDDRSYKSQYLNNGPQRIGRKYKKVRFMAYTDETFKTREAIQHESGILG

PLLYGEVGDTLLIIFKNQASRPYNIYPHGITDVRPLYSRRLPKGVKHLKD

FPILPGEIFKYKWTVTVEDGPTKSDPRCLTRYYSSFVNMERDLASGLIGP

LLICYKESVDQRGNQIMSDKRNVILFSVFDENRSWYLTENIQRFLPNPAG

VQLEDPEFQASNIMHSINGYVFDSLQLSVCLHEVAYWYILSIGAQTDFLS

VFFSGYTFKHKMVYEDTLTLFPFSGETVFMSMENPGLWILGCHNSDFRNR

GMTALLKVSSCDKNTGDYYEDSYEDISAYLLSKNNAIEPR

The following sequence corresponds to the nucleic acid sequence of SEQ ID No: 13, i.e. to the nucleic acid sequence encoding the light chain comprising the mutation Asn2118Gln of human Factor VIII:

AGCTTTCAAAAGAAAACACGACACTATTTTATTGCTGCAGTGGAGAGGCT

CTGGGATTATGGGATGAGTAGCTCCCCACATGTTCTAACAAACAGGGCTC

AGAGTGGCAGTGTCCCTCAGTTCAAGAAAGTTGTTTTCCAGGAATTTACT

GATGGCTCCTTTACTCAGCCCTTATACCGTGGAGAACTAAATGAACATTT

GGGACTCCTGGGGCCATATATAAGAGCAGAAGTTGAAGATAATATCATGG

TAACTTTCAGAAATCAGGCCTCTCGTCCCTATTCCTTCTATTCTAGCCTT

ATTTCTTATGAGGAAGATCAGAGGCAAGGAGCAGAACCTAGAAAAACTT

TGTCAAGCCTAATGAAACCAAAACTTACTTTTGGAAAGTGCAACATCATA

TGGCACCCACTAAAGATGAGTTTGACTGCAAAGCCTGGGCTTATTTCTCT

GATGTTGACCTGGAAAAAGATGTGCACTCAGGCCTGATTGGACCCCTTCT

GGTCTGCCACACTAACACACTGAACCCTGCTCATGGGAGACAAGTGACAG

TACAGGAATTTGCTCTGTTTTTCACCATCTTTGATGAGACCAAAAGCTGG

TACTTCACTGAAAATATGGAAAGAAACTGCAGGGCTCCCTGCAATATCCA

GATGGAAGATCCCACTTTTAAAGAGAATTATCGCTTCCATGCAATCAATG

GCTACATAATGGATACACTACCTGGCTTAGTAATGGCTCAGGATCAAAGG

ATTCGATGGTATCTGCTCAGCATGGGCAGCAATGAAAACATCCATTCTAT

TCATTTCAGTGGACATGTGTTCACTGTACGAAAAAAAGAGGAGTATAAAA

TGGCACTGTACAATCTCTATCCAGGTGTTTTTGAGACAGTGGAAATGTTA

CCATCCAAAGCTGGAATTTGGCGGGTGGAATGCCTTATTGGCGAGCATCT

ACATGCTGGGATGAGCACACTTTTTCTGGTGTACAGCAATAAGTGTCAGA

CTCCCCTGGGAATGGCTTCTGGACACATTAGAGATTTTCAGATTACAGCT

TCAGGACAATATGGACAGTGGGCCCCAAAGCTGGCCAGACTTCATTATTC

CGGATCAATCAATGCCTGGAGCACCAAGGAGCCCTTTTCTTGGATCAAGG

TGGATCTGTTGGCACCAATGATTATTCACGGCATCAAGACCCAGGGTGCC

CGTCAGAAGTTCTCCAGCCTCTACATCTCTCAGTTTATCATCATGTATAG

TCTTGATGGGAAGAAGTGGCAGACTTATCGAGGACAGTCCACTGGAACCT

TAATGGTCTTCTTTGGCAATGTGGATTCATCTGGGATAAAACACAATATT

TTTAACCCTCCAATTATTGCTCGATACATCCGTTTGCACCCAACTCATTA

TAGCATTCGCAGCACTCTTCGCATGGAGTTGATGGGCTGTGATTTAAATA

GTTGCAGCATGCCATTGGGAATGGAGAGTAAAGCAATATCAGATGCACAG

ATTACTGCTTCATCCTACTTTACCAATATGTTTGCCACCTGGTCTCCTTC

AAAAGCTCGACTTCACCTCCAAGGGAGGAGTAATGCCTGGAGACCTCAGG

TGAATAATCCAAAAGAGTGGCTGCAAGTGGACTTCCAGAAGACAATGAAA

GTCACAGGAGTAACTACTCAGGGAGTAAAATCTCTGCTTACCAGCATGTA

TGTGAAGGAGTTCCTCATCTCCAGCAGTCAAGATGGCCATCAGTGGACTC

TCTTTTTTCAGAATGGCAAAGTAAAGGTTTTTCAGGGAAATCAAGACTCC

TTCACACCTGTGGTGAACTCTCTAGACCCACCGTTACTGACTCGCTACCT

TCGAATTCACCCCCAGAGTTGGGTGCACCAGATTGCCCTGAGGATGGAGG

TTCTGGGCTGCGAGGCACAGGACCTCTACTGA

The following sequence corresponds to the amino acid sequence of SEQ ID No: 14, i.e. to the amino acid sequence of the light chain comprising the mutation Asn2118Gln of human Factor VIII:

SFQKKTRHYFIAAVERLWDYGMSSSPHVLRNRAQSGSVPQFKKVVFQEFT

DGSFTQPLYRGELNEHLGLLGPYIRAEVEDNIMVTFRNQASRPYSFYSSL

ISYEEDQRQGAEPRKNFVKPNETKTYFWKVQHHMAPTKDEFDCKAWAYFS

DVDLEKDVHSGLIGPLLVCHTNTLNPAHGRQVTVQEFALFFTIFDETKSW

YFTENMERNCRAPCNIQMEDPTFKENYRFHAINGYIMDTLPGLVMAQDQR

IRWYLLSMGSNENIHSIHFSGHVFTVRKKEEYKMALYNLYPGVFETVEML

PSKAGIWRVECLIGEHLHAGMSTLFLVYSNKCQTPLGMASGHIRDFQITA

SGQYGQWAPKLARLHYSGSINAWSTKEPFSWIKVDLLAPMIIHGIKTQGA

RQKFSSLYISQFIIMYSLDGKKWQTYRGQSTGTLMVFFGNVDSSGIKHNI

FNPPIIARYIRLHPTHYSIRSTLRMELMGCDLNSCSMPLGMESKAISDAQ

ITASSYFTNMFATWSPSKARLHLQGRSNAWRPQVNNPKEWLQVDFQKTMK

VTGVTTQGVKSLLTSMYVKEFLISSSQDGHQWTLFFQNGKVKVFQGNQDS

FTPVVNSLDPPLLTRYLRIHPQSWVHQIALRMEVTLGCEAQDLY

The present invention is not intended to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Human DCs Derived from Monocytes

Peripheral blood mononuclear cells were isolated from heparinized buffy coats of healthy adult donors by adherence to plastic cell culture dishes in RPMI 1640 medium supplemented with 10% human AB serum, glutamine and antibiotics for 60 minutes. Non-adherent cells were removed by 3 gentle washings with medium. Adherent monocytes were cultured in X-VIVO 15 (Cambrex Bio Sciences, Paris, France) supplemented with 1% human AB serum, antibiotics and in presence of 500 IU/mL recombinant human interleukin 4 (rhIL-4), R&D Systems (Lille, France) and 1000 IU/mL recombinant human granulocyte macrophage-colony-stimulating factor (rhGM-CSF), ImmunoTools (Friesoythe, Germany). Half the medium, including all supplements, was replaced every 2 days. After 5 days of culture, non-adherent and loosely adherent cells corresponding to the DC-enriched fraction were harvested, washed and used for subsequent experiments.

Example 2

Conjugation of Human Recombinant Full Length FVIII, B Domain-Deleted Human Recombinant FVIII with Fluorescein Recombinant human full length FVIII (1000 IU, Kogenate, Bayer), recombinant human B domain-deleted FVIII (BDD-FVIII, 1000 IU, Refacto®, Wyeth), were solubilized in water and dialyzed against bicarbonate buffer (pH 9.2) containing 5 mM $CaCl_2$ at 4° C. followed by coupling with fluorescein 5-isothiocyanate (isomer I, Sigma-Aldrich, Saint Quentin Fallavier, France) for 7-8 hr at 4° C. Labelled FVIII was further dialyzed against RPMI 1640 media to eliminate the uncoupled FITC. The FVIII-FITC was quantified by Bradford assay using bovine serum albumin as a standard.

Example 3

Nature of the Receptor(s) Involved in FVIII Endocytosis

Protocol

DCs were incubated for 30 min at 37° C. with either 5 mM EDTA, mannan (1 mg/ml) or galactose (1 mg/ml) prior to the addition of FVIII-FITC (40 µg/ml) for 2 hours. Endocytosis at 4° C. was used as control (not shown).

Results

FIG. 1A: endocytosis of FVIII-FITC was inhibited up to 92±16.5% (P<0.01) in the case of EDTA. This data implicates a role for bivalent ion-dependent receptors in FVIII endocytosis by DCs. The polycarbohydrate mannan, a model competitive ligand for mannose sensitive uptake, reduced the uptake of FVIII-FITC by 60±19% (P<0.01), while galactose, a competitive ligand for galactose-sensitive uptake, had no significant effect.

FIG. 1B: The specificity of mannan for mannose-sensitive CLRs was confirmed in our experimental set-up using FITC-labeled dextran, a typical ligand for mannose-sensitive CLRs, especially CD206, and lucifer yellow (LY), the internalization of which proceeds exclusively by receptor-independent macropinocytosis. Internalization of dextran was blocked by 89±9.3% in the presence of mannan, while that of LY was not affected.

Conclusion

The results indicate that mannose-sensitive receptors mediate a significant part of the endocytosis of FVIII by DCs.

Example 4

Mannose-Sensitive Uptake of FVIII by DCs Results in the Presentation FVIII-Derived Peptides to FVIII-Specific CD4+ T Cells Protocol FIG. 2A: DCs generated from MHC II-matched donors were incubated (10000 cells/well) in medium alone or in presence of mannan (1 mg/ml) or anti-CD206 IgG (10 µg/ml) followed by incubation with the FVIII-specific T cell clone D9E9 (5000 cells/well) in the presence of varying doses of full length FVIII (Kogenate®) (5.56, 2.78 or 1.39 µg/ml) and 20 U/ml rhIL-2 for 20 hr at 37° C. Activation of T cells was assessed by the release of IFN-gamma in the culture supernatant.

FIG. 2B: DCs generated from MHC II-matched donors were pre-incubated with mannan (1 mg/ml) or anti-CD206 IgG (10 µg/ml) followed by the addition of FVIII (5.56 µg/ml) or peptide I2144-T2161 (2 µg/ml) and D9E9. For each treatment, the IFN-gamma production was depicted relative to the maximum value obtained in each individual experiment (*: P<0.0001, as assessed using the Mann-Whitney test).

FIG. 1C: The human FVIII-specific HLA-matched B cell lines LE2E9, BO2C11 or DCs were incubated alone or in presence of mannan (1 mg/ml) followed by incubation with full length FVIII (Kogenate®) (10 µg/ml) and D9E9.

Results

Together, the data validate that the inhibitory effects of mannan on D9E9 activation, result from the blocking of mannose-sensitive endocytosis of FVIII by DCs.

Example 5

Exposed Mannose Residues Located Outside the B Domain Play a Significant Role in FVIII Endocytosis by DCs Leading to T Cell Activation Protocol FIG. 3A: DCs were pre-incubated with mannan (1, 5, 10, 100 and 1000 µg/ml) prior to the addition of full length FVIII-FITC (Kogenate®) (40 µg/ml, 143 nM, full circles) or BDD-FVIII-FITC (24.31 µg/ml, 143 nM, empty circles), or dextran-FITC (50 µg/ml). Uptake of the antigens was analyzed by flow cytometry. Percentage inhibition was calculated for each condition with respect to the condition without mannan.

FIG. 3B: Native or EndoF1-treated BDD-FVIII (3.7 µg) was separated by 7.5% SDS-PAGE and transferred onto a nitrocellulose membrane. Transferred proteins were revealed using Protogold® or following incubation with 10 µg/ml CTLD4-7-Fc using an alkaline phosphatase-conjugated anti-human IgG. The light chain (LCh) and heavy chain (HCh) were identified upon blotting with LCh- and HCh-specific monoclonal anti-FVIII IgGs (not shown).

FIG. 3C: Reduced activation of T cells upon EndoF1-treatment of BDD-FVIII. Results depict one representative of 3 independent experiments.

Results

Together, the data confirming the involvement of mannose-terminating glycans located outside the B domain in the uptake of FVIII.

FIG. 3B: the removal of oligomannose structures upon treatment with EndoF1 was indicated by a shift in the migration profile of BDD-FVIII and by loss of recognition by CTLD4-7-Fc.

FIG. 3C: DCs incubated with EndoF1-treated BDD-FVIII activated D9E9 to a lesser extent than those incubated with native BDD-FVIII (P<0.0001 in the case of DCs). Of note, demannosylation of BDD-FVIII was not as efficient in reducing T-cell activation as saturation of the mannose receptors on DCs using mannan. The residual ability of EndoF1-treated BDD-FVIII to activate D9E9, may be attributed to the presence of remaining N-acetyl-glucosamine residues on FVIII, which present with moderate affinity for mannose sensitive receptors.

Example 6

T Cell Activation of Modified FVIII Light Chain Asn2118Ala Protocol

The purified plasma-derived light chain of FVIII (wtLCh) kindly provided by Dr E Saenko (University of Maryland, Baltimore, Md., USA) was treated or not with Endo-F1. The wtLCh, the wtLCh in the presence of mannan (1 mg/ml) and the Endo-F1-treated wtLCh were added to DCs (FIG. 4A) or to BO2C11 (FIG. 4B), and co-cultured with D9E9 cells for 20 hr. Activation of D9E9 was assessed by measuring IFN-gamma in the culture supernatant by an ELISA. Figures C and D show the loss of activation of D9E9 upon site directed mutagenesis of the LCh-FVIII (Asn2118Ala-LCh-FVIII). The BO2C11 B cell clone and monocyte-derived DCs were incubated with D9E9 in the presence of wild-type LCh (FIG. 4C) or in the presence of mutated Asn2118Ala-LCh-FVIII (FIG. 4D). Substitution of Asn2118 by Ala residue removes a site for N-mannosylation. Activation of D9E9 was assessed after 20 hr by measuring IFN-gamma in the culture supernatant.

Results

FIGS. 4A et 4B: First, we validated that the wtLCh enters monocyte-derived DCs in a mannose-sensitive manner and activates the FVIII-specific D9E9 T cell clone. Activation of D9E9 by DCs was significantly lower in the case of wtLCh incubated with mannan and in the case of Endo-F1-treated wtLCh, than in the case of untreated wtLCh (FIG. 4A). In contrast, activation of D9E9 by the BO2C11 B cell line, that endocytoses FVIII through FVIII-specific B cell receptor, was unaltered upon incubation of the wtLCh in the presence of mannan, or upon Endo-F1-treatment (FIG. 4B). These data are reminiscent of our observations with intact FVIII (FIG. 3), and demonstrate that the entry of the FVIII light chain into monocyte-derived DCs mostly depends on mannosylated glycans.

FIG. 4C et 4D: The proper folding of the Asn2118Ala LCh was confirmed in an ELISA using a monoclonal human IgG specific for a conformational epitope in the C2 domain of FVIII (i.e., IgG produced by the BO2C11 B cell clone). The wtLCh activated D9E9 upon presentation by both BO2C11 and DCs (FIG. 4C). In contrast, while D9E9 was activated by the Asn2118Ala-LCh-FVIII upon presentation by BO2C11, it was not when DCs were used as Antigen Presenting Cells (APCs) (FIG. 4D).

Example 7

Cloning and Production of Recombinant FVIII Variants

Step 1. Cloning of the Different FVIII Variants
  cDNA encoding the BDD-FVIII (from ATCC, clone pSP64-FVIII), recombinant full length FVIII (Kogenate, Bayer) or any modified FVIII are used as "FVIII" in this example.
  The FVIII is subcloned in a subcloning vector (vector pCR®-Blunt II-TOPO®) using the Zero Blunt® TOPO® PCR. Site-directed mutagenesis is performed using the appropriate primers so as to generate 4 different FVIII variant cDNA:
  wild-type sequence
    single heavy-chain variant: codon AAC (Asn239) →codon GCC (Ala239)
    single light-chain variant: codon AAT (Asn2118) →codon GCT (Ala2118)
    double variant: Asn239Asn2118→Ala239Ala2118
  The insert is digested with the appropriate restriction enzymes, purified and cohesive end-ligated with either the pcDNA3.1(+) vector (Invitrogen, Carlsbad, Calif., USA) for expression of the protein in eukaryotic cell lines, or with the pLIVE vector (Minis, Madison, Wis., USA), for hydrodynamic injection in vivo.

Step 2. Transient Transfection of Mammalian Cell Lines
  The different pcDNA3.1(+)-FVIII variants is transfected into different eukaryotic cell lines: Chinese Hamster Ovary (CHO) cells, Baby Hamster Kidney (BHK) cells and HKB11 (Hybrid of Kidney and B cells; ATCC # CRL-12568) cells, using the Nucleofector® technology (Amaxa Biosystems). Typically, the Nucleofector® technology allows stable transfection of 70 to 100% of the cells. HKB11 cells have developed specifically for the production of recombinant FVIII.
  FVIII is detected in the supernatant using sandwich ELISA, surface plasmon resonance (SPR, Biacore®) and Western blotting. FVIII levels are compared to a commercially available recombinant FVIII standard (rFVIII, Kogenate®, Bayer, or BDD BrFVIII Refacto® Wyeth). Transient transfection indicates whether the FVIII variants are produced at all by the cells.

Step 3. In Vivo Transfection of the Different FVIII Constructs
  The different FVIII constructs cloned into the pLIVE vector is injected into FVIII-deficient mice. One hundred µg of each plasmid is injected intravenously in 2 ml in ≤5 seconds. This approach, referred to as "hydrodynamic injection", has been used successfully used in the past to express high levels of von Willebrand factor (VWF) in VWF-deficient mice (25). In these experiments, VWF expression was maintained for up to 3 weeks at levels superior to that found in the plasma of wild-type mice. Here, kinetics of FVIII expression is followed for 3 weeks using ELISA, SPR and Western blotting.

Step 4. Stable Transfection of Mammalian Cell Lines and Small-Scale Production
  Stable transfection will be performed as described in Step 2. Following transfection of the candidate cell line using the Nucleofector® technology, cells will be cloned by limiting dilutions. FVIII-producing cells will be amplified, and stocks will be kept frozen at −80° C.

Small-scale production of the proteins is performed in DMEM 1:1-F12 following classical methods. In brief, cells are gown to subconfluency for 3 to 4 days before collection of the supernatants. Supernatants will be tested for the presence of FVIII variants by ELISA, Surface plasmon resonance (Biacore®) and Western blotting, using murine and human monoclonal anti-FVIII IgG. The amounts of FVIII is quantified using commercially available rFVIII as a standard (Kogenate, Bayer, or Refacto Wyeth), so as to estimate the yields of production of FVIII per cell per day.

Step 5. Proposed Solution to Increase the Yield of Secretion/Production of the rFVIII Variants The level of production of rFVIII by mammalian cells is limited by different factors: 1) interactions of the A1 domain of FVIII with endosplasmic reticulum (ER) chaperones such as the immunoglobulin-binding protein (BiP), which inhibits the secretion of FVIII; 2) the binding of mannosylated sugars on the FVIII molecule to LMAN1 (ERGIC53) is required for a proper export from the ER to the Golgi apparatus, and thus removal of all N-linked glycosylation should be avoided, not to prevent binding to LMAN1 and export of FVIII. Conversely, the yields of FVIII production/secretion may be increased upon bioengineering of the molecule: 1) addition of a truncated part of the B domain, expressing 6 sites for N-glycosylation, increases the production of rFVIII by several folds as compared to wild-type domain deleted rFVIII; 2) mutation of Phe309 into a Ser residue reduces binding to BiP, and increases FVIII secretion. In this respect, elimination of sites for N-linked glycosylation by site directed mutagenesis might result in a reduced production of FVIII. Indeed, the wild-type B domain-deleted FVIII cDNA possesses 3 sites for glycosylation. Following site-directed mutagenesis, only one site is expected to remain: Asn1810 on the A3 domain, which might not be enough for proper secretion of the molecules.

If low yields of FVIII are obtained with mutated rFVIII variants, we might introduce in the construct the cDNA sequence encoding the first 226 amino acids of the B domain of FVIII. This sequence possesses 6 sites for N-linked glycosylation. To this end, mRNA has already been extracted from human liver extracts, and human cDNA has been prepared (a kind gift from Dr Cavard, Institut Cochin, Paris). B domain-encoding DNA is amplified using appropriate primers, and is inserted between the heavy and light chains of the four FVIII constructs. The B-domain containing constructs is then cloned in the pcDNA3 and pLIVE vectors. Cells are transfected and expression are studied as explained above.

Example 8

Medium-Scale Production of the Modified FVIII

FVIII from example 7 (wild type/$239^{mut}$/$2118^{mut}$/$239^{mut}2118^{mut}$ is produced using roller bottles in serum-supplemented basal medium. Sufficient amount of the different FVIII is produced in roller bottles and then purified using affinity chromatography. The estimated quantities necessary to do all the studies described below, has been evaluated to approximately 2 mg (10 000 UI) for each FVIII variant. The yield of the purification process is near 25% so, it will be necessary to produce 8 mg (40 000 UI) of each FVIII variant. The production of FVIII by each clone is adapted depending of the productivity of the clone. For high producer (>5 UI/$10^6$ cells/day), the production is done in roller bottles in batch system. For low producer (<5 UI/$10^6$ cells/day), the production is conducted in repeated batches using roller bottles.

Example 9

Structural/Functional Integrity of the Modified FVIII

Step 1. In Vivo Transfection of the Recombinant FVIII Variants

The different FVIII constructs from example 7 or 8 are cloned into the pLIVE vector and expressed in FVIII-deficient mice following hydrodynamic injection. Levels of FVIII in mouse plasma are measured using sandwich ELISA and functional coagulation assays. Correction of coagulation in mice is investigated following tail snipping and measurement of the time of bleeding and of the quantity of blood loss.

Step 2. Pro-Coagulant Activity In Vitro

The pro-coagulant activity of the four recombinant FVIII variants (example 7) is investigated in vitro and in vivo. FVIII in dilutions is incubated with human FVIII-depleted plasma and its activity is measured using a functional coagulation assay (FibrinTimer CA540, Dade-Behring). Alternatively, FVIII activity is assessed using a chromogenic assay, wherein FVIII is mixed with activated factor IX, and with factor X and phospholipids. Generation of activated factor X is then measured using a chromogenic synthetic substrate of activated factor X. Specific activities of the different FVIII constructs is calculated. B domain-deleted FVIII (Refacto®, Wyeth) is preferred and is used in the assay. Results from FXa generation are expressed as the ratio of the value from the standard divided by the test sample $t_{1/2}$ (half maximal response) value.

Step 3. Interaction of FVIII with Monoclonal Antibodies, von Willebrand Factor and Phospholipids The interaction of the different FVIII variants with monoclonal antibodies, von Willebrand factor and phospholipids is investigated.

Step 4. Methods for Post-Translational Modifications Analysis

Desalting, Concentration and Activation of FVIII

Concentration and desalting of FVIII samples are necessary to eliminate the salts, monosaccharides and small molecules that might interfere in a number of further analyses.

Desalting is carried out on a AKTA Purifier system (Amersham-Biosciences) equipped with a reverse phase (RP) Uptisphere 10WC4-25QS column (Interchim) equilibrated in 5% MeCN+TFA 0.1%. Elution is performed using a 5-90% gradient of MeCN+TFA 0.1% within 5 CV. The desalted product is collected and dried out in a Speed-Vac vacuum evaporator.

Purified FVIII samples can also undergo activation via thrombin treatment. The resulting FVIII chains might then be separated using RP-HPLC (Uptisphere UP5WOD$25QK) using a regular MeCN+TFA gradient.

b) Enzymatic Deglycosylation of FVIII i) PNGase F Deglycosylation

PNGase F is an enzyme specific for N-glycan structures. After desalting and drying, FVIII is resuspended in the enzyme buffer, either with or without reducing agents, and incubated for 15 min at room temperature. The enzyme is then added (E/S 5 mIU/200 µg) and deglycosylation is performed by incubation at 37° C. for 18 hours.

ii) Endo-H Deglycosylation

Endo H is an enzyme specific for N-glycan structures of the oligomannose and hybrid type. After desalting and drying, the FVIII is resuspended in the enzyme buffer, either with or without reducing agents, and heated for 5 min at 95° C. After cooling on ice, the enzyme is added (E/S: 0.2 mIU/µg prot). The deglycosylation reaction is performed for 2 hours at 37° C.

iii) SDS-PAGE Analysis

The glycosylation of FVIII can be partially characterized by SDS-PAGE analysis of products obtained before and after enzymatic deglycosylation with PNGAse F or Endo H. SDS-PAGE is performed on a NOVEX system (Invitrogen, Life Technologies). The sample is loaded (0.5 and 1 µg) under non-reducing and reducing conditions on a 4-12% gel (Novex). After migration at 200 V for 50 minutes, the proteins are silver stained. Following digital scanning and integration of the gel (Quantity One software, Biorad), the apparent molecular weight of the different protein bands are determined by comparison with protein standards.

iv) Lectin Blot Analysis

Specific detection of glycosylated (complex type, high manoses type . . . ) peptides and polypeptides, including FVIII, is performed using lectin-blot analysis (Fukuda et Kobata, Glycobiology a Practical Approach). Ten µg of FVIII are separated by SDS-PAGE as previously described and transferred to a nitrocellulose or nylon membrane according to the manufacturer instructions (Novex). Briefly, once blotted the membrane is blocked with BSA, washed in PBST (PBS, Tween 20 0.05%) and incubated 2 hours at 4° C. with the appropriate lectin (i.e. GNA, Con A, DGA, LcH, MNA-M, VFA, PEA, PMA, AMA . . . ) labeled with peroxydase (Ey labs). After some PBST washes, peroxydase is revealed by colorimetric or chemiluminescent methods and the resulting blot image is captured using a scanner or CCD camera. Image analysis and quantification are performed using Quantity One software (Biorad).

Step 5. Methods for FVIII Primary Structure Analysis a) FVIII Mapping

FVIII mapping enables primary structure analysis. The protein sequence is unique, and so the peptides generated after digestion with specific enzymes (trypsin or endoprotease Asp-N) are characteristic to the protein of interest. After desalting and drying, the FVIII is denatured (8M Urea), reduced (DTT 20 moles/mole of SH) and alkylated (iodoacetamide 40 moles/mole of SH). The FVIII is next digested with trypsin (E/S: 1/25 m/m), which cleaves the protein after Arg (R) and Lys (K) residues. Asp-N (E/S: 1/100 m/m), which cleaves the proteins before Asp (D) residues is also used. After protein digestion, the peptides generated are either directly injected onto a LC-MS/MS system for analysis, or separated by reverse phase HPLC chromatography, on a C18 300 Å column using an increasing acetonitrile gradient. Fractions are then eventually collected and dried using a Speed-Vac for additional analyses by Edman Sequencing and MALDI-TOF MS.

b) Edman Sequencing

N-terminal Edman sequencing of FVIII is performed on a microsequencer (Procise 491 HT, Applied Biosystems) in a three step procedure: coupling—cleavage and conversion. Amino acids are then separated by reverse phase chromatography. Analysis and identification of the N-terminal residues is achieved using standard amino acids from Sequence Pro (Applied Biosystems) and compared to the theoretical sequence of the FVIII, thus allowing confirmation of amino acid substitutions for instance.

c) Mass Spectrometry

MALDI TOF(/TOF)

Matrix-Assisted Laser Desorption/Ionisation Time of Flight Mass Spectrometry (MALDI-TOF MS) is a technique that enables the measurement of molecular masses with great accuracy. MALDI-TOF MS is an ionisation method enabling the analysis of peptides, proteins and glycans.

The peptides, proteins or glycans of interest (FVIII, fragments thereof or glycans) are mixed with a matrix which absorbs at the wavelength of the laser. The matrices used most often are a-cyano-4-hydroxycinnamic acid (HCCA for the analysis of peptides, sinapinic acid (SA) for proteins, and 2,5-dihydroxybenzoic acid for the (DHB) oligosaccharides. The identification of each peptide can be performed by measuring its mass by mass spectrometry, and comparing it with the theoretical mass deduced from the theoretical protein sequence. Peptide sequencing can be performed by using MS/MS experiments (tandem mass spectrometry, TOF/TOF), on the basis of fragment ions obtained under these conditions for a given peptide. A similar strategy is used for the identification/characterisation of oligosaccharides. A Bruker Autoflex 2 instrument is available.

Liquid Chromatography Coupled to Electrospray Ionisation Mass Spectrometry (LC-ESIMS)

In contrast to MALDI, electrospray ionisation (ESI) does not require the use of a matrix. In ESI, the sample solution is introduced into a capillary which is held under a high voltage. A strong electrical field is applied at the tubes exit leading to the formation of a spray of charged droplets that simultaneously cross an electric field and a pressure gradient which is in the path of the mass spectrometry analyser. The analysis by ESIMS can be carried out after chromatographic separation of the peptides under investigation, and a peptide map can also be obtained. In the case of FVIII, the separation of peptides can be performed on an Uptisphere UP5WOD25QK column (Interchim) with an acetonitrile gradient.

Detection by mass spectrometry is performed via a Qq-TOF hybrid mass spectrometer (quadripole—time of flight, Qstar-x1, Applied Biosystems) which enables the collection of MS and MS/MS data. Thus, the coverage of amino acid sequence can be achieved.

d) HPCE-LIF Oligosaccharide Mapping

The characterisation and quantification of different oligosaccharide structures linked to asparagines or "N-linked structures" is performed by HPCE-LIF. The sugars are released from FVIII by PNGase F treatment, and isolated by protein precipitation with ice-cold ethanol. The samples are treated with exoglycosidases (sialidase, galactosidase, mannosidases, hexnacase) in order to ensure that each isolated structure are quantified and characterised. All the glycosidases used are obtained from Prozyme. At this stage a second ethanolic precipitation is performed. The glycans obtained are labelled with a fluorophore (APTS) and separated based on both their mass and charge. Two standards (glucose homopolymers, oligosaccharides) allow identification of the structures.nony A Beckman Coulter N—CHO coated capillary (dimension 50 cm×50 μm ID) is mounted into a capillary electrophoresis (ProteomeLab PA800, Beckman Coulter). Experimental conditions are: separation buffer <<gel buffer-N— Beckman coulter>>, migration at 25 KV, 20 min at 20° C., and Laser detection using λex 488 nm and λem 520 nm.

e) NP-HPLC Oligosaccharide Mapping

Identification and quantification of the various oligosaccharide structures linked to asparagines, known as N-linked structures, can also be carried out by normal phase high performance liquid chromatography (NP-HPLC). The N-glycans are released using a specific enzyme (PNGase F), and isolated by ethanol precipitation. The glycans obtained are labelled with 2-aminobenzamide (2-AB) fluorophore. The labelled glycans are separated by NP-HPLC using a Amide-80 column (Tosohaas), connected to a <<Gold>> system, (Beckman).

Prior to sample injection, the column is equilibrated with 80% acetonitrile buffer. The oligosaccharides are eluted in an increasing gradient of 50 mM ammonium formate pH 4.45. Detection is performed using fluorescence at λex 330 nm and λem 420 nm Example 10

Immunogenicity of Asn2118Ala LCh in a FVIII Deficient Mice Protocol

Purified plasma-derivated light chain of human FVIII (wtLCh) was kindly provided by Dr E Saenko (University of Maryland, Baltimore, Md., USA). A mutated LCh of FVIII (Asn2118Ala LCh) was generated and produced. wtLCh and mutated LCh were injected intravenously (0.2 μg protein in 200 μL PBS) to FVIII-deficient mice (a kind gift from Prof Kazazian, Pennsylvania University, USA) four times at weekly intervals. One week after the fourth injection, mice were bled and levels of anti-FVIII IgG were investigated using a FVIII-specific ELISA.

ELISA: Mice sera were diluted 1 into 90 and were incubated in ELISA plate coated with human FVIII. (Recombinate, Baxter). Plates were blocked using PBS-1% BSA. Bound IgG were revealed using a polyclonal anti-murine IgG coupled to peroxidase, and the peroxidase substrate (OPD). Intensity of binding was measured by optical density at 492 nm with a spectrometer (Tecan Genyos), thus defining levels of anti-FVIII IgG.

Results

Intravenous administration of the purified plasma-derivated light chain of human FVIII (wtLCh) to FVIII deficient mice induced detectable levels of anti-FVIII IgG. It is interesting to note that the immune response of the mice to the wtLCh was heterogeneous among the six mice included in the experiment. By contrast, treatment of mice with the mutated Asn2118Ala LCh failed to induce major levels of anti-FVIII IgG.

Conclusion

These data shows that the ability of the Asn2118Ala LCh to induce a specific immune response is strongly reduced compared to the wtLCh.

BIBLIOGRAPHY

1. Lenting P, et al. 1998. Blood 92(11):3983-96
2. Lusher J M et al. 2003 Hoemophilia 9: 33-49
3. Ehrenforth S, et al. 1992. Lancet 339:594.
4. De Biasi R, et al. 1994. Throm Haemost 7(5):544
5. Gringeri A, et al. 2003. Blood 102:2358
6. Banchereau J, et al. 1998. Nature 392:245
7. Trombetta E S, et al. 2005. Annu Rev Immunol 23:975
8. Geijtenbeek T B, et al. 2004. Annu Rev Immunol 22:33
9. Sallusto F, et al. 1995. J Exp Med 182:389
10. Geijtenbeek T B, et al. 2000. Cell 100:575
11. Keler T, et al. 2004. Expert Opin Biol Ther 4:1953
12. Saint-Remy J M et al. 1999 Vox Sang; 77 (suppl 1): 21-24
13. Jacquemin et al. 2000 Blood 95: 156-163
14. Jacquemin et al. 1998 Blood July 15; 92 (2): 496-506
15. Subramani et al. 1981 Mol. Cell. Biol. 1:854-864
16. Boshart et al. 1985 Cell 41:521-530
17. Kaufman and Sharp, 1982 Mol. Cell. Biol. 2:1304-1319
18. Bergman et al. 1983 Proc. Natl. Acad. Sci. USA 81:7041-7045
19. Loh et al. 1983 Cell 33:85-93
20. Palmiter et al. 1983 Science 222:809-814
21. DeNoto et al. 1981 Nuc. Acids Res. 9:3719-3730
22. Pittman et al. 1994. Blood 84(12):4214-4225
23. Kaufman R J 1989. Nature 342(6246): 207-208
24. Toole et al. 1984. Nature 312(5992): 342-347
25. Lenting et al. 2007. Blood. 109(5):2267-2268

The invention claimed is:

1. A FVIII protein with a procoagulant activity comprising a modified FVIII peptide, wherein the modification of said modified FVIII polypeptide comprises
   the substitution or the deletion of at least one amino acid selected from the group consisting of asparagine 239, and asparagine 2118 with reference to the full length human FVIII polypeptide sequence set forth in SEQ ID NO. 2, and
   at least the first 226 amino acids of the B domain of said full length human FVIII polypeptide sequence.

2. A FVIII protein according to claim 1, wherein said modification at least comprises the substitution of asparagine 239 with an amino acid selected from the group consisting of alanine, serine, glutamine, threonine, aspartic acid and glutamic acid.

3. A FVIII protein according to claim 1, wherein said modification at least comprises the substitution of asparagine 2118 with an amino acid selected from the group consisting of alanine, serine, glutamine, threonine, aspartic acid and glutamic acid.

4. A FVIII protein according to claim 2, wherein said modification at least comprises the substitution of asparagine 239 with alanine.

5. A FVIII protein according to claim 2, wherein said modification at least comprises the substitution of asparagine 239 with glutamine.

6. A FVIII protein according to claim 3, wherein said modification at least comprises the substitution of asparagine 2118 with alanine.

7. A FVIII protein according to claim 3, wherein said modification at least comprises the substitution of asparagine 2118 with glutamine.

8. A FVIII protein according to claim 1, wherein said modification comprises substitution of both asparagine 239 and asparagine 2118 with alanine.

9. A FVIII protein according to claim 1, wherein said modification comprises substitution of both asparagine 239 and asparagine 2118 with glutamine.

10. A FVIII protein according to claim 1, wherein said modification comprises substitution of both asparagine 239 with alanine and asparagine 2118 with Glutamine.

11. A FVIII protein according to claim 1, wherein said modification comprises both the substitution of asparagine 239 with glutamine and asparagine 2118 with alanine.

12. A FVIII protein according to claim 1, wherein the modification of said modified FVIII polypeptide further comprises the deletion of whole or part of the B domain set forth in SEQ ID No: 10, except for said at least the first 226 amino acids.

13. A FVIII protein according to claim 1, wherein the modified FVIII polypeptide comprises at least one of:
   (i) the amino acid sequence set forth in SEQ ID No:6; and
   (ii) the amino acid sequence set forth in SEQ ID No: 8.

14. A composition comprising a FVIII protein according to claim 1.

15. A composition according to claim 14, wherein said composition is a pharmaceutical composition or a lyophilized composition.

16. A composition according to claim 14, further comprising a pharmaceutically acceptable carrier.

\* \* \* \* \*

SEQUENCE LISTING

```
<160> NUMBER OF SEQ ID NOS: 14

<210> SEQ ID NO 1
<211> LENGTH: 2351
<212> TYPE: PRT
<213> ORGANISM: Homo sapiens

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60
```

```
Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
```

```
                485                 490                 495
His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
                530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
                690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
                755                 760                 765

Ser Thr Arg Gln Lys Gln Phe Asn Ala Thr Thr Ile Pro Glu Asn Asp
                770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
                835                 840                 845

Ser Leu Ser Glu Met Thr His Phe Arg Pro Gln Leu His His Ser Gly
                850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910
```

```
Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305
```

```
Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350

Asp Thr Ser Thr Gln Trp Ser Lys Asn Met Lys His Leu Thr Pro
    1355                1360                1365

Ser Thr Leu Thr Gln Ile Asp Tyr Asn Glu Lys Glu Lys Gly Ala
    1370                1375                1380

Ile Thr Gln Ser Pro Leu Ser Asp Cys Leu Thr Arg Ser His Ser
    1385                1390                1395

Ile Pro Gln Ala Asn Arg Ser Pro Leu Pro Ile Ala Lys Val Ser
    1400                1405                1410

Ser Phe Pro Ser Ile Arg Pro Ile Tyr Leu Thr Arg Val Leu Phe
    1415                1420                1425

Gln Asp Asn Ser Ser His Leu Pro Ala Ala Ser Tyr Arg Lys Lys
    1430                1435                1440

Asp Ser Gly Val Gln Glu Ser Ser His Phe Leu Gln Gly Ala Lys
    1445                1450                1455

Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
```

-continued

```
                1700                1705                1710
Thr Arg His Tyr Phe Ile Ala Ala Val Glu Arg Leu Trp Asp Tyr
    1715                1720                1725
Gly Met Ser Ser Ser Pro His Val Leu Arg Asn Arg Ala Gln Ser
    1730                1735                1740
Gly Ser Val Pro Gln Phe Lys Lys Val Val Phe Gln Glu Phe Thr
    1745                1750                1755
Asp Gly Ser Phe Thr Gln Pro Leu Tyr Arg Gly Glu Leu Asn Glu
    1760                1765                1770
His Leu Gly Leu Leu Gly Pro Tyr Ile Arg Ala Glu Val Glu Asp
    1775                1780                1785
Asn Ile Met Val Thr Phe Arg Asn Gln Ala Ser Arg Pro Tyr Ser
    1790                1795                1800
Phe Tyr Ser Ser Leu Ile Ser Tyr Glu Glu Asp Gln Arg Gln Gly
    1805                1810                1815
Ala Glu Pro Arg Lys Asn Phe Val Lys Pro Asn Glu Thr Lys Thr
    1820                1825                1830
Tyr Phe Trp Lys Val Gln His His Met Ala Pro Thr Lys Asp Glu
    1835                1840                1845
Phe Asp Cys Lys Ala Trp Ala Tyr Phe Ser Asp Val Asp Leu Glu
    1850                1855                1860
Lys Asp Val His Ser Gly Leu Ile Gly Pro Leu Leu Val Cys His
    1865                1870                1875
Thr Asn Thr Leu Asn Pro Ala His Gly Arg Gln Val Thr Val Gln
    1880                1885                1890
Glu Phe Ala Leu Phe Phe Thr Ile Phe Asp Glu Thr Lys Ser Trp
    1895                1900                1905
Tyr Phe Thr Glu Asn Met Glu Arg Asn Cys Arg Ala Pro Cys Asn
    1910                1915                1920
Ile Gln Met Glu Asp Pro Thr Phe Lys Glu Asn Tyr Arg Phe His
    1925                1930                1935
Ala Ile Asn Gly Tyr Ile Met Asp Thr Leu Pro Gly Leu Val Met
    1940                1945                1950
Ala Gln Asp Gln Arg Ile Arg Trp Tyr Leu Leu Ser Met Gly Ser
    1955                1960                1965
Asn Glu Asn Ile His Ser Ile His Phe Ser Gly His Val Phe Thr
    1970                1975                1980
Val Arg Lys Lys Glu Glu Tyr Lys Met Ala Leu Tyr Asn Leu Tyr
    1985                1990                1995
Pro Gly Val Phe Glu Thr Val Glu Met Leu Pro Ser Lys Ala Gly
    2000                2005                2010
Ile Trp Arg Val Glu Cys Leu Ile Gly Glu His Leu His Ala Gly
    2015                2020                2025
Met Ser Thr Leu Phe Leu Val Tyr Ser Asn Lys Cys Gln Thr Pro
    2030                2035                2040
Leu Gly Met Ala Ser Gly His Ile Arg Asp Phe Gln Ile Thr Ala
    2045                2050                2055
Ser Gly Gln Tyr Gly Gln Trp Ala Pro Lys Leu Ala Arg Leu His
    2060                2065                2070
Tyr Ser Gly Ser Ile Asn Ala Trp Ser Thr Lys Glu Pro Phe Ser
    2075                2080                2085
Trp Ile Lys Val Asp Leu Leu Ala Pro Met Ile Ile His Gly Ile
    2090                2095                2100
```

-continued

```
Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 2
<211> LENGTH: 2332
<212> TYPE: PRT
<213> ORGANISM: Homo sapiens

<400> SEQUENCE: 2

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
    65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
```

-continued

```
                100             105             110
Glu Tyr Asp Asp Gln Thr Ser Gln Arg Glu Lys Glu Asp Asp Lys Val
            115                 120                 125
Phe Pro Gly Gly Ser His Thr Tyr Val Trp Gln Val Leu Lys Glu Asn
130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Arg Glu Gly Ser Leu Ala Lys Glu Lys Thr Gln Thr Leu
            180                 185                 190
His Lys Phe Ile Leu Leu Phe Ala Val Phe Asp Glu Gly Lys Ser Trp
        195                 200                 205
His Ser Glu Thr Lys Asn Ser Leu Met Gln Asp Arg Asp Ala Ala Ser
    210                 215                 220
Ala Arg Ala Trp Pro Lys Met His Thr Val Asn Gly Tyr Val Asn Arg
225                 230                 235                 240
Ser Leu Pro Gly Leu Ile Gly Cys His Arg Lys Ser Val Tyr Trp His
                245                 250                 255
Val Ile Gly Met Gly Thr Thr Pro Glu Val His Ser Ile Phe Leu Glu
            260                 265                 270
Gly His Thr Phe Leu Val Arg Asn His Arg Gln Ala Ser Leu Glu Ile
        275                 280                 285
Ser Pro Ile Thr Phe Leu Thr Ala Gln Thr Leu Leu Met Asp Leu Gly
    290                 295                 300
Gln Phe Leu Leu Phe Cys His Ile Ser Ser His Gln His Asp Gly Met
305                 310                 315                 320
Glu Ala Tyr Val Lys Val Asp Ser Cys Pro Glu Glu Pro Gln Leu Arg
                325                 330                 335
Met Lys Asn Asn Glu Glu Ala Glu Asp Tyr Asp Asp Asp Leu Thr Asp
            340                 345                 350
Ser Glu Met Asp Val Val Arg Phe Asp Asp Asp Asn Ser Pro Ser Phe
        355                 360                 365
Ile Gln Ile Arg Ser Val Ala Lys Lys His Pro Lys Thr Trp Val His
    370                 375                 380
Tyr Ile Ala Ala Glu Glu Glu Asp Trp Asp Tyr Ala Pro Leu Val Leu
385                 390                 395                 400
Ala Pro Asp Asp Arg Ser Tyr Lys Ser Gln Tyr Leu Asn Asn Gly Pro
                405                 410                 415
Gln Arg Ile Gly Arg Lys Tyr Lys Lys Val Arg Phe Met Ala Tyr Thr
            420                 425                 430
Asp Glu Thr Phe Lys Thr Arg Glu Ala Ile Gln His Glu Ser Gly Ile
        435                 440                 445
Leu Gly Pro Leu Leu Tyr Gly Glu Val Gly Asp Thr Leu Leu Ile Ile
    450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
            500                 505                 510
Trp Thr Val Thr Val Glu Asp Gly Pro Thr Lys Ser Asp Pro Arg Cys
        515                 520                 525
```

```
Leu Thr Arg Tyr Tyr Ser Ser Phe Val Asn Met Glu Arg Asp Leu Ala
        530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
            580                 585                 590
Arg Phe Leu Pro Asn Pro Ala Gly Val Gln Leu Glu Asp Pro Glu Phe
        595                 600                 605
Gln Ala Ser Asn Ile Met His Ser Ile Asn Gly Tyr Val Phe Asp Ser
610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
            660                 665                 670
Phe Ser Gly Glu Thr Val Phe Met Ser Met Glu Asn Pro Gly Leu Trp
        675                 680                 685
Ile Leu Gly Cys His Asn Ser Asp Phe Arg Asn Arg Gly Met Thr Ala
690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
            740                 745                 750
Gln Lys Gln Phe Asn Ala Thr Thr Ile Pro Glu Asn Asp Ile Glu Lys
        755                 760                 765
Thr Asp Pro Trp Phe Ala His Arg Thr Pro Met Pro Lys Ile Gln Asn
770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
            820                 825                 830
Glu Met Thr His Phe Arg Pro Gln Leu His His Ser Gly Asp Met Val
        835                 840                 845
Phe Thr Pro Glu Ser Gly Leu Gln Leu Arg Leu Asn Glu Lys Leu Gly
850                 855                 860
Thr Thr Ala Ala Thr Glu Leu Lys Lys Leu Asp Phe Lys Val Ser Ser
865                 870                 875                 880
Thr Ser Asn Asn Leu Ile Ser Thr Ile Pro Ser Asp Asn Leu Ala Ala
                885                 890                 895
Gly Thr Asp Asn Thr Ser Ser Leu Gly Pro Pro Ser Met Pro Val His
            900                 905                 910
Tyr Asp Ser Gln Leu Asp Thr Thr Leu Phe Gly Lys Lys Ser Ser Pro
        915                 920                 925
Leu Thr Glu Ser Gly Gly Pro Leu Ser Leu Ser Glu Glu Asn Asn Asp
930                 935                 940
```

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
            965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
    1010                1015                1020

Asn Ser Pro Ser Val Trp Gln Asn Ile Leu Glu Ser Asp Thr Glu
    1025                1030                1035

Phe Lys Lys Val Thr Pro Leu Ile His Asp Arg Met Leu Met Asp
    1040                1045                1050

Lys Asn Ala Thr Ala Leu Arg Leu Asn His Met Ser Asn Lys Thr
    1055                1060                1065

Thr Ser Ser Lys Asn Met Glu Met Val Gln Gln Lys Lys Glu Gly
    1070                1075                1080

Pro Ile Pro Pro Asp Ala Gln Asn Pro Asp Met Ser Phe Phe Lys
    1085                1090                1095

Met Leu Phe Leu Pro Glu Ser Ala Arg Trp Ile Gln Arg Thr His
    1100                1105                1110

Gly Lys Asn Ser Leu Asn Ser Gly Gln Gly Pro Ser Pro Lys Gln
    1115                1120                1125

Leu Val Ser Leu Gly Pro Glu Lys Ser Val Glu Gly Gln Asn Phe
    1130                1135                1140

Leu Ser Glu Lys Asn Lys Val Val Val Gly Lys Gly Glu Phe Thr
    1145                1150                1155

Lys Asp Val Gly Leu Lys Glu Met Val Phe Pro Ser Ser Arg Asn
    1160                1165                1170

Leu Phe Leu Thr Asn Leu Asp Asn Leu His Glu Asn Asn Thr His
    1175                1180                1185

Asn Gln Glu Lys Lys Ile Gln Glu Glu Ile Glu Lys Lys Glu Thr
    1190                1195                1200

Leu Ile Gln Glu Asn Val Val Leu Pro Gln Ile His Thr Val Thr
    1205                1210                1215

Gly Thr Lys Asn Phe Met Lys Asn Leu Phe Leu Leu Ser Thr Arg
    1220                1225                1230

Gln Asn Val Glu Gly Ser Tyr Asp Gly Ala Tyr Ala Pro Val Leu
    1235                1240                1245

Gln Asp Phe Arg Ser Leu Asn Asp Ser Thr Asn Arg Thr Lys Lys
    1250                1255                1260

His Thr Ala His Phe Ser Lys Lys Gly Glu Glu Glu Asn Leu Glu
    1265                1270                1275

Gly Leu Gly Asn Gln Thr Lys Gln Ile Val Glu Lys Tyr Ala Cys
    1280                1285                1290

Thr Thr Arg Ile Ser Pro Asn Thr Ser Gln Gln Asn Phe Val Thr
    1295                1300                1305

Gln Arg Ser Lys Arg Ala Leu Lys Gln Phe Arg Leu Pro Leu Glu
    1310                1315                1320

Glu Thr Glu Leu Glu Lys Arg Ile Ile Val Asp Asp Thr Ser Thr
    1325                1330                1335

Gln Trp Ser Lys Asn Met Lys His Leu Thr Pro Ser Thr Leu Thr

-continued

```
            1340                1345                1350
Gln Ile Asp Tyr Asn Glu Lys Glu Lys Gly Ala Ile Thr Gln Ser
    1355                1360                1365
Pro Leu Ser Asp Cys Leu Thr Arg Ser His Ser Ile Pro Gln Ala
    1370                1375                1380
Asn Arg Ser Pro Leu Pro Ile Ala Lys Val Ser Ser Phe Pro Ser
    1385                1390                1395
Ile Arg Pro Ile Tyr Leu Thr Arg Val Leu Phe Gln Asp Asn Ser
    1400                1405                1410
Ser His Leu Pro Ala Ala Ser Tyr Arg Lys Lys Asp Ser Gly Val
    1415                1420                1425
Gln Glu Ser Ser His Phe Leu Gln Gly Ala Lys Lys Asn Asn Leu
    1430                1435                1440
Ser Leu Ala Ile Leu Thr Leu Glu Met Thr Gly Asp Gln Arg Glu
    1445                1450                1455
Val Gly Ser Leu Gly Thr Ser Ala Thr Asn Ser Val Thr Tyr Lys
    1460                1465                1470
Lys Val Glu Asn Thr Val Leu Pro Lys Pro Asp Leu Pro Lys Thr
    1475                1480                1485
Ser Gly Lys Val Glu Leu Leu Pro Lys Val His Ile Tyr Gln Lys
    1490                1495                1500
Asp Leu Phe Pro Thr Glu Thr Ser Asn Gly Ser Pro Gly His Leu
    1505                1510                1515
Asp Leu Val Glu Gly Ser Leu Leu Gln Gly Thr Glu Gly Ala Ile
    1520                1525                1530
Lys Trp Asn Glu Ala Asn Arg Pro Gly Lys Val Pro Phe Leu Arg
    1535                1540                1545
Val Ala Thr Glu Ser Ser Ala Lys Thr Pro Ser Lys Leu Leu Asp
    1550                1555                1560
Pro Leu Ala Trp Asp Asn His Tyr Gly Thr Gln Ile Pro Lys Glu
    1565                1570                1575
Glu Trp Lys Ser Gln Glu Lys Ser Pro Glu Lys Thr Ala Phe Lys
    1580                1585                1590
Lys Lys Asp Thr Ile Leu Ser Leu Asn Ala Cys Glu Ser Asn His
    1595                1600                1605
Ala Ile Ala Ala Ile Asn Glu Gly Gln Asn Lys Pro Glu Ile Glu
    1610                1615                1620
Val Thr Trp Ala Lys Gln Gly Arg Thr Glu Arg Leu Cys Ser Gln
    1625                1630                1635
Asn Pro Pro Val Leu Lys Arg His Gln Arg Glu Ile Thr Arg Thr
    1640                1645                1650
Thr Leu Gln Ser Asp Gln Glu Glu Ile Asp Tyr Asp Asp Thr Ile
    1655                1660                1665
Ser Val Glu Met Lys Lys Glu Asp Phe Asp Ile Tyr Asp Glu Asp
    1670                1675                1680
Glu Asn Gln Ser Pro Arg Ser Phe Gln Lys Lys Thr Arg His Tyr
    1685                1690                1695
Phe Ile Ala Ala Val Glu Arg Leu Trp Asp Tyr Gly Met Ser Ser
    1700                1705                1710
Ser Pro His Val Leu Arg Asn Arg Ala Gln Ser Gly Ser Val Pro
    1715                1720                1725
Gln Phe Lys Lys Val Val Phe Gln Glu Phe Thr Asp Gly Ser Phe
    1730                1735                1740
```

```
Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
1805                1810                1815

Val Gln His His Met Ala Pro Thr Lys Asp Glu Phe Asp Cys Lys
1820                1825                1830

Ala Trp Ala Tyr Phe Ser Asp Val Asp Leu Glu Lys Asp Val His
1835                1840                1845

Ser Gly Leu Ile Gly Pro Leu Leu Val Cys His Thr Asn Thr Leu
1850                1855                1860

Asn Pro Ala His Gly Arg Gln Val Thr Val Gln Glu Phe Ala Leu
1865                1870                1875

Phe Phe Thr Ile Phe Asp Glu Thr Lys Ser Trp Tyr Phe Thr Glu
1880                1885                1890

Asn Met Glu Arg Asn Cys Arg Ala Pro Cys Asn Ile Gln Met Glu
1895                1900                1905

Asp Pro Thr Phe Lys Glu Asn Tyr Arg Phe His Ala Ile Asn Gly
1910                1915                1920

Tyr Ile Met Asp Thr Leu Pro Gly Leu Val Met Ala Gln Asp Gln
1925                1930                1935

Arg Ile Arg Trp Tyr Leu Leu Ser Met Gly Ser Asn Glu Asn Ile
1940                1945                1950

His Ser Ile His Phe Ser Gly His Val Phe Thr Val Arg Lys Lys
1955                1960                1965

Glu Glu Tyr Lys Met Ala Leu Tyr Asn Leu Tyr Pro Gly Val Phe
1970                1975                1980

Glu Thr Val Glu Met Leu Pro Ser Lys Ala Gly Ile Trp Arg Val
1985                1990                1995

Glu Cys Leu Ile Gly Glu His Leu His Ala Gly Met Ser Thr Leu
2000                2005                2010

Phe Leu Val Tyr Ser Asn Lys Cys Gln Thr Pro Leu Gly Met Ala
2015                2020                2025

Ser Gly His Ile Arg Asp Phe Gln Ile Thr Ala Ser Gly Gln Tyr
2030                2035                2040

Gly Gln Trp Ala Pro Lys Leu Ala Arg Leu His Tyr Ser Gly Ser
2045                2050                2055

Ile Asn Ala Trp Ser Thr Lys Glu Pro Phe Ser Trp Ile Lys Val
2060                2065                2070

Asp Leu Leu Ala Pro Met Ile Ile His Gly Ile Lys Thr Gln Gly
2075                2080                2085

Ala Arg Gln Lys Phe Ser Ser Leu Tyr Ile Ser Gln Phe Ile Ile
2090                2095                2100

Met Tyr Ser Leu Asp Gly Lys Lys Trp Gln Thr Tyr Arg Gly Asn
2105                2110                2115

Ser Thr Gly Thr Leu Met Val Phe Phe Gly Asn Val Asp Ser Ser
2120                2125                2130
```

| | | | | | | | | | | | |
|---|---|---|---|---|---|---|---|---|---|---|---|
|Gly|Ile|Lys|His|Asn|Ile|Phe|Asn|Pro|Pro|Ile|Ile|Ala|Arg|Tyr|
| |2135| | | |2140| | | |2145| | | | | |

Gly Ile Lys His Asn Ile Phe Asn Pro Pro Ile Ile Ala Arg Tyr
    2135                2140              2145

Ile Arg Leu His Pro Thr His Tyr Ser Ile Arg Ser Thr Leu Arg
    2150                2155              2160

Met Glu Leu Met Gly Cys Asp Leu Asn Ser Cys Ser Met Pro Leu
    2165                2170              2175

Gly Met Glu Ser Lys Ala Ile Ser Asp Ala Gln Ile Thr Ala Ser
    2180                2185              2190

Ser Tyr Phe Thr Asn Met Phe Ala Thr Trp Ser Pro Ser Lys Ala
    2195                2200              2205

Arg Leu His Leu Gln Gly Arg Ser Asn Ala Trp Arg Pro Gln Val
    2210                2215              2220

Asn Asn Pro Lys Glu Trp Leu Gln Val Asp Phe Gln Lys Thr Met
    2225                2230              2235

Lys Val Thr Gly Val Thr Thr Gln Gly Val Lys Ser Leu Leu Thr
    2240                2245              2250

Ser Met Tyr Val Lys Glu Phe Leu Ile Ser Ser Gln Asp Gly
    2255                2260              2265

His Gln Trp Thr Leu Phe Phe Gln Asn Gly Lys Val Lys Val Phe
    2270                2275              2280

Gln Gly Asn Gln Asp Ser Phe Thr Pro Val Val Asn Ser Leu Asp
    2285                2290              2295

Pro Pro Leu Leu Thr Arg Tyr Leu Arg Ile His Pro Gln Ser Trp
    2300                2305              2310

Val His Gln Ile Ala Leu Arg Met Glu Val Leu Gly Cys Glu Ala
    2315                2320              2325

Gln Asp Leu Tyr
    2330

<210> SEQ ID NO 3
<211> LENGTH: 4275
<212> TYPE: DNA
<213> ORGANISM: Homo sapiens

<400> SEQUENCE: 3

```
gccaccagaa gatactacct gggtgcagtg gaactgtcat gggactatat gcaaagtgat      60
ctcggtgagc tgcctgtgga cgcaagattt cctcctagag tgccaaaatc ttttccattc     120
aacacctcag tcgtgtacaa aaagactctg tttgtagaat tcacggttca ccttttcaac     180
atcgctaagc caaggccacc ctggatgggt ctgctaggtc ctaccatcca ggctgaggtt     240
tatgatacag tggtcattac acttaagaac atggcttccc atcctgtcag tcttcatgct     300
gttggtgtat cctactggaa agcttctgag ggagctgaat atgatgatca gaccagtcaa     360
agggagaaag aagatgataa agtcttccct ggtggaagcc atacatatgt ctggcaggtc     420
ctgaaagaga atggtccaat ggcctctgac ccactgtgcc ttacctactc atatctttct     480
catgtggacc tggtaaaaga cttgaattca ggcctcattg agccctact  agtatgtaga     540
gaagggagtc tggccaagga aaagacacag accttgcaca aatttatact acttttgct      600
gtatttgatg aagggaaaag ttggcactca gaaacaaaga actccttgat gcaggatagg     660
gatgctgcat ctgctcgggc ctggcctaaa atgcacacag tcaatggtta tgtaaacagg     720
tctctgccag gtctgattgg atgccacagg aaatcagtct attggcatgt gattggaatg     780
ggcaccactc ctgaagtgca ctcaatattc ctcgaaggtc acacatttct tgtgaggaac     840
catcgccagg cgtccttgga aatctcgcca ataactttcc ttactgctca acactcttg      900
```

```
atggaccttg dacagtttct actgttttgt catatctctt cccaccaaca tgatggcatg    960
gaagcttatg tcaaagtaga cagctgtcca gaggaacccc aactacgaat gaaaaataat   1020
gaagaagcgg aagactatga tgatgatctt actgattctg aaatggatgt ggtcaggttt   1080
gatgatgaca actctccttc ctttatccaa attcgctcag ttgccaagaa gcatcctaaa   1140
acttgggtac attacattgc tgctgaagag gaggactggg actatgctcc cttagtcctc   1200
gcccccgatg acagaagtta taaaagtcaa tatttgaaca atggccctca gcggattggt   1260
aggaagtaca aaaaagtccg atttatggca tacacagatg aaacctttaa gactcgtgaa   1320
gctattcagc atgaatcagg aatcttggga cctttacttt atggggaagt ggagacaca   1380
ctgttgatta tatttaagaa tcaagcaagc agaccatata acatctaccc tcacggaatc   1440
actgatgtcc gtcctttgta ttcaaggaga ttaccaaaag gtgtaaaaca tttgaaggat   1500
tttccaattc tgccaggaga aatattcaaa tataaatgga cagtgactgt agaagatggg   1560
ccaactaaat cagatcctcg gtgcctgacc cgctattact ctagtttcgt taatatggag   1620
agagatctag cttcaggact cattggccct ctcctcatct gctacaaaga atctgtagat   1680
caaagaggaa accagataat gtcagacaag aggaatgtca tcctgttttc tgtatttgat   1740
gagaaccgaa gctggtacct cacagagaat atacaacgct tctccccaa tccagctgga   1800
gtgcagcttg aggatccaga gttccaagcc tccaacatca tgcacagcat caatggctat   1860
gttttttgata gtttgcagtt gtcagtttgt ttgcatgagg tggcatactg gtacattcta   1920
agcattggag cacagactga cttcctttct gtcttcttct ctggatatac cttcaaacac   1980
aaaatggtct atgaagacac actcaccta ttcccattct caggagaaac tgtcttcatg   2040
tcgatggaaa acccaggtct atggattctg gggtgccaca actcagactt cggaacagaa   2100
ggcatgaccg ccttactgaa ggtttctagt tgtgacaaga cactggtga ttattacgag   2160
gacagttatg aagatatttc agcatacttg ctgagtaaaa acaatgccat gaaccaaga   2220
gaaataactc gtactactct tcagtcagat caagaggaaa ttgactatga tgataccata   2280
tcagttgaaa tgaagaagga agattttgac atttatgatg aggatgaaaa tcagagcccc   2340
cgcagctttc aaaagaaaac acgacactat tttattgctg cagtggagag gctctgggat   2400
tatgggatga gtagctcccc acatgttcta agaaacaggg ctcagagtgg cagtgtccct   2460
cagttcaaga agttgttttt ccaggaattt actgatggct cctttactca gcccttatac   2520
cgtggagaac taaatgaaca tttgggactc ctggggccat atataagagc agaagttgaa   2580
gataatatca tggtaacttt cagaaatcag gcctctcgtc cctattcctt ctattctagc   2640
cttatttctt atgaggaaga tcagaggcaa ggagcagaac tagaaaaaaa ctttgtcaag   2700
cctaatgaaa ccaaaactta cttttggaaa gtgcaacatc atatggcacc cactaaagat   2760
gagtttgact gcaaagcctg gcttatttc tctgatgttg acctggaaaa agatgtgcac   2820
tcaggcctga ttggacccct tctggtctgc acactaaca cactgaaccc tgctcatggg   2880
agacaagtga cagtacagga atttgctctg tttttcacca tctttgatga gaccaaaagc   2940
tggtacttca ctgaaaatat ggaaagaaac tgcagggctc cctgcaatat ccagatggaa   3000
gatcccactt ttaaagagaa ttatcgcttc catgcaatca atggctacat aatggataca   3060
ctacctggct tagtaatggc tcaggatcaa aggattcgat ggtatctgct cagcatgggc   3120
agcaatgaaa acatccattc tattcatttc agtggacatg tgttcactgt acgaaaaaaa   3180
gaggagtata aaatggcact gtacaatctc tatccaggtg ttttttgagac agtggaaatg   3240
```

-continued

```
ttaccatcca aagctggaat ttggcgggtg gaatgcctta ttggcgagca tctacatgct    3300
gggatgagca cacttttttct ggtgtacagc aataagtgtc agactcccct gggaatggct    3360
tctggacaca ttagagattt tcagattaca gcttcaggac aatatggaca gtgggcccca    3420
aagctggcca gacttcatta ttccggatca atcaatgcct ggagcaccaa ggagcccttt    3480
tcttggatca aggtggatct gttggcacca atgattattc acggcatcaa gacccagggt    3540
gcccgtcaga agttctccag cctctacatc tctcagttta tcatcatgta tagtcttgat    3600
gggaagaagt ggcagactta tcgaggaaat tccactggaa ccttaatggt cttctttggc    3660
aatgtggatt catctgggat aaaacacaat attttttaacc ctccaattat tgctcgatac    3720
atccgtttgc acccaactca ttatagcatt cgcagcactc ttcgcatgga gttgatgggc    3780
tgtgatttaa atagttgcag catgccattg ggaatggaga gtaaagcaat atcagatgca    3840
cagattactg cttcatccta ctttaccaat atgtttgcca cctggtctcc ttcaaaagct    3900
cgacttcacc tccaagggag gagtaatgcc tggagacctc aggtgaataa tccaaaagag    3960
tggctgcaag tggacttcca gaagacatg aaagtcacag gagtaactac tcagggagta    4020
aaatctctgc ttaccagcat gtatgtgaag gagttcctca tctccagcag tcaagatggc    4080
catcagtgga ctctcttttt tcagaatggc aaagtaaagg tttttcaggg aaatcaagac    4140
tccttcacac ctgtggtgaa ctctctagac ccaccgttac tgactcgcta ccttcgaatt    4200
cacccccaga gttgggtgca ccagattgcc ctgaggatgg aggttctggg ctgcgaggca    4260
caggacctct actga                                                     4275
```

<210> SEQ ID NO 4
<211> LENGTH: 1424
<212> TYPE: PRT
<213> ORGANISM: Homo sapiens

<400> SEQUENCE: 4

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
         35                  40                  45

Thr Leu Phe Val Glu Phe Thr Val His Leu Phe Asn Ile Ala Lys Pro
     50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190
```

```
His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
                260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
                355                 360                 365

Ile Gln Ile Arg Ser Val Ala Lys Lys His Pro Lys Thr Trp Val His
    370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
                420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
            595                 600                 605
```

```
Gln Ala Ser Asn Ile Met His Ser Ile Asn Gly Tyr Val Phe Asp Ser
    610             615             620

Leu Gln Leu Ser Val Cys Leu His Glu Val Ala Tyr Trp Tyr Ile Leu
625             630             635             640

Ser Ile Gly Ala Gln Thr Asp Phe Leu Ser Val Phe Ser Gly Tyr
            645             650             655

Thr Phe Lys His Lys Met Val Tyr Glu Asp Thr Leu Thr Leu Phe Pro
            660             665             670

Phe Ser Gly Glu Thr Val Phe Met Ser Met Glu Asn Pro Gly Leu Trp
        675             680             685

Ile Leu Gly Cys His Asn Ser Asp Phe Arg Asn Arg Gly Met Thr Ala
        690             695             700

Leu Leu Lys Val Ser Ser Cys Asp Lys Asn Thr Gly Asp Tyr Tyr Glu
705             710             715             720

Asp Ser Tyr Glu Asp Ile Ser Ala Tyr Leu Leu Ser Lys Asn Asn Ala
            725             730             735

Ile Glu Pro Arg Glu Ile Thr Arg Thr Thr Leu Gln Ser Asp Gln Glu
            740             745             750

Glu Ile Asp Tyr Asp Asp Thr Ile Ser Val Glu Met Lys Lys Glu Asp
        755             760             765

Phe Asp Ile Tyr Asp Glu Asp Glu Asn Gln Ser Pro Arg Ser Phe Gln
770             775             780

Lys Lys Thr Arg His Tyr Phe Ile Ala Ala Val Glu Arg Leu Trp Asp
785             790             795             800

Tyr Gly Met Ser Ser Pro His Val Leu Arg Asn Arg Ala Gln Ser
        805             810             815

Gly Ser Val Pro Gln Phe Lys Lys Val Val Phe Gln Glu Phe Thr Asp
            820             825             830

Gly Ser Phe Thr Gln Pro Leu Tyr Arg Gly Glu Leu Asn Glu His Leu
        835             840             845

Gly Leu Leu Gly Pro Tyr Ile Arg Ala Glu Val Glu Asp Asn Ile Met
850             855             860

Val Thr Phe Arg Asn Gln Ala Ser Arg Pro Tyr Ser Phe Tyr Ser Ser
865             870             875             880

Leu Ile Ser Tyr Glu Glu Asp Gln Arg Gln Gly Ala Glu Pro Arg Lys
            885             890             895

Asn Phe Val Lys Pro Asn Glu Thr Lys Thr Tyr Phe Trp Lys Val Gln
            900             905             910

His His Met Ala Pro Thr Lys Asp Glu Phe Asp Cys Lys Ala Trp Ala
        915             920             925

Tyr Phe Ser Asp Val Asp Leu Glu Lys Asp Val His Ser Gly Leu Ile
        930             935             940

Gly Pro Leu Leu Val Cys His Thr Asn Thr Leu Asn Pro Ala His Gly
945             950             955             960

Arg Gln Val Thr Val Gln Glu Phe Ala Leu Phe Phe Thr Ile Phe Asp
            965             970             975

Glu Thr Lys Ser Trp Tyr Phe Thr Glu Asn Met Glu Arg Asn Cys Arg
            980             985             990

Ala Pro Cys Asn Ile Gln Met Glu Asp Pro Thr Phe Lys Glu Asn Tyr
        995             1000            1005

Arg Phe His Ala Ile Asn Gly Tyr Ile Met Asp Thr Leu Pro Gly
    1010            1015            1020

Leu Val Met Ala Gln Asp Gln Arg Ile Arg Trp Tyr Leu Leu Ser
```

```
                 1025                1030                1035
Met Gly Ser Asn Glu Asn Ile His Ser Ile His Phe Ser Gly His
    1040                1045                1050
Val Phe Thr Val Arg Lys Lys Glu Glu Tyr Lys Met Ala Leu Tyr
    1055                1060                1065
Asn Leu Tyr Pro Gly Val Phe Glu Thr Val Glu Met Leu Pro Ser
    1070                1075                1080
Lys Ala Gly Ile Trp Arg Val Glu Cys Leu Ile Gly Glu His Leu
    1085                1090                1095
His Ala Gly Met Ser Thr Leu Phe Leu Val Tyr Ser Asn Lys Cys
    1100                1105                1110
Gln Thr Pro Leu Gly Met Ala Ser Gly His Ile Arg Asp Phe Gln
    1115                1120                1125
Ile Thr Ala Ser Gly Gln Tyr Gly Gln Trp Ala Pro Lys Leu Ala
    1130                1135                1140
Arg Leu His Tyr Ser Gly Ser Ile Asn Ala Trp Ser Thr Lys Glu
    1145                1150                1155
Pro Phe Ser Trp Ile Lys Val Asp Leu Leu Ala Pro Met Ile Ile
    1160                1165                1170
His Gly Ile Lys Thr Gln Gly Ala Arg Gln Lys Phe Ser Ser Leu
    1175                1180                1185
Tyr Ile Ser Gln Phe Ile Ile Met Tyr Ser Leu Asp Gly Lys Lys
    1190                1195                1200
Trp Gln Thr Tyr Arg Gly Asn Ser Thr Gly Thr Leu Met Val Phe
    1205                1210                1215
Phe Gly Asn Val Asp Ser Ser Gly Ile Lys His Asn Ile Phe Asn
    1220                1225                1230
Pro Pro Ile Ile Ala Arg Tyr Ile Arg Leu His Pro Thr His Tyr
    1235                1240                1245
Ser Ile Arg Ser Thr Leu Arg Met Glu Leu Met Gly Cys Asp Leu
    1250                1255                1260
Asn Ser Cys Ser Met Pro Leu Gly Met Glu Ser Lys Ala Ile Ser
    1265                1270                1275
Asp Ala Gln Ile Thr Ala Ser Ser Tyr Phe Thr Asn Met Phe Ala
    1280                1285                1290
Thr Trp Ser Pro Ser Lys Ala Arg Leu His Leu Gln Gly Arg Ser
    1295                1300                1305
Asn Ala Trp Arg Pro Gln Val Asn Asn Pro Lys Glu Trp Leu Gln
    1310                1315                1320
Val Asp Phe Gln Lys Thr Met Lys Val Thr Gly Val Thr Thr Gln
    1325                1330                1335
Gly Val Lys Ser Leu Leu Thr Ser Met Tyr Val Lys Glu Phe Leu
    1340                1345                1350
Ile Ser Ser Ser Gln Asp Gly His Gln Trp Thr Leu Phe Phe Gln
    1355                1360                1365
Asn Gly Lys Val Lys Val Phe Gln Gly Asn Gln Asp Ser Phe Thr
    1370                1375                1380
Pro Val Val Asn Ser Leu Asp Pro Pro Leu Leu Thr Arg Tyr Leu
    1385                1390                1395
Arg Ile His Pro Gln Ser Trp Val His Gln Ile Ala Leu Arg Met
    1400                1405                1410
Glu Val Leu Gly Cys Glu Ala Gln Asp Leu Tyr
    1415                1420
```

<210> SEQ ID NO 5
<211> LENGTH: 2220
<212> TYPE: DNA
<213> ORGANISM: Homo sapiens

<400> SEQUENCE: 5

| | | | | | |
|---|---|---|---|---|---|
| gccaccagaa | gatactacct | gggtgcagtg | gaactgtcat | gggactatat | gcaaagtgat | 60 |
| ctcggtgagc | tgcctgtgga | cgcaagattt | cctcctagag | tgccaaaatc | ttttccattc | 120 |
| aacacctcag | tcgtgtacaa | aaagactctg | tttgtagaat | tcacggttca | ccttttcaac | 180 |
| atcgctaagc | caaggccacc | ctggatgggt | ctgctaggtc | ctaccatcca | ggctgaggtt | 240 |
| tatgatacag | tggtcattac | acttaagaac | atggcttccc | atcctgtcag | tcttcatgct | 300 |
| gttggtgtat | cctactggaa | agcttctgag | ggagctgaat | atgatgatca | gaccagtcaa | 360 |
| agggagaaag | aagatgataa | agtcttccct | ggtggaagcc | atacatatgt | ctggcaggtc | 420 |
| ctgaaagaga | atggtccaat | ggcctctgac | ccactgtgcc | ttacctactc | atatctttct | 480 |
| catgtggacc | tggtaaaaga | cttgaattca | ggcctcattg | gagccctact | agtatgtaga | 540 |
| gaagggagtc | tggccaagga | aaagacacag | accttgcaca | aatttatact | acttttttgct | 600 |
| gtatttgatg | aagggaaaag | ttggcactca | gaaacaaaga | actccttgat | gcaggatagg | 660 |
| gatgctgcat | ctgctcgggc | ctggcctaaa | atgcacacag | tcaatggtta | tgtagccagg | 720 |
| tctctgccag | gtctgattgg | atgccacagg | aaatcagtct | attggcatgt | gattggaatg | 780 |
| ggcaccactc | ctgaagtgca | ctcaatattc | ctcgaaggtc | acacatttct | tgtgaggaac | 840 |
| catcgccagg | cgtccttgga | aatctcgcca | ataactttcc | ttactgctca | aacactcttg | 900 |
| atggaccttg | acagtttct | actgttttgt | catatctctt | cccaccaaca | tgatggcatg | 960 |
| gaagcttatg | tcaaagtaga | cagctgtcca | gaggaacccc | aactacgaat | gaaaaataat | 1020 |
| gaagaagcgg | aagactatga | tgatgatctt | actgattctg | aaatggatgt | ggtcaggttt | 1080 |
| gatgatgaca | actctccttc | ctttatccaa | attcgctcag | ttgccaagaa | gcatcctaaa | 1140 |
| acttgggtac | attacattgc | tgctgaagag | gaggactggg | actatgctcc | cttagtcctc | 1200 |
| gcccccgatg | acagaagtta | taaaagtcaa | tatttgaaca | atggccctca | gcggattggt | 1260 |
| aggaagtaca | aaaagtccg | atttatggca | tacacagatg | aaacctttaa | gactcgtgaa | 1320 |
| gctattcagc | atgaatcagg | aatcttggga | cctttacttt | atgggaagt | tggagacaca | 1380 |
| ctgttgatta | tatttaagaa | tcaagcaagc | agaccatata | acatctaccc | tcacggaatc | 1440 |
| actgatgtcc | gtccttttgta | ttcaaggaga | ttaccaaaag | gtgtaaaaca | tttgaaggat | 1500 |
| tttccaattc | tgccaggaga | aatattcaaa | tataaatgga | cagtgactgt | agaagatggg | 1560 |
| ccaactaaat | cagatcctcg | gtgcctgacc | cgctattact | ctagtttcgt | taatatggag | 1620 |
| agagatctag | cttcaggact | cattggccct | ctcctcatct | gctacaaaga | atctgtagat | 1680 |
| caaagaggaa | accagataat | gtcagacaag | aggaatgtca | tcctgttttc | tgtatttgat | 1740 |
| gagaaccgaa | gctggtacct | cacagagaat | atacaacgct | tctcccccaa | tccagctgga | 1800 |
| gtgcagcttg | aggatccaga | gttccaagcc | tccaacatca | tgcacagcat | caatggctat | 1860 |
| gttttttgata | gtttgcagtt | gtcagtttgt | ttgcatgagg | tggcatactg | gtacattcta | 1920 |
| agcattggag | cacagactga | cttccttttct | gtcttcttct | ctggatatac | cttcaaacac | 1980 |
| aaaatggtct | atgaagacac | actcacccta | ttcccattct | caggagaaac | tgtcttcatg | 2040 |
| tcgatggaaa | acccaggtct | atggattctg | gggtgccaca | actcagactt | tcggaacaga | 2100 |

```
ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
```

<210> SEQ ID NO 6
<211> LENGTH: 740
<212> TYPE: PRT
<213> ORGANISM: Homo sapiens

<400> SEQUENCE: 6

```
Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Ala Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                325                 330                 335

Met Lys Asn Asn Glu Glu Ala Glu Asp Tyr Asp Asp Asp Leu Thr Asp
            340                 345                 350

Ser Glu Met Asp Val Val Arg Phe Asp Asp Asp Asn Ser Pro Ser Phe
```

```
            355                 360                 365
Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Val Arg Phe Met Ala Tyr Thr
                420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495

His Leu Lys Asp Phe Pro Ile Leu Pro Gly Glu Ile Phe Lys Tyr Lys
                500                 505                 510

Trp Thr Val Thr Val Glu Asp Gly Pro Thr Lys Ser Asp Pro Arg Cys
            515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
                580                 585                 590

Arg Phe Leu Pro Asn Pro Ala Gly Val Gln Leu Glu Asp Pro Glu Phe
            595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
            675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg
            740

<210> SEQ ID NO 7
<211> LENGTH: 1932
<212> TYPE: DNA
<213> ORGANISM: Homo sapiens
```

<400> SEQUENCE: 7

```
agctttcaaa agaaaacacg acactatttt attgctgcag tggagaggct ctgggattat     60
gggatgagta gctccccaca tgttctaaga acagggctc agagtggcag tgtccctcag    120
ttcaagaaag ttgttttcca ggaatttact gatggctcct ttactcagcc cttataccgt    180
ggagaactaa atgaacattt gggactcctg ggccatata aagagcaga agttgaagat     240
aatatcatgg taactttcag aaatcaggcc tctcgtccct attccttcta ttctagcctt    300
atttcttatg aggaagatca gaggcaagga gcagaaccta gaaaaaactt tgtcaagcct    360
aatgaaacca aaacttactt tggaaagtg caacatcata tggcacccac taaagatgag    420
tttgactgca aagcctgggc ttatttctct gatgttgacc tggaaaaaga tgtgcactca    480
ggcctgattg accccttct ggtctgccac actaacacac tgaaccctgc tcatgggaga    540
caagtgacag tacaggaatt tgctctgttt ttcaccatct ttgatgagac caaaagctgg    600
tacttcactg aaaatatgga agaaactgc agggctccct gcaatatcca gatggaagat    660
cccactttta aagagaatta tcgcttccat gcaatcaatg ctacataat ggatacacta     720
cctggcttag taatggctca ggatcaaagg attcgatggt atctgctcag catgggcagc    780
aatgaaaaca tccattctat tcatttcagt ggacatgtgt tcactgtacg aaaaaaagag    840
gagtataaaa tggcactgta caatctctat ccaggtgttt ttgagacagt ggaaatgtta    900
ccatccaaag ctggaatttg cgggtggaa tgccttattg gcgagcatct acatgctggg     960
atgagcacac ttttctggt gtacagcaat aagtgtcaga ctcccctggg aatggcttct   1020
ggacacatta gagattttca gattacagct tcaggacaat atggacagtg gccccaaag    1080
ctggccagac ttcattattc cggatcaatc aatgcctgga gcaccaagga gccctttttct   1140
tggatcaagg tggatctgtt ggcaccaatg attattcacg gcatcaagac ccagggtgcc   1200
cgtcagaagt tctccagcct ctacatctct cagtttatca tcatgtatag tcttgatggg   1260
aagaagtggc agacttatcg aggagcctcc actggaacct aatggtctt ctttggcaat    1320
gtggattcat ctgggataaa acacaatatt tttaaccctc caattattgc tcgatacatc   1380
cgtttgcacc caactcatta tagcattcgc agcactcttc gcatggagtt gatgggctgt   1440
gatttaaata gttgcagcat gccattggga atggagagta aagcaatatc agatgcacag   1500
attactgctt catcctactt taccaatatg tttgccacct ggtctccttc aaaagctcga   1560
cttcacctcc aagggaggag taatgcctgg agacctcagg tgaataatcc aaaagagtgg   1620
ctgcaagtgg acttccagaa gacaatgaaa gtcacaggag taactactca gggagtaaaa   1680
tctctgctta ccagcatgta tgtgaaggag ttcctcatct ccagcagtca gatggccat    1740
cagtggactc tcttttttca gaatggcaaa gtaaaggttt tcagggaaa tcaagactcc   1800
ttcacccctg tggtgaactc tctagaccca ccgttactga ctcgctacct tcgaattcac   1860
ccccagagtt gggtgcacca gattgccctg aggatggagg ttctgggctg cgaggcacag   1920
gacctctact ga                                                      1932
```

<210> SEQ ID NO 8
<211> LENGTH: 643
<212> TYPE: PRT
<213> ORGANISM: Homo sapiens

<400> SEQUENCE: 8

```
Ser Phe Gln Lys Lys Thr Arg His Tyr Phe Ile Ala Ala Val Glu Arg
1               5                   10                  15
```

```
Leu Trp Asp Tyr Gly Met Ser Ser Pro His Val Leu Arg Asn Arg
            20                  25                  30

Ala Gln Ser Gly Ser Val Pro Gln Phe Lys Val Phe Gln Glu
        35                  40                  45

Phe Thr Asp Gly Ser Phe Thr Gln Pro Leu Tyr Arg Gly Glu Leu Asn
50                      55                  60

Glu His Leu Gly Leu Leu Gly Pro Tyr Ile Arg Ala Glu Val Glu Asp
65                  70                  75                  80

Asn Ile Met Val Thr Phe Arg Asn Gln Ala Ser Arg Pro Tyr Ser Phe
                85                  90                  95

Tyr Ser Ser Leu Ile Ser Tyr Glu Glu Asp Gln Arg Gln Gly Ala Glu
            100                 105                 110

Pro Arg Lys Asn Phe Val Lys Pro Asn Glu Thr Lys Thr Tyr Phe Trp
            115                 120                 125

Lys Val Gln His His Met Ala Pro Thr Lys Asp Glu Phe Asp Cys Lys
130                 135                 140

Ala Trp Ala Tyr Phe Ser Asp Val Asp Leu Glu Lys Asp Val His Ser
145                 150                 155                 160

Gly Leu Ile Gly Pro Leu Leu Val Cys His Thr Asn Thr Leu Asn Pro
                165                 170                 175

Ala His Gly Arg Gln Val Thr Val Gln Glu Phe Ala Leu Phe Phe Thr
            180                 185                 190

Ile Phe Asp Glu Thr Lys Ser Trp Tyr Phe Thr Glu Asn Met Glu Arg
            195                 200                 205

Asn Cys Arg Ala Pro Cys Asn Ile Gln Met Glu Asp Pro Thr Phe Lys
210                 215                 220

Glu Asn Tyr Arg Phe His Ala Ile Asn Gly Tyr Ile Met Asp Thr Leu
225                 230                 235                 240

Pro Gly Leu Val Met Ala Gln Asp Gln Arg Ile Arg Trp Tyr Leu Leu
                245                 250                 255

Ser Met Gly Ser Asn Glu Asn Ile His Ser Ile His Phe Ser Gly His
            260                 265                 270

Val Phe Thr Val Arg Lys Lys Glu Glu Tyr Lys Met Ala Leu Tyr Asn
            275                 280                 285

Leu Tyr Pro Gly Val Phe Glu Thr Val Glu Met Leu Pro Ser Lys Ala
290                 295                 300

Gly Ile Trp Arg Val Glu Cys Leu Ile Gly Glu His Leu His Ala Gly
305                 310                 315                 320

Met Ser Thr Leu Phe Leu Val Tyr Ser Asn Lys Cys Gln Thr Pro Leu
                325                 330                 335

Gly Met Ala Ser Gly His Ile Arg Asp Phe Gln Ile Thr Ala Ser Gly
            340                 345                 350

Gln Tyr Gly Gln Trp Ala Pro Lys Leu Ala Arg Leu His Tyr Ser Gly
            355                 360                 365

Ser Ile Asn Ala Trp Ser Thr Lys Glu Pro Phe Ser Trp Ile Lys Val
370                 375                 380

Asp Leu Leu Ala Pro Met Ile Ile His Gly Ile Lys Thr Gln Gly Ala
385                 390                 395                 400

Arg Gln Lys Phe Ser Ser Leu Tyr Ile Ser Gln Phe Ile Ile Met Tyr
                405                 410                 415

Ser Leu Asp Gly Lys Lys Trp Gln Thr Tyr Arg Gly Ala Ser Thr Gly
            420                 425                 430
```

```
Thr Leu Met Val Phe Phe Gly Asn Val Asp Ser Ser Gly Ile Lys His
            435                 440                 445

Asn Ile Phe Asn Pro Pro Ile Ile Ala Arg Tyr Ile Arg Leu His Pro
        450                 455                 460

Thr His Tyr Ser Ile Arg Ser Thr Leu Arg Met Glu Leu Met Gly Cys
465                 470                 475                 480

Asp Leu Asn Ser Cys Ser Met Pro Leu Gly Met Glu Ser Lys Ala Ile
            485                 490                 495

Ser Asp Ala Gln Ile Thr Ala Ser Ser Tyr Phe Thr Asn Met Phe Ala
        500                 505                 510

Thr Trp Ser Pro Ser Lys Ala Arg Leu His Leu Gln Gly Arg Ser Asn
515                 520                 525

Ala Trp Arg Pro Gln Val Asn Asn Pro Lys Glu Trp Leu Gln Val Asp
        530                 535                 540

Phe Gln Lys Thr Met Lys Val Thr Gly Val Thr Thr Gln Gly Val Lys
545                 550                 555                 560

Ser Leu Leu Thr Ser Met Tyr Val Lys Glu Phe Leu Ile Ser Ser Ser
            565                 570                 575

Gln Asp Gly His Gln Trp Thr Leu Phe Phe Gln Asn Gly Lys Val Lys
        580                 585                 590

Val Phe Gln Gly Asn Gln Asp Ser Phe Thr Pro Val Val Asn Ser Leu
        595                 600                 605

Asp Pro Pro Leu Leu Thr Arg Tyr Leu Arg Ile His Pro Gln Ser Trp
        610                 615                 620

Val His Gln Ile Ala Leu Arg Met Glu Val Leu Gly Cys Glu Ala Gln
625                 630                 635                 640

Asp Leu Tyr

<210> SEQ ID NO 9
<211> LENGTH: 18
<212> TYPE: PRT
<213> ORGANISM: Homo sapiens

<400> SEQUENCE: 9

Ile Ile Ala Arg Tyr Ile Arg Leu His Pro Thr His Tyr Ser Ile Arg
1               5                   10                  15

Ser Thr

<210> SEQ ID NO 10
<211> LENGTH: 573
<212> TYPE: PRT
<213> ORGANISM: Homo sapiens

<400> SEQUENCE: 10

Ser Phe Ser Gln Asn Ser Arg His Pro Ser Thr Arg Gln Lys Gln Phe
1               5                   10                  15

Asn Ala Thr Thr Ile Pro Glu Asn Asp Ile Glu Lys Thr Asp Pro Trp
            20                  25                  30

Phe Ala His Arg Thr Pro Met Pro Lys Ile Gln Asn Val Ser Ser Ser
        35                  40                  45

Asp Leu Leu Met Leu Leu Arg Gln Ser Pro Thr Pro His Gly Leu Ser
    50                  55                  60

Leu Ser Asp Leu Gln Glu Ala Lys Tyr Glu Thr Phe Ser Asp Asp Pro
65              70                  75                  80

Ser Pro Gly Ala Ile Asp Ser Asn Asn Ser Leu Ser Glu Met Thr His
            85                  90                  95
```

```
Phe Arg Pro Gln Leu His His Ser Gly Asp Met Val Phe Thr Pro Glu
                100                 105                 110

Ser Gly Leu Gln Leu Arg Leu Asn Glu Lys Leu Gly Thr Ala Ala
        115                 120                 125

Thr Glu Leu Lys Lys Leu Asp Phe Lys Val Ser Ser Thr Ser Asn Asn
130                 135                 140

Leu Ile Ser Thr Ile Pro Ser Asp Asn Leu Ala Ala Gly Thr Asp Asn
145                 150                 155                 160

Thr Ser Ser Leu Gly Pro Pro Ser Met Pro Val His Tyr Asp Ser Gln
                165                 170                 175

Leu Asp Thr Thr Leu Phe Gly Lys Lys Ser Ser Pro Leu Thr Glu Ser
        180                 185                 190

Gly Gly Pro Leu Ser Leu Ser Glu Glu Asn Asn Asp Ser Lys Leu Leu
        195                 200                 205

Glu Ser Gly Leu Met Asn Ser Gln Glu Ser Ser Trp Gly Lys Asn Val
        210                 215                 220

Ser Ser Thr Glu Ser Gly Arg Leu Phe Lys Gly Lys Arg Ala His Gly
225                 230                 235                 240

Pro Ala Leu Leu Thr Lys Asp Asn Ala Leu Phe Lys Val Ser Ile Ser
                245                 250                 255

Leu Leu Lys Thr Asn Lys Thr Ser Asn Asn Ser Ala Thr Asn Arg Lys
                260                 265                 270

Thr His Ile Asp Gly Pro Ser Leu Leu Ile Glu Asn Ser Pro Ser Val
        275                 280                 285

Trp Gln Asn Ile Leu Glu Ser Asp Thr Glu Phe Lys Lys Val Thr Pro
        290                 295                 300

Leu Ile His Asp Arg Met Leu Met Asp Lys Asn Ala Thr Ala Leu Arg
305                 310                 315                 320

Leu Asn His Met Ser Asn Lys Thr Thr Ser Ser Lys Asn Met Glu Met
                325                 330                 335

Val Gln Gln Lys Lys Glu Gly Pro Ile Pro Pro Asp Ala Gln Asn Pro
        340                 345                 350

Asp Met Ser Phe Phe Lys Met Leu Phe Leu Pro Glu Ser Ala Arg Trp
        355                 360                 365

Ile Gln Arg Thr His Gly Lys Asn Ser Leu Asn Ser Gly Gln Gly Pro
        370                 375                 380

Ser Pro Lys Gln Leu Val Ser Leu Gly Pro Glu Lys Ser Val Glu Gly
385                 390                 395                 400

Gln Asn Phe Leu Ser Glu Lys Asn Lys Val Val Gly Lys Gly Glu
                405                 410                 415

Phe Thr Lys Asp Val Gly Leu Lys Glu Met Val Phe Pro Ser Ser Arg
                420                 425                 430

Asn Leu Phe Leu Thr Asn Leu Asp Asn Leu His Glu Asn Asn Thr His
        435                 440                 445

Asn Gln Glu Lys Lys Ile Gln Glu Glu Ile Glu Lys Lys Glu Thr Leu
        450                 455                 460

Ile Gln Glu Asn Val Val Leu Pro Gln Ile His Thr Val Thr Gly Thr
465                 470                 475                 480

Lys Asn Phe Met Lys Asn Leu Phe Leu Leu Ser Thr Arg Gln Asn Val
                485                 490                 495

Glu Gly Ser Tyr Asp Gly Ala Tyr Ala Pro Val Leu Gln Asp Phe Arg
                500                 505                 510
```

Ser Leu Asn Asp Ser Thr Asn Arg Thr Lys Lys His Thr Ala His Phe
            515                 520                 525

Ser Lys Lys Gly Glu Glu Asn Leu Glu Gly Leu Gly Asn Gln Thr
    530                 535                 540

Lys Gln Ile Val Glu Lys Tyr Ala Cys Thr Thr Arg Ile Ser Pro Asn
545                 550                 555                 560

Thr Ser Gln Gln Asn Phe Val Thr Gln Arg Ser Lys Arg
                565                 570

<210> SEQ ID NO 11
<211> LENGTH: 2220
<212> TYPE: DNA
<213> ORGANISM: Homo sapiens

<400> SEQUENCE: 11

| | | | | | |
|---|---|---|---|---|---|
| gccaccagaa | gatactacct | gggtgcagtg | gaactgtcat | gggactatat | gcaaagtgat | 60 |
| ctcggtgagc | tgcctgtgga | cgcaagattt | cctcctagag | tgccaaaatc | ttttccattc | 120 |
| aacacctcag | tcgtgtacaa | aaagactctg | tttgtagaat | tcacggttca | ccttttcaac | 180 |
| atcgctaagc | caaggccacc | ctggatgggt | ctgctaggtc | ctaccatcca | ggctgaggtt | 240 |
| tatgatacag | tggtcattac | acttaagaac | atggcttccc | atcctgtcag | tcttcatgct | 300 |
| gttggtgtat | cctactggaa | agcttctgag | ggagctgaat | atgatgatca | gaccagtcaa | 360 |
| agggagaaag | aagatgataa | agtcttccct | ggtggaagcc | atacatatgt | ctggcaggtc | 420 |
| ctgaaagaga | atggtccaat | ggcctctgac | ccactgtgcc | ttacctactc | atatctttct | 480 |
| catgtggacc | tggtaaaaga | cttgaattca | ggcctcattg | gagccctact | agtatgtaga | 540 |
| gaagggagtc | tggccaagga | aaagacacag | accttgcaca | aatttatact | acttttgct | 600 |
| gtatttgatg | aagggaaaag | ttggcactca | gaaacaaaga | actccttgat | gcaggatagg | 660 |
| gatgctgcat | ctgctcgggc | ctggcctaaa | atgcacacag | tcaatggtta | tgtacagagg | 720 |
| tctctgccag | gtctgattgg | atgccacagg | aaatcagtct | attggcatgt | gattggaatg | 780 |
| ggcaccactc | ctgaagtgca | ctcaatattc | ctcgaaggtc | acacatttct | tgtgaggaac | 840 |
| catcgccagg | cgtccttgga | aatctcgcca | taactttcc | ttactgctca | aacactcttg | 900 |
| atggaccttg | acagtttct | actgttttgt | catatctctt | cccaccaaca | tgatggcatg | 960 |
| gaagcttatg | tcaaagtaga | cagctgtcca | gaggaacccc | aactacgaat | gaaaaataat | 1020 |
| gaagaagcgg | aagactatga | tgatgatctt | actgattctg | aaatggatgt | ggtcaggttt | 1080 |
| gatgatgaca | actctccttc | ctttatccaa | attcgctcag | ttgccaagaa | gcatcctaaa | 1140 |
| acttgggtac | attacattgc | tgctgaagag | gaggactggg | actatgctcc | cttagtcctc | 1200 |
| gcccccgatg | acagaagtta | taaagtcaa | tatttgaaca | atggccctca | gcggattggt | 1260 |
| aggaagtaca | aaaagtccg | atttatggca | tacacagatg | aaacctttaa | gactcgtgaa | 1320 |
| gctattcagc | atgaatcagg | aatcttggga | cctttacttt | atgggaagt | tggagacaca | 1380 |
| ctgttgatta | tatttaagaa | tcaagcaagc | agaccatata | acatctaccc | tcacggaatc | 1440 |
| actgatgtcc | gtcctttgta | ttcaaggaga | ttaccaaaag | gtgtaaaaca | tttgaaggat | 1500 |
| tttccaattc | tgccaggaga | aatattcaaa | tataaatgga | cagtgactgt | agaagatggg | 1560 |
| ccaactaaat | cagatcctcg | gtgcctgacc | cgctattact | ctagtttcgt | taatatggag | 1620 |
| agagatctag | cttcaggact | cattggccct | ctcctcatct | gctacaaaga | atctgtagat | 1680 |
| caaagaggaa | accagataat | gtcagacaag | aggaatgtca | tcctgttttc | tgtatttgat | 1740 |
| gagaaccgaa | gctggtacct | cacagagaat | atacaacgct | ttctccccaa | tccagctgga | 1800 |

```
gtgcagcttg aggatccaga gttccaagcc tccaacatca tgcacagcat caatggctat    1860
gtttttgata gtttgcagtt gtcagtttgt ttgcatgagg tggcatactg gtacattcta    1920
agcattggag cacagactga cttcctttct gtcttcttct ctggatatac cttcaaacac    1980
aaaatggtct atgaagacac actcacccta ttcccattct caggagaaac tgtcttcatg    2040
tcgatggaaa acccaggtct atggattctg gggtgccaca actcagactt tcggaacaga    2100
ggcatgaccg ccttactgaa ggtttctagt tgtgacaaga acactggtga ttattacgag    2160
gacagttatg aagatatttc agcatacttg ctgagtaaaa acaatgccat tgaaccaaga    2220
```

<210> SEQ ID NO 12
<211> LENGTH: 740
<212> TYPE: PRT
<213> ORGANISM: Homo sapiens

<400> SEQUENCE: 12

```
Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Val His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
    210                 215                 220

Ala Arg Ala Trp Pro Lys Met His Thr Val Asn Gly Tyr Val Gln Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
    290                 295                 300
```

-continued

```
Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
            325                 330                 335

Met Lys Asn Asn Glu Glu Ala Glu Asp Tyr Asp Asp Leu Thr Asp
        340                 345                 350

Ser Glu Met Asp Val Val Arg Phe Asp Asp Asn Ser Pro Ser Phe
    355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
        435                 440                 445

Leu Gly Pro Leu Leu Tyr Gly Glu Val Gly Asp Thr Leu Leu Ile Ile
    450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510

Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
            565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
    610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
            645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
    690                 695                 700

Leu Leu Lys Val Ser Ser Cys Asp Lys Asn Thr Gly Asp Tyr Tyr Glu
705                 710                 715                 720
```

```
Asp Ser Tyr Glu Asp Ile Ser Ala Tyr Leu Leu Ser Lys Asn Asn Ala
                725                 730                 735

Ile Glu Pro Arg
        740

<210> SEQ ID NO 13
<211> LENGTH: 1932
<212> TYPE: DNA
<213> ORGANISM: Homo sapiens

<400> SEQUENCE: 13
agctttcaaa agaaaacacg acactatttt attgctgcag tggagaggct ctgggattat     60
gggatgagta gctccccaca tgttctaaga acagggctc agagtggcag tgtccctcag    120
ttcaagaaag ttgttttcca ggaatttact gatggctcct ttactcagcc cttataccgt    180
ggagaactaa atgaacattt gggactcctg gggccatata agagcaga agttgaagat     240
aatatcatgg taactttcag aaatcaggcc tctcgtccct attccttcta ttctagcctt    300
atttcttatg aggaagatca gaggcaagga gcagaaccta gaaaaaactt tgtcaagcct    360
aatgaaacca aaacttactt ttggaaagtg caacatcata tggcacccac taaagatgag    420
tttgactgca aagcctgggc ttatttctct gatgttgacc tggaaaaaga tgtgcactca    480
ggcctgattg accccttct ggtctgccac actaacacac tgaaccctgc tcatgggaga    540
caagtgcacag tacaggaatt tgctctgttt ttcaccatct tgatgagac caaaagctgg    600
tacttcactg aaaatatgga agaaactgc agggctccct gcaatatcca gatggaagat    660
cccactttta aagagaatta tcgcttccat gcaatcaatg ctacataat ggatacacta    720
cctggcttag taatggctca ggatcaaagg attcgatggt atctgctcag catgggcagc    780
aatgaaaaca tccattctat tcatttcagt ggacatgtgt tcactgtacg aaaaaaagag    840
gagtataaaa tggcactgta caatctctat ccaggtgttt ttgagacagt ggaaatgtta    900
ccatccaaag ctggaatttg gcgggtggaa tgccttattg cgagcatct acatgctggg    960
atgagcacac ttttctggt gtacagcaat aagtgtcaga ctcccctggg aatggcttct   1020
ggacacatta gagattttca gattacagct tcaggacaat atggacagtg gcccccaaag   1080
ctggccagac ttcattattc cggatcaatc aatgcctgga gcaccaagga gcccttttct   1140
tggatcaagg tggatctgtt ggcaccaatg attattcacg gcatcaagac ccagggtgcc   1200
cgtcagaagt tctccagcct ctacatctct cagtttatca tcatgtatag tcttgatggg   1260
aagaagtggc agacttatcg aggacagtcc actggaacct taatggtctt ctttggcaat   1320
gtggattcat ctgggataaa acacaatatt tttaacccctc caattattgc tcgatacatc   1380
cgtttgcacc caactcatta tagcattcgc agcactcttc gcatggagtt gatgggctgt   1440
gatttaaata gttgcagcat gccattggga atggagagta agcaatatc agatgcacag   1500
attactgctt catcctactt taccaatatg tttgccacct ggtctccttc aaaagctcga   1560
cttcacctcc aagggaggag taatgcctgg agacctcagg tgaataatcc aaaagagtgg   1620
ctgcaagtgg acttccagaa gacaatgaaa gtcacaggag taactactca gggagtaaaa   1680
tctctgctta ccagcatgta tgtgaaggag ttcctcatct ccagcagtca agatggccat   1740
cagtggactc tcttttttca gaatggcaaa gtaaaggttt tcagggaaa tcaagactcc   1800
ttcacacctg tggtgaactc tctagaccca ccgttactga ctcgctacct tcgaattcac   1860
ccccagagtt gggtgcacca gattgccctg aggatggagg ttctgggctg cgaggcacag   1920
gacctctact ga                                                        1932
```

```
<210> SEQ ID NO 14
<211> LENGTH: 643
<212> TYPE: PRT
<213> ORGANISM: Homo sapiens

<400> SEQUENCE: 14

Ser Phe Gln Lys Lys Thr Arg His Tyr Phe Ile Ala Ala Val Glu Arg
1               5                   10                  15

Leu Trp Asp Tyr Gly Met Ser Ser Pro His Val Leu Arg Asn Arg
            20                  25                  30

Ala Gln Ser Gly Ser Val Pro Gln Phe Lys Lys Val Val Phe Gln Glu
        35                  40                  45

Phe Thr Asp Gly Ser Phe Thr Gln Pro Leu Tyr Arg Gly Glu Leu Asn
    50                  55                  60

Glu His Leu Gly Leu Leu Gly Pro Tyr Ile Arg Ala Glu Val Glu Asp
65              70                  75                  80

Asn Ile Met Val Thr Phe Arg Asn Gln Ala Ser Arg Pro Tyr Ser Phe
                85                  90                  95

Tyr Ser Ser Leu Ile Ser Tyr Glu Glu Asp Gln Arg Gln Gly Ala Glu
            100                 105                 110

Pro Arg Lys Asn Phe Val Lys Pro Asn Glu Thr Lys Thr Tyr Phe Trp
        115                 120                 125

Lys Val Gln His His Met Ala Pro Thr Lys Asp Glu Phe Asp Cys Lys
    130                 135                 140

Ala Trp Ala Tyr Phe Ser Asp Val Asp Leu Glu Lys Asp Val His Ser
145                 150                 155                 160

Gly Leu Ile Gly Pro Leu Leu Val Cys His Thr Asn Thr Leu Asn Pro
                165                 170                 175

Ala His Gly Arg Gln Val Thr Val Gln Glu Phe Ala Leu Phe Phe Thr
            180                 185                 190

Ile Phe Asp Glu Thr Lys Ser Trp Tyr Phe Thr Glu Asn Met Glu Arg
        195                 200                 205

Asn Cys Arg Ala Pro Cys Asn Ile Gln Met Glu Asp Pro Thr Phe Lys
    210                 215                 220

Glu Asn Tyr Arg Phe His Ala Ile Asn Gly Tyr Ile Met Asp Thr Leu
225                 230                 235                 240

Pro Gly Leu Val Met Ala Gln Asp Gln Arg Ile Arg Trp Tyr Leu Leu
                245                 250                 255

Ser Met Gly Ser Asn Glu Asn Ile His Ser Ile His Phe Ser Gly His
            260                 265                 270

Val Phe Thr Val Arg Lys Lys Glu Glu Tyr Lys Met Ala Leu Tyr Asn
        275                 280                 285

Leu Tyr Pro Gly Val Phe Glu Thr Val Glu Met Leu Pro Ser Lys Ala
    290                 295                 300

Gly Ile Trp Arg Val Glu Cys Leu Ile Gly Glu His Leu His Ala Gly
305                 310                 315                 320

Met Ser Thr Leu Phe Leu Val Tyr Ser Asn Lys Cys Gln Thr Pro Leu
                325                 330                 335

Gly Met Ala Ser Gly His Ile Arg Asp Phe Gln Ile Thr Ala Ser Gly
            340                 345                 350

Gln Tyr Gly Gln Trp Ala Pro Lys Leu Ala Arg Leu His Tyr Ser Gly
        355                 360                 365

Ser Ile Asn Ala Trp Ser Thr Lys Glu Pro Phe Ser Trp Ile Lys Val
```

```
                  370                 375                 380
Asp Leu Leu Ala Pro Met Ile Ile His Gly Ile Lys Thr Gln Gly Ala
385                 390                 395                 400

Arg Gln Lys Phe Ser Ser Leu Tyr Ile Ser Gln Phe Ile Ile Met Tyr
                405                 410                 415

Ser Leu Asp Gly Lys Lys Trp Gln Thr Tyr Arg Gly Gln Ser Thr Gly
                420                 425                 430

Thr Leu Met Val Phe Phe Gly Asn Val Asp Ser Ser Gly Ile Lys His
            435                 440                 445

Asn Ile Phe Asn Pro Pro Ile Ile Ala Arg Tyr Ile Arg Leu His Pro
        450                 455                 460

Thr His Tyr Ser Ile Arg Ser Thr Leu Arg Met Glu Leu Met Gly Cys
465                 470                 475                 480

Asp Leu Asn Ser Cys Ser Met Pro Leu Gly Met Glu Ser Lys Ala Ile
                485                 490                 495

Ser Asp Ala Gln Ile Thr Ala Ser Ser Tyr Phe Thr Asn Met Phe Ala
                500                 505                 510

Thr Trp Ser Pro Ser Lys Ala Arg Leu His Leu Gln Gly Arg Ser Asn
            515                 520                 525

Ala Trp Arg Pro Gln Val Asn Asn Pro Lys Glu Trp Leu Gln Val Asp
        530                 535                 540

Phe Gln Lys Thr Met Lys Val Thr Gly Val Thr Thr Gln Gly Val Lys
545                 550                 555                 560

Ser Leu Leu Thr Ser Met Tyr Val Lys Glu Phe Leu Ile Ser Ser Ser
                565                 570                 575

Gln Asp Gly His Gln Trp Thr Leu Phe Phe Gln Asn Gly Lys Val Lys
                580                 585                 590

Val Phe Gln Gly Asn Gln Asp Ser Phe Thr Pro Val Val Asn Ser Leu
            595                 600                 605

Asp Pro Pro Leu Leu Thr Arg Tyr Leu Arg Ile His Pro Gln Ser Trp
        610                 615                 620

Val His Gln Ile Ala Leu Arg Met Glu Val Leu Gly Cys Glu Ala Gln
625                 630                 635                 640

Asp Leu Tyr
```